(12) United States Patent
Mohnen et al.

(10) Patent No.: US 7,619,077 B2
(45) Date of Patent: Nov. 17, 2009

(54) **NUCLEIC ACIDS ENCODING A GALACTURONOSYL TRANFERASE ENZYME (GALAT1) FROM *ARABIDOPSIS***

(75) Inventors: Debra Mohnen, Athens, GA (US); Jason Dwight Sterling, Athens, GA (US); Ron Lou Doong, Peoria, IL (US); Venkata Siva Kumar Kolli, Duluth, GA (US); Michael G. Hahn, Athens, GA (US)

(73) Assignee: University of Georgia Research Foundation, Athens, GA (US)

( * ) Notice: Subject to any disclaimer, the term of this patent is extended or adjusted under 35 U.S.C. 154(b) by 59 days.

(21) Appl. No.: 10/544,180

(22) PCT Filed: Feb. 5, 2004

(86) PCT No.: PCT/US2004/003545

§ 371 (c)(1),
(2), (4) Date: Mar. 8, 2006

(87) PCT Pub. No.: WO2004/072250

PCT Pub. Date: Aug. 26, 2004

(65) Prior Publication Data

US 2006/0150280 A1 Jul. 6, 2006

Related U.S. Application Data

(60) Provisional application No. 60/445,539, filed on Feb. 6, 2003.

(51) Int. Cl.
*C07H 21/04* (2006.01)
*C12N 15/82* (2006.01)
*A01H 5/00* (2006.01)

(52) U.S. Cl. .................. 536/23.2; 536/23.6; 435/320.1; 800/295; 800/298

(58) Field of Classification Search ....................... None
See application file for complete search history.

(56) References Cited

U.S. PATENT DOCUMENTS 5,294,593 A * 3/1994 Khan .......................... 504/100
2002/0160378 A1* 10/2002 Harper et al. .................. 435/6
2004/0034888 A1* 2/2004 Liu et al. ..................... 800/289

OTHER PUBLICATIONS

Shinn et al. *Arabidopsis* cDNA clones. (2001) GenBank Accession AY039515, pp. 1-3.*
Lazar et al. Transforming growth factor alpha: mutation of aspartice acid 47 and leucine 48 results in different biological activities. (1988) MCB, vol. 8, pp. 1247-1252.*
Hill et al. Functional analysis of conserved histidines in ADP-Glucose pyrophosphorylase from *Escherichia coli*. (1998) Biochem. and Biophys. Res. Comm., vol. 244, pp. 573-577.*
Guo et al. Protein tolerance to random amino acid change. (2004) PNAS, vol. 101, pp. 9205-9210.*
Brummell et al. Cell wall metabolism in fruit softening and quality and its manipulation in transgenic plants. (2001) PMB; vol. 47, pp. 311-340.*
Tavares et al. Aroganization and structural evolution of four multigene families in *Arabidopsis thaliana*: AtLCAD, AtLGT, AtMYST, and AtHD-GL2. (2000) PMB; vol. 42, pp. 703-717.*
Borkhart, B. et al. "Remodeling pectin structure in potato"; Plant Biology 2000. Annual Meeting of American Society of Plant Physiologists. vol. 2000, pp. 81, Abstract.
Cheuk, R. et al. "*Arabidopsis thanliana* unknown protein (At3g61130/T20K12_30)mRNA, complete cds"; GenBank, Accession No. BT000630. Sep. 25, 2002.
Mohnen, D. et al. "Pectin biosynthesis: Identification of a proposed galacturonosyltransferase gene family in *Arabidopsis thaliana*"; 227th ACS National Meeting (2004 ACS, Washington DC). Abstract. Mar. 28-Apr. 1, 2004.
Mohnen, D. et al. "Exploring the potential of pectin biosynthetic enzymes for industrial applications"; 230th ACS National Meeting. Aug. 28-Sep. 1, 2005. Abstract.
Mohnen, D. et al. "Pectin synthesis and its relevance to understanding pectin function"; 229th ACS National Meeting. Mar. 13-17, 2005. Abstract.
Mohnen, D. et al. "A multi-enzyme approach to study pectin biosyntheses"; Plant Bioilogy 1999. Annual Meeting American Society of Plant Physiologists Jul. 24-28, 1999. Abstract.
Shinn, P. et al. "*Arabidopsis thaliana* AT3g61130/T20K12_30 mRNA, complete cds"; GenBank, Accession No. AY039515. Jun. 20, 2001.
Sterling, J.D. et al. "Functional identification of an *Arabidopsis* pectin biosynthetic homogalacturonan galacturonosyltransferase"; PNAS Mar. 28, 2006, 103(13):5236-5241.
Tavares, R. et al. "Organization and structural evolution of four multigene families in *Arabidopsis thaliana*: AtLCAD, AtLGT, AtMYST and AtHD-GL2"; Plant Molecular Biology. 2000, 42:703-717.
Tavares, R. "*Arabidopsis thaliana* LGT1 gene, and partial FUSCA6 gene"; GenBank, Accession No. AJ243015. Jun. 1, 2001.

(Continued)

*Primary Examiner*—Cathy Kingdon Worley
(74) *Attorney, Agent, or Firm*—Davis Wright Tremaine LLP

(57) ABSTRACT

The invention provides an isolated nucleic acid molecule encoding the polypeptide GALAT1 having galacturonosyltransferase (GalAT) activity. The *Arabidopsis* GALAT1 sequence disclosed represents the first pectin biosynthetic glycosyltransferase gene isolated from plants. The invention further provides 14 GALAT and 10 GALAT-like gene superfamily members. The identification of the GALAT gene superfamily offers new opportunities to modulate pectin synthesis in vivo and in vitro by modulating the GALAT gene, for example, transgenic plants that produce modified pectins can be generated by altering the GALAT gene. Since modified pectins are predicted to affect plant growth, development, and plant defense responses, the transgenic plants are expected to have improved agricultural value. The modified pectins isolated from such transgenic plants are useful as gelling and stabilizing agents in the food, neutraceutical, and pharmaceutical industries. The expressed proteins, and variants thereof, of the GALAT superfamily are useful to produce in vitro modified pectins of commercial value.

6 Claims, 8 Drawing Sheets

OTHER PUBLICATIONS

Faik, A. et al. (2002) "An *Arabidopsis* gene encoding an α-xylosyltransferase involved in xyloglucan biosynthesis"; *Proc. Natl. Acad. Sci. USA* 99:7797-7802.

Keegstra, K. et al. (2001) "Plant glycosyltransferases"; *Curr. Opin. Plant Biol.* 4:219-224.

Madson, M. et al. (2003) "The MUR3 gene of *Arabidopsis* encodes a xyloglucan galactosyltransferase that is evolutionarily related to animal exostosins"; *Plant Cell* 15:1662-1670.

Mallisard, M. et al. (2000) "Expression of functional soluble forms of human β-1,4-Galactosyltransferase I, α-2,6-sialytransferase, and α-1,3-fucosyltransferase VI in the methylotrophic yeast *Pichia pastoris*"; *Biochem. Biophys. Res. Commun.* 267:169-173.

Mohnen, D. (2002) "Biosynthesis of pectins"; Pectins and their Manipulation, G.B. Seymour et al., Blackwell Publishing and CRC Press, Oxford, pp. 52-98.

\* cited by examiner

SEQUENCE LISTING

<160> NUMBER OF SEQ ID NOS: 50

<210> SEQ ID NO 1
<211> LENGTH: 2022
<212> TYPE: DNA
<213> ORGANISM: Arabidopsis thaliana

<400> SEQUENCE: 1
atggcgctaa agcgagggct atctggagtt aaccggatta gaggaagtgg tggtggatct    60

-continued

```
cgatctgtgc ttgtgcttct catattttc tgtgttttg cacctctttg cttctttgtt       120
ggccgaggag tgtatatcga ttcctcaaat gattattcaa ttgtttctgt gaagcagaat      180
cttgactgga gagaacgttt agcaatgcaa tctgttagat ctcttttctc gaaagagata     240
ctagatgtta tagcaaccag cacagctgat ttgggtcctc ttagccttga ttcttttaag     300
aaaaacaatt tgtctgcatc atggcgggga accggagtag accctccctt tagacattct    360
gagaatccag caactcctga tgtcaaatct aataacctga tgaaaaacg tgacagcatt     420
tcaaaagata gtatccatca gaaagttgag acacctacaa agattcacag aaggcaacta   480
agagagaaaa ggcgtgagat gcgggcaaat gagttagttc agcacaatga tgacacgatt   540
ttgaaactcg aaaatgctgc cattgaacgc tctaagtctg ttgattctgc agtccttggt    600
aaatacagta tttggagaag agaaaatgag aatgacaact ctgattcaaa tatacgcttg    660
atgcgggatc aagtaataat ggctagagtc tatagtggga ttgcaaaatt gaaaaacaag    720
aacgatttgt tacaagaact ccaggcccga cttaaggaca gccaacgggt ttttgggggaa   780
gcaacatctg atgctgatct tcctcggagt gcgcatgaga aactcagagc catgggtcaa   840
gtcttggcta agctaagat gcagttatat gactgcaagc tggttactgg aaagctgaga   900
gcaatgcttc agactgccga cgaacaagtg aggagcttaa agaagcagag tacttttctg   960
gctcagttag cagcaaaaac cattccaaat cctatccatt gcctatcaat gcgcttgact   1020
atcgattact atcttctgtc tccggagaaa agaaaattcc ctcggagtga aacctagaa    1080
aaccctaatc tttatcatta tgccctcttt tccgacaatg tattagctgc atcagtagtt   1140
gttaactcaa ccatcatgaa tgccaaggat ccttctaagc atgtttttca ccttgtcacg    1200
gataaactca atttcggagc aatgaacatg tggttcctcc taaacccacc cggaaaggca    1260
accatacatg tggaaaacgt cgatgagttt aagtggctca attcatctta ctgtcctgtc    1320
cttcgtcagc ttgaatctgc agcaatgaga gagtactatt ttaaagcaga ccatccaact   1380
tcaggctctt cgaatctaaa atacagaaac ccaaagtatc tatccatgtt gaatcacttg    1440
agattctacc tccctgaggt ttatcccaag ctgaacaaaa tcctcttcct ggacgatgac   1500
atcattgttc agaaagactt gactccactc tgggaagtta acctgaacgg caaagtcaac    1560
ggtgcagtcg aaacctgtgg ggaaagtttc cacagattcg acaagtatct caacttttcg   1620
aatcctcaca ttgcgaggaa cttcaatcca atgcttgtg gatgggctta tggaatgaac   1680
atgttcgacc taaaggaatg gaagaagaga gacatcactg gtatataccaa cagtggcaa    1740
aacatgaatg agaacaggac actatggaag ctagggacat gccaccagg attaataaca    1800
ttctacggat taacacatcc cttaaacaag gcgtggcatg tgctgggact tggatataac   1860
ccgagtatcg acaagaagga cattgagaat gcagcagtgg ttcactataa cgggaacatg   1920
aaaccatggt tggagttggc aatgtccaaa tatcggccgt attggaccaa gtacatcaag   1980
tttgatcacc catatcttcg tcgttgcaac cttcatgaat aa                        2022
```

<210> SEQ ID NO 2
<211> LENGTH: 673
<212> TYPE: PRT
<213> ORGANISM: Arabidopsis thaliana

<400> SEQUENCE: 2

```
Met Ala Leu Lys Arg Gly Leu Ser Gly Val Asn Arg Ile Arg Gly Ser
1               5                   10                  15

Gly Gly Gly Ser Arg Ser Val Leu Val Leu Leu Ile Phe Phe Cys Val
            20                  25                  30
```

```
Phe Ala Pro Leu Cys Phe Phe Val Gly Arg Gly Val Tyr Ile Asp Ser
         35                  40                  45

Ser Asn Asp Tyr Ser Ile Val Ser Val Lys Gln Asn Leu Asp Trp Arg
     50                  55                  60

Glu Arg Leu Ala Met Gln Ser Val Arg Ser Leu Phe Ser Lys Glu Ile
 65                  70                  75                  80

Leu Asp Val Ile Ala Thr Ser Thr Ala Asp Leu Gly Pro Leu Ser Leu
                 85                  90                  95

Asp Ser Phe Lys Lys Asn Asn Leu Ser Ala Ser Trp Arg Gly Thr Gly
             100                 105                 110

Val Asp Pro Ser Phe Arg His Ser Glu Asn Pro Ala Thr Pro Asp Val
         115                 120                 125

Lys Ser Asn Asn Leu Asn Glu Lys Arg Asp Ser Ile Ser Lys Asp Ser
     130                 135                 140

Ile His Gln Lys Val Glu Thr Pro Thr Lys Ile His Arg Arg Gln Leu
145                 150                 155                 160

Arg Glu Lys Arg Arg Glu Met Arg Ala Asn Glu Leu Val Gln His Asn
                 165                 170                 175

Asp Asp Thr Ile Leu Lys Leu Glu Asn Ala Ala Ile Glu Arg Ser Lys
             180                 185                 190

Ser Val Asp Ser Ala Val Leu Gly Lys Tyr Ser Ile Trp Arg Arg Glu
         195                 200                 205

Asn Glu Asn Asp Asn Ser Asp Ser Asn Ile Arg Leu Met Arg Asp Gln
     210                 215                 220

Val Ile Met Ala Arg Val Tyr Ser Gly Ile Ala Lys Leu Lys Asn Lys
225                 230                 235                 240

Asn Asp Leu Leu Gln Glu Leu Gln Ala Arg Leu Lys Asp Ser Gln Arg
                 245                 250                 255

Val Leu Gly Glu Ala Thr Ser Asp Ala Asp Leu Pro Arg Ser Ala His
             260                 265                 270

Glu Lys Leu Arg Ala Met Gly Gln Val Leu Ala Lys Ala Lys Met Gln
         275                 280                 285

Leu Tyr Asp Cys Lys Leu Val Thr Gly Lys Leu Arg Ala Met Leu Gln
     290                 295                 300

Thr Ala Asp Glu Gln Val Arg Ser Leu Lys Lys Gln Ser Thr Phe Leu
305                 310                 315                 320

Ala Gln Leu Ala Ala Lys Thr Ile Pro Asn Pro Ile His Cys Leu Ser
                 325                 330                 335

Met Arg Leu Thr Ile Asp Tyr Tyr Leu Leu Ser Pro Glu Lys Arg Lys
             340                 345                 350

Phe Pro Arg Ser Glu Asn Leu Glu Asn Pro Asn Leu Tyr His Tyr Ala
         355                 360                 365

Leu Phe Ser Asp Asn Val Leu Ala Ala Ser Val Val Asn Ser Thr
     370                 375                 380

Ile Met Asn Ala Lys Asp Pro Ser Lys His Val Phe His Leu Val Thr
385                 390                 395                 400

Asp Lys Leu Asn Phe Gly Ala Met Asn Met Trp Phe Leu Leu Asn Pro
                 405                 410                 415

Pro Gly Lys Ala Thr Ile His Val Glu Asn Val Asp Glu Phe Lys Trp
             420                 425                 430

Leu Asn Ser Ser Tyr Cys Pro Val Leu Arg Gln Leu Glu Ser Ala Ala
         435                 440                 445
```

```
Met Arg Glu Tyr Tyr Phe Lys Ala Asp His Pro Thr Ser Gly Ser Ser
    450                 455                 460
Asn Leu Lys Tyr Arg Asn Pro Lys Tyr Leu Ser Met Leu Asn His Leu
465                 470                 475                 480
Arg Phe Tyr Leu Pro Glu Val Tyr Pro Lys Leu Asn Lys Ile Leu Phe
                485                 490                 495
Leu Asp Asp Ile Ile Val Gln Lys Asp Leu Thr Pro Leu Trp Glu
            500                 505                 510
Val Asn Leu Asn Gly Lys Val Asn Gly Ala Val Glu Thr Cys Gly Glu
            515                 520                 525
Ser Phe His Arg Phe Asp Lys Tyr Leu Asn Phe Ser Asn Pro His Ile
    530                 535                 540
Ala Arg Asn Phe Asn Pro Asn Ala Cys Gly Trp Ala Tyr Gly Met Asn
545                 550                 555                 560
Met Phe Asp Leu Lys Glu Trp Lys Lys Arg Asp Ile Thr Gly Ile Tyr
                565                 570                 575
His Lys Trp Gln Asn Met Asn Glu Asn Arg Thr Leu Trp Lys Leu Gly
            580                 585                 590
Thr Leu Pro Pro Gly Leu Ile Thr Phe Tyr Gly Leu Thr His Pro Leu
            595                 600                 605
Asn Lys Ala Trp His Val Leu Gly Leu Gly Tyr Asn Pro Ser Ile Asp
610                 615                 620
Lys Lys Asp Ile Glu Asn Ala Ala Val Val His Tyr Asn Gly Asn Met
625                 630                 635                 640
Lys Pro Trp Leu Glu Leu Ala Met Ser Lys Tyr Arg Pro Tyr Trp Thr
                645                 650                 655
Lys Tyr Ile Lys Phe Asp His Pro Tyr Leu Arg Arg Cys Asn Leu His
            660                 665                 670
Glu

<210> SEQ ID NO 3
<211> LENGTH: 1860
<212> TYPE: DNA
<213> ORGANISM: Arabidopsis thaliana

<400> SEQUENCE: 3
atgaaaggcg gaggcggtgg tggaggaggt ggtggcggag gaaaacgccg gtggaaagtt      60
ctggtgattg gagttttggt tcttgttatt ctttctatgc ttgttcctct tgctttctta     120
ctcggtcttc acaatggctt tcactctcct ggatttgtca ctgttcaacc ggcttcttca     180
tttgagagct ttaccagaat caatgctact aagcatacac agagagatgt atccgaacgg     240
gtcgatgagg ttcttcaaaa aatcaatcca gttcttccca agaaaagcga cataaacgtg     300
ggttccagag atgtgaatgc aacaagcggc actgattcta aaaaagagg attaccagtg     360 tccccaactg ttgttgccaa tccaagccct gcaaataaaa caaatcgga agcctcatat     420 acaggtgttc agaggaaaat agtaagtggt gatgaaactt ggagaacttg tgaagtgaaa     480
tatgggagct actgcctctg gagggaggaa aataaggaac caatgaaaga tgccaaggtg     540
aagcaaatga aggaccagct gtttgtggct agagcatact atcccagtat tgctaaaatg     600
ccttctcaaa gcaagttgac tcgggatatg aaacagaata tccaagagtt tgagcgtatt     660
cttagtgaaa gttctcaaga tgctgacctt ccaccacagg ttgataaaaa gttgcagaag     720
atggaagctg taattgcaaa ggcaaagtct tttccagtcg actgtaacaa tgttgacaag     780
aaattgagac agatccttga tttgactgag gatgaagcta gtttccacat gaaacagagt     840
```

```
gtgttcctct accagcttgc agtacagaca atgcctaaga gtcttcattg cttgtcaatg      900
cgactaactg tggaacattt caagtcagat tcacttgagg atcccattag tgagaaattt      960
tcagatccct cattacttca ctttgttatc atctccgata atatactagc atcgtccgtt     1020
gtgatcaact caacggttgt acatgcaagg acagtaaaa actttgtttt ccatgtactg     1080
acagacgagc agaattactt tgcaatgaaa caatggttta ttaggaatcc ttgcaaacaa     1140
tcaactgttc aagtattgaa cattgaaaaa ctcgagctgg acgattctga tatgaaactg     1200
tctttgtctg cggagttccg tgtttccttc cccagtggtg accttttggc gtctcaacag     1260
aatagaacac actacttatc cctttctct caatctcact atcttcttcc caaattattt     1320
gacaaattgg agaaggttgt gattctggat gatgacgttg tagtccagcg agacttatct     1380
cccctttggg accttgatat ggaagggaaa gtgaatggcg ctgttaagtc gtgcactgtg     1440
agattgggtc agctaaggag tctcaagaga ggaaattttg ataccaatgc ttgtctctgg     1500
atgtctggtt tgaatgtcgt tgatcttgct agatggaggg cattgggtgt ttcagaaacc     1560
tatcaaaaat attataaaga gatgagtagt ggagatgagt cgagcgaagc aattgcattg     1620
caggcaagct tgctcacatt tcaagaccaa gtatatgctc ttgacgacaa atgggctcta     1680
tcagggcttg gttatgacta ctacatcaat gcacaagcca taaaaaacgc agccatattg     1740
cactataacg ggaacatgaa gccgtggctt gagctgggaa tcccaaatta caaaaactat     1800
tggagaaggc atctgagtcg ggaagatcgg ttcttgagtg actgtaacgt gaatccttga     1860
```

<210> SEQ ID NO 4
<211> LENGTH: 619
<212> TYPE: PRT
<213> ORGANISM: Arabidopsis thaliana

<400> SEQUENCE: 4

```
Met Lys Gly Gly Gly Gly Gly Gly Gly Gly Gly Gly Lys Arg
1               5                   10                  15

Arg Trp Lys Val Leu Val Ile Gly Val Leu Val Leu Ile Leu Ser
            20                  25                  30

Met Leu Val Pro Leu Ala Phe Leu Leu Gly Leu His Asn Gly Phe His
        35                  40                  45

Ser Pro Gly Phe Val Thr Val Gln Pro Ala Ser Phe Glu Ser Phe
    50                  55                  60

Thr Arg Ile Asn Ala Thr Lys His Thr Gln Arg Asp Val Ser Glu Arg
65                  70                  75                  80

Val Asp Glu Val Leu Gln Lys Ile Asn Pro Val Leu Pro Lys Lys Ser
                85                  90                  95

Asp Ile Asn Val Gly Ser Arg Asp Val Asn Ala Thr Ser Gly Thr Asp
            100                 105                 110

Ser Lys Lys Arg Gly Leu Pro Val Ser Pro Thr Val Val Ala Asn Pro
        115                 120                 125

Ser Pro Ala Asn Lys Thr Lys Ser Glu Ala Ser Tyr Thr Gly Val Gln
    130                 135                 140

Arg Lys Ile Val Ser Gly Asp Glu Thr Trp Arg Thr Cys Glu Val Lys
145                 150                 155                 160

Tyr Gly Ser Tyr Cys Leu Trp Arg Glu Glu Asn Lys Glu Pro Met Lys
                165                 170                 175

Asp Ala Lys Val Lys Gln Met Lys Asp Gln Leu Phe Val Ala Arg Ala
            180                 185                 190
```

```
Tyr Tyr Pro Ser Ile Ala Lys Met Pro Ser Gln Ser Lys Leu Thr Arg
        195                 200                 205

Asp Met Lys Gln Asn Ile Gln Glu Phe Glu Arg Ile Leu Ser Glu Ser
        210                 215                 220

Ser Gln Asp Ala Asp Leu Pro Pro Gln Val Asp Lys Lys Leu Gln Lys
225                 230                 235                 240

Met Glu Ala Val Ile Ala Lys Ala Lys Ser Phe Pro Val Asp Cys Asn
                245                 250                 255

Asn Val Asp Lys Lys Leu Arg Gln Ile Leu Asp Leu Thr Glu Asp Glu
            260                 265                 270

Ala Ser Phe His Met Lys Gln Ser Val Phe Leu Tyr Gln Leu Ala Val
        275                 280                 285

Gln Thr Met Pro Lys Ser Leu His Cys Leu Ser Met Arg Leu Thr Val
    290                 295                 300

Glu His Phe Lys Ser Asp Ser Leu Glu Asp Pro Ile Ser Glu Lys Phe
305                 310                 315                 320

Ser Asp Pro Ser Leu Leu His Phe Val Ile Ser Asp Asn Ile Leu
                325                 330                 335

Ala Ser Ser Val Val Ile Asn Ser Thr Val Val His Ala Arg Asp Ser
            340                 345                 350

Lys Asn Phe Val Phe His Val Leu Thr Asp Glu Gln Asn Tyr Phe Ala
        355                 360                 365

Met Lys Gln Trp Phe Ile Arg Asn Pro Cys Lys Gln Ser Thr Val Gln
    370                 375                 380

Val Leu Asn Ile Glu Lys Leu Glu Leu Asp Asp Ser Asp Met Lys Leu
385                 390                 395                 400

Ser Leu Ser Ala Glu Phe Arg Val Ser Phe Pro Ser Gly Asp Leu Leu
                405                 410                 415

Ala Ser Gln Gln Asn Arg Thr His Tyr Leu Ser Leu Phe Ser Gln Ser
            420                 425                 430

His Tyr Leu Leu Pro Lys Leu Phe Asp Lys Leu Glu Lys Val Val Ile
        435                 440                 445

Leu Asp Asp Asp Val Val Val Gln Arg Asp Leu Ser Pro Leu Trp Asp
    450                 455                 460

Leu Asp Met Glu Gly Lys Val Asn Gly Ala Val Lys Ser Cys Thr Val
465                 470                 475                 480

Arg Leu Gly Gln Leu Arg Ser Leu Lys Arg Gly Asn Phe Asp Thr Asn
                485                 490                 495

Ala Cys Leu Trp Met Ser Gly Leu Asn Val Val Asp Leu Ala Arg Trp
            500                 505                 510

Arg Ala Leu Gly Val Ser Glu Thr Tyr Gln Lys Tyr Tyr Lys Glu Met
        515                 520                 525

Ser Ser Gly Asp Glu Ser Ser Glu Ala Ile Ala Leu Gln Ala Ser Leu
    530                 535                 540

Leu Thr Phe Gln Asp Gln Val Tyr Ala Leu Asp Asp Lys Trp Ala Leu
545                 550                 555                 560

Ser Gly Leu Gly Tyr Asp Tyr Tyr Ile Asn Ala Gln Ala Ile Lys Asn
                565                 570                 575

Ala Ala Ile Leu His Tyr Asn Gly Asn Met Lys Pro Trp Leu Glu Leu
            580                 585                 590

Gly Ile Pro Asn Tyr Lys Asn Tyr Trp Arg Arg His Leu Ser Arg Glu
        595                 600                 605

Asp Arg Phe Leu Ser Asp Cys Asn Val Asn Pro
```

610        615

<210> SEQ ID NO 5
<211> LENGTH: 1851
<212> TYPE: DNA
<213> ORGANISM: Arabidopsis thaliana

<400> SEQUENCE: 5

| | |
|---|---:|
| atgatggtga agcttcgcaa tcttgttctt ttcttcatgc tcctcaccgt cgttgctcat | 60 |
| atccttctct acaccgatcc cgctgcctcc ttcaagaccc cttttctaa acgcgatttc | 120 |
| ctcgaggacg taaccgcctt gactttcaat tccgatgaga atcgtttgaa tcttcttcct | 180 |
| cgggaatctc ccgctgtgct cagaggagga ctcgtcggtg ctgtctattc cgataagaat | 240 |
| tcacggcggc tagaccaatt gtctgctcga gttctttccg ccaccgacga tgatactcac | 300 |
| tcacatactg acatttccat caaacaagtc actcatgatg cagcctcaga ctcgcatatt | 360 |
| aatagggaaa atatgcatgt tcaattgacc caacaaacct ctgaaaaagt tgatgagcaa | 420 |
| ccagagccta tgcttttgg agctaagaaa gatactggaa acgtgttgat gcctgatgct | 480 |
| caagtgaggc atcttaaaga tcagcttatt agggcaaagg tttatctttc ccttccatct | 540 |
| gcaaaggcca atgctcattt tgtgagagag cttcgactcc gtattaaaga agttcaacgg | 600 |
| gcacttgcag atgcctccaa ggattcggat ctgccaaaga ctgctataga aaagctaaaa | 660 |
| gcaatggagc aaacactggc caaaggcaag cagatccaag atgactgttc tacagtggtc | 720 |
| aagaagctac gtgctatgct ccactccgca gatgagcagc tacgggtcca taagaagcaa | 780 |
| accatgtttt tgactcaatt gactgctaag accattccta aaggacttca ctgccttcct | 840 |
| ctgcgcctca ctacagacta ttatgcttta aattcatctg aacaacaatt tccaaatcag | 900 |
| gagaaactag aagatactca gctgtatcac tatgcccttt tctctgataa tgttttggct | 960 |
| acgtcagttg ttgttaactc taccataacc aatgcaaagc atcccttaaa gcatgtcttc | 1020 |
| cacatcgtca cagacagact caattatgcg gcaatgagga tgtggttcct ggacaatcca | 1080 |
| cctggcaaag ccaccatcca ggttcagaat gttgaagaat tacatggct gaattcaagc | 1140 |
| tacagtcccg ttctcaaaca gcttagttct agatcgatga tagattatta cttcagagcc | 1200 |
| caccatacaa attcagacac caacttgaag ttccggaatc caaaatactt atcgatcctt | 1260 |
| aatcatcttc gttttactt gcctgagatc tttcccaagc tcagcaaagt gctcttcttg | 1320 |
| gatgatgata tagttgtgca gaaggacctt tctggtcttt ggtcagttga tctgaaaggt | 1380 |
| aatgttaacg gtgctgtaga gacgtgtggg gaaagctttc atcgctttga ccgttatctg | 1440 |
| aacttctcaa atccactcat ttccaagaac tttgaccctc gagcttgtgg ttgggcgtat | 1500 |
| ggtatgaatg tctttgatct ggatgaatgg aagaggcaaa acatcacaga agtttatcat | 1560 |
| cgatggcagg atctgaatca agaccgagaa ttgtggaagc tagggacgtt gccgcctggt | 1620 |
| ctaatcacat tttggagacg aacatatccg ctagaccgga atggcacat actagggctt | 1680 |
| ggatacaacc cgagtgtgaa ccaaagggat attgagaggg cagccgtgat acactataat | 1740 |
| ggcaacctca aaccatggct agagattggg attccaagat acagaggctt ctggtcaaag | 1800 |
| catgtagact atgagcacgt ttatctcaga gaatgcaaca tcaatcctta g | 1851 |

<210> SEQ ID NO 6
<211> LENGTH: 616
<212> TYPE: PRT
<213> ORGANISM: Arabidopsis thaliana

<400> SEQUENCE: 6

```
Met Met Val Lys Leu Arg Asn Leu Val Leu Phe Phe Met Leu Leu Thr
1               5                   10                  15

Val Val Ala His Ile Leu Leu Tyr Thr Asp Pro Ala Ala Ser Phe Lys
                20                  25                  30

Thr Pro Phe Ser Lys Arg Asp Phe Leu Glu Asp Val Thr Ala Leu Thr
            35                  40                  45

Phe Asn Ser Asp Glu Asn Arg Leu Asn Leu Leu Pro Arg Glu Ser Pro
        50                  55                  60

Ala Val Leu Arg Gly Gly Leu Gly Ala Val Tyr Ser Asp Lys Asn
65                  70                  75                  80

Ser Arg Arg Leu Asp Gln Leu Ser Ala Arg Val Leu Ser Ala Thr Asp
                85                  90                  95

Asp Asp Thr His Ser His Thr Asp Ile Ser Ile Lys Gln Val Thr His
                100                 105                 110

Asp Ala Ala Ser Asp Ser His Ile Asn Arg Glu Asn Met His Val Gln
                115                 120                 125

Leu Thr Gln Gln Thr Ser Glu Lys Val Asp Glu Gln Pro Glu Pro Asn
130                 135                 140

Ala Phe Gly Ala Lys Lys Asp Thr Gly Asn Val Leu Met Pro Asp Ala
145                 150                 155                 160

Gln Val Arg His Leu Lys Asp Gln Leu Ile Arg Ala Lys Val Tyr Leu
                165                 170                 175

Ser Leu Pro Ser Ala Lys Ala Asn Ala His Phe Val Arg Glu Leu Arg
                180                 185                 190

Leu Arg Ile Lys Glu Val Gln Arg Ala Leu Ala Asp Ala Ser Lys Asp
                195                 200                 205

Ser Asp Leu Pro Lys Thr Ala Ile Glu Lys Leu Lys Ala Met Glu Gln
210                 215                 220

Thr Leu Ala Lys Gly Lys Gln Ile Gln Asp Asp Cys Ser Thr Val Val
225                 230                 235                 240

Lys Lys Leu Arg Ala Met Leu His Ser Ala Asp Glu Gln Leu Arg Val
                245                 250                 255

His Lys Lys Gln Thr Met Phe Leu Thr Gln Leu Thr Ala Lys Thr Ile
                260                 265                 270

Pro Lys Gly Leu His Cys Leu Pro Leu Arg Leu Thr Thr Asp Tyr Tyr
                275                 280                 285

Ala Leu Asn Ser Ser Glu Gln Gln Phe Pro Asn Gln Glu Lys Leu Glu
                290                 295                 300

Asp Thr Gln Leu Tyr His Tyr Ala Leu Phe Ser Asp Asn Val Leu Ala
305                 310                 315                 320

Thr Ser Val Val Val Asn Ser Thr Ile Thr Asn Ala Lys His Pro Leu
                325                 330                 335

Lys His Val Phe His Ile Val Thr Asp Arg Leu Asn Tyr Ala Ala Met
                340                 345                 350

Arg Met Trp Phe Leu Asp Asn Pro Pro Gly Lys Ala Thr Ile Gln Val
                355                 360                 365

Gln Asn Val Glu Glu Phe Thr Trp Leu Asn Ser Ser Tyr Ser Pro Val
                370                 375                 380

Leu Lys Gln Leu Ser Ser Arg Ser Met Ile Asp Tyr Tyr Phe Arg Ala
385                 390                 395                 400

His His Thr Asn Ser Asp Thr Asn Leu Lys Phe Arg Asn Pro Lys Tyr
                405                 410                 415
```

```
Leu Ser Ile Leu Asn His Leu Arg Phe Tyr Leu Pro Glu Ile Phe Pro
        420                 425                 430
Lys Leu Ser Lys Val Leu Phe Leu Asp Asp Ile Val Val Gln Lys
        435                 440                 445
Asp Leu Ser Gly Leu Trp Ser Val Asp Leu Lys Gly Asn Val Asn Gly
        450                 455                 460
Ala Val Glu Thr Cys Gly Glu Ser Phe His Arg Phe Asp Arg Tyr Leu
465                 470                 475                 480
Asn Phe Ser Asn Pro Leu Ile Ser Lys Asn Phe Asp Pro Arg Ala Cys
                485                 490                 495
Gly Trp Ala Tyr Gly Met Asn Val Phe Asp Leu Asp Glu Trp Lys Arg
                500                 505                 510
Gln Asn Ile Thr Glu Val Tyr His Arg Trp Gln Asp Leu Asn Gln Asp
        515                 520                 525
Arg Glu Leu Trp Lys Leu Gly Thr Leu Pro Pro Gly Leu Ile Thr Phe
        530                 535                 540
Trp Arg Arg Thr Tyr Pro Leu Asp Arg Lys Trp His Ile Leu Gly Leu
545                 550                 555                 560
Gly Tyr Asn Pro Ser Val Asn Gln Arg Asp Ile Glu Arg Ala Ala Val
                565                 570                 575
Ile His Tyr Asn Gly Asn Leu Lys Pro Trp Leu Glu Ile Gly Ile Pro
                580                 585                 590
Arg Tyr Arg Gly Phe Trp Ser Lys His Val Asp Tyr Glu His Val Tyr
        595                 600                 605
Leu Arg Glu Cys Asn Ile Asn Pro
        610                 615

<210> SEQ ID NO 7
<211> LENGTH: 1770
<212> TYPE: DNA
<213> ORGANISM: Arabidopsis thaliana

<400> SEQUENCE: 7
atgaaacaaa ttcgtcgatg gcagaggatt ttgatcctcg ctctgctatc gatatcagta      60
ttcgctccgc ttattttcgt atcgaatcgg cttaagagca tcactcccgt tggtcgtaga     120
gaatttattg aagagttatc caaaattaga ttcacgacaa atgaccttag acttagcgct     180
attgaacatg aggatggaga aggcttgaag gggccaaggc tcattctctt caaggatggg     240
gagtttaatt cgtctgctga aagtgatggt ggtaatactt acaaaaacag gaagaacaa     300 gtgattgttt cacagaagat gacagttagc tctgatgaaa agggtcaaat tctaccaaca     360
gtcaaccaac ttgctaataa aacggatttc aagccccctt tatctaaggg tgaaaagaac     420
acaagggttc agcccgacag agcaacagat gtgaaaacga aggagatcag agacaaaatt     480
attcaagcta aagcctacct gaatttcgct ccacctggaa gtaactctca agttgtgaag     540
gagttgagag gtcggctgaa agagctggaa cggtctgttg gtgatgcaac aaaggacaag     600
gacttatcaa agggcgctct ccgcagggtg aagcccatgg aaaatgtgtt atataaggct     660
agtcgtgtct ttaacaattg ccctgccatc gctaccaaac tccgtgccat gaattataac     720
acagaagaac aagttcaggc gcagaaaaat caagcagcgt atctaatgca gcttgcagca     780
aggaccaccc caaaagggct tcactgtctc tcaatgcggc tgacatcaga atactttca     840 ctggatcctg aaaaaggca gatgcctaac cagcaaaatt attttgacgc taatttcaat     900
cattatgttg tcttctctga caatgttttg gcttcttcag tcgttgttaa ctctacgata     960
```

```
tcttcatcaa aggagccaga aagaatagtc ttccatgtcg tgactgattc acttaattac    1020
ccagcaatct caatgtggtt tctgctaaac attcaaagta aagctactat ccaaatccta    1080
aacattgatg atatggatgt cctgcctaga gattatgatc aattactgat gaagcaaaac    1140
tctaatgacc caagattcat ttctacactc aatcacgcac gcttctatct cccggatata    1200
ttcccgggtt tgaacaagat ggtactcttg gaccatgatg tagttgttca aagagattta    1260
agtagactgt ggagcattga tatgaaagga aaggtggttg gagctgtaga gacttgtctt    1320
gaaggtgaat cttcatttcg atcaatgagc acatttatta atttctcaga cacatgggtc    1380
gctgggaaat ttagtcctag agcttgcaca tgggctttcg gatgaatct aattgatctc      1440 gaagaatgga gaatacggaa gttgacttct acatacataa aatacttcaa cctgggaaca    1500
aagagaccat tgtggaaagc tgggagctta ccaataggtt ggttgacttt ctataggcaa    1560
acattagcat ggacaagag atggcatgtg atggggttag gtcgcgaatc aggagtcaaa     1620
gcggttgaca tcgaacaagc ggcagttata cactacgatg gggtcatgaa gccgtggttg    1680
gacattggaa aagagaatta caaacgttac tggaacatac acgtcccta ccatcacacc      1740 tacttgcaac agtgcaatct tcaagcttga                                      1770

<210> SEQ ID NO 8
<211> LENGTH: 589
<212> TYPE: PRT
<213> ORGANISM: Arabidospsis thaliana

<400> SEQUENCE: 8

Met Lys Gln Ile Arg Arg Trp Gln Arg Ile Leu Ile Leu Ala Leu Leu
1               5                   10                  15

Ser Ile Ser Val Phe Ala Pro Leu Ile Phe Val Ser Asn Arg Leu Lys
            20                  25                  30

Ser Ile Thr Pro Val Gly Arg Arg Glu Phe Ile Glu Glu Leu Ser Lys
        35                  40                  45

Ile Arg Phe Thr Thr Asn Asp Leu Arg Leu Ser Ala Ile Glu His Glu
    50                  55                  60

Asp Gly Glu Gly Leu Lys Gly Pro Arg Leu Ile Leu Phe Lys Asp Gly
65                  70                  75                  80

Glu Phe Asn Ser Ser Ala Glu Ser Asp Gly Gly Asn Thr Tyr Lys Asn
                85                  90                  95

Arg Glu Glu Gln Val Ile Val Ser Gln Lys Met Thr Val Ser Ser Asp
            100                 105                 110

Glu Lys Gly Gln Ile Leu Pro Thr Val Asn Gln Leu Ala Asn Lys Thr
        115                 120                 125

Asp Phe Lys Pro Pro Leu Ser Lys Gly Glu Lys Asn Thr Arg Val Gln
    130                 135                 140

Pro Asp Arg Ala Thr Asp Val Lys Thr Lys Glu Ile Arg Asp Lys Ile
145                 150                 155                 160

Ile Gln Ala Lys Ala Tyr Leu Asn Phe Ala Pro Gly Ser Asn Ser
                165                 170                 175

Gln Val Val Lys Glu Leu Arg Gly Leu Lys Glu Leu Glu Arg Ser
            180                 185                 190

Val Gly Asp Ala Thr Lys Asp Lys Asp Leu Ser Lys Gly Ala Leu Arg
        195                 200                 205

Arg Val Lys Pro Met Glu Asn Val Leu Tyr Lys Ala Ser Arg Val Phe
    210                 215                 220

Asn Asn Cys Pro Ala Ile Ala Thr Lys Leu Arg Ala Met Asn Tyr Asn
```

```
                225                 230                 235                 240
Thr Glu Glu Gln Val Gln Ala Gln Lys Asn Gln Ala Ala Tyr Leu Met
                    245                 250                 255
Gln Leu Ala Ala Arg Thr Thr Pro Lys Gly Leu His Cys Leu Ser Met
                260                 265                 270
Arg Leu Thr Ser Glu Tyr Phe Ser Leu Asp Pro Glu Lys Arg Gln Met
            275                 280                 285
Pro Asn Gln Gln Asn Tyr Phe Asp Ala Asn Phe Asn His Tyr Val Val
        290                 295                 300
Phe Ser Asp Asn Val Leu Ala Ser Ser Val Val Asn Ser Thr Ile
305                 310                 315                 320
Ser Ser Ser Lys Glu Pro Glu Arg Ile Val Phe His Val Val Thr Asp
                325                 330                 335
Ser Leu Asn Tyr Pro Ala Ile Ser Met Trp Phe Leu Leu Asn Ile Gln
                340                 345                 350
Ser Lys Ala Thr Ile Gln Ile Leu Asn Ile Asp Asp Met Asp Val Leu
                355                 360                 365
Pro Arg Asp Tyr Asp Gln Leu Leu Met Lys Gln Asn Ser Asn Asp Pro
        370                 375                 380
Arg Phe Ile Ser Thr Leu Asn His Ala Arg Phe Tyr Leu Pro Asp Ile
385                 390                 395                 400
Phe Pro Gly Leu Asn Lys Met Val Leu Leu Asp His Asp Val Val Val
                405                 410                 415
Gln Arg Asp Leu Ser Arg Leu Trp Ser Ile Asp Met Lys Gly Lys Val
                420                 425                 430
Val Gly Ala Val Glu Thr Cys Leu Glu Gly Glu Ser Ser Phe Arg Ser
                435                 440                 445
Met Ser Thr Phe Ile Asn Phe Ser Asp Thr Trp Val Ala Gly Lys Phe
        450                 455                 460
Ser Pro Arg Ala Cys Thr Trp Ala Phe Gly Met Asn Leu Ile Asp Leu
465                 470                 475                 480
Glu Glu Trp Arg Ile Arg Lys Leu Thr Ser Thr Tyr Ile Lys Tyr Phe
                485                 490                 495
Asn Leu Gly Thr Lys Arg Pro Leu Trp Lys Ala Gly Ser Leu Pro Ile
                500                 505                 510
Gly Trp Leu Thr Phe Tyr Arg Gln Thr Leu Ala Leu Asp Lys Arg Trp
            515                 520                 525
His Val Met Gly Leu Gly Arg Glu Ser Gly Val Lys Ala Val Asp Ile
        530                 535                 540
Glu Gln Ala Ala Val Ile His Tyr Asp Gly Val Met Lys Pro Trp Leu
545                 550                 555                 560
Asp Ile Gly Lys Glu Asn Tyr Lys Arg Tyr Trp Asn Ile His Val Pro
                565                 570                 575
Tyr His His Thr Tyr Leu Gln Gln Cys Asn Leu Gln Ala
                580                 585

<210> SEQ ID NO 9
<211> LENGTH: 1614
<212> TYPE: DNA
<213> ORGANISM: Arabidopsis thaliana

<400> SEQUENCE: 9
atgaggcggt ggccggtgga tcaccggcgg cgaggtagaa ggagattgtc gagttggata     60
tggtttctcc ttggttcttt ctctgtcgct ggtttagttc tcttcatcgt tcagcattat    120
```

-continued

```
caccatcaac aagatccatc ccagctttta cttgagagag acacgagaac cgaaatggta    180
tctcctcccc atttaaactt cacggaagag gtcacaagtg cttcctcctt ctctaggcag    240
ttagcagagc aaatgacact tgccaaagct tatgtgttta tagctaaaga gcataataat    300
cttcatttag cttgggaatt gagttctaag atcagaagtt gtcagctttt gctttccaaa    360
gcagctatga gaggacaacc tatttcgttt gatgaggcta aaccgattat tactggtcta    420
tcagctctta tctacaaggc tcaagatgca cattatgata ttgccaccac tatgatgacc    480
atgaaatctc acatccaagc acttgaagag cgtgcaaatg cagctactgt tcagaccaca    540
atatttgggc aattggttgc tgaggcatta ccaaagagcc tccactgttt gacgataaag    600
ctcacatctg attgggtaac agagccatct cgccatgaac tggcagatga aacagaaac     660 tcacctagac ttgtcgacaa caacctctac cacttctgca tcttctcgga caacgtgatt    720
gccacctcgg ttgttgttaa ttcaactgtc tcgaatgctg atcatccaaa gcagcttgtt    780
ttccacatag tgacgaatcg agtgagctac aaagctatgc aggcctggtt tctaagtaat    840
gacttcaagg gctcagcaat agagatcagg agcgtagagg agttttcttg gttgaatgct    900
tcatattctc ctgttgttaa gcaactgctg acacagatg caagagctta ctatttcggg      960
gaacagacaa gtcaagatac gatttccgag ccaaaagtga ggaacccaaa gtacttgtca   1020
ttactgaacc atctcagatt ctacattccg gagatctatc cacagctaga aagattgtt    1080 ttcctagacg atgatgttgt tgttcagaaa gatttgactc cactcttctc cttggatctg   1140
catggaaacg tcaatggagc tgtggaaaca tgtcttgaag cctttcaccg atattacaag   1200
tatctaaatt tctcgaaccc actcatcagc tcaaagttcg acccacaagc atgtggatgg   1260
gcttttggta tgaacgtttt tgatctgatc gcttggagga atgcaaacgt gactgctcgg   1320
taccattact ggcaagatca gaacagagaa cgaacgcttt ggaaactcgg gacactccct   1380
ccaggtctac tatctttcta tggtctcaca gagccactgg acagaagatg gcatgtcttg   1440
ggtttaggtt acgatgtgaa catcgataac cgtctgatcg aaacagcagc tgtgattcac   1500
tataatggta acatgaagcc ttggctaaag ctggctattg gtaggtataa acctttctgg   1560
ttaaagtttt tgaactcgag ccatccttat ttacaagatt gtgtcacagc ttaa         1614
```

<210> SEQ ID NO 10
<211> LENGTH: 537
<212> TYPE: PRT
<213> ORGANISM: Arabidopsis thaliana

<400> SEQUENCE: 10

```
Met Arg Arg Trp Pro Val Asp His Arg Arg Gly Arg Arg Arg Leu
1               5                   10                  15

Ser Ser Trp Ile Trp Phe Leu Leu Gly Ser Phe Ser Val Ala Gly Leu
            20                  25                  30

Val Leu Phe Ile Val Gln His Tyr His His Gln Gln Asp Pro Ser Gln
        35                  40                  45

Leu Leu Leu Glu Arg Asp Thr Arg Thr Glu Met Val Ser Pro Pro His
    50                  55                  60

Leu Asn Phe Thr Glu Glu Val Thr Ser Ala Ser Ser Phe Ser Arg Gln
65                  70                  75                  80

Leu Ala Glu Gln Met Thr Leu Ala Lys Ala Tyr Val Phe Ile Ala Lys
                85                  90                  95

Glu His Asn Asn Leu His Leu Ala Trp Glu Leu Ser Ser Lys Ile Arg
            100                 105                 110
```

```
Ser Cys Gln Leu Leu Leu Ser Lys Ala Ala Met Arg Gly Gln Pro Ile
        115                 120                 125

Ser Phe Asp Glu Ala Lys Pro Ile Ile Thr Gly Leu Ser Ala Leu Ile
    130                 135                 140

Tyr Lys Ala Gln Asp Ala His Tyr Asp Ile Ala Thr Thr Met Met Thr
145                 150                 155                 160

Met Lys Ser His Ile Gln Ala Leu Glu Arg Ala Asn Ala Ala Thr
                165                 170                 175

Val Gln Thr Thr Ile Phe Gly Gln Leu Val Ala Glu Ala Leu Pro Lys
            180                 185                 190

Ser Leu His Cys Leu Thr Ile Lys Leu Thr Ser Asp Trp Val Thr Glu
        195                 200                 205

Pro Ser Arg His Glu Leu Ala Asp Glu Asn Arg Asn Ser Pro Arg Leu
        210                 215                 220

Val Asp Asn Asn Leu Tyr His Phe Cys Ile Phe Ser Asp Asn Val Ile
225                 230                 235                 240

Ala Thr Ser Val Val Asn Ser Thr Val Ser Asn Ala Asp His Pro
            245                 250                 255

Lys Gln Leu Val Phe His Ile Val Thr Asn Arg Val Ser Tyr Lys Ala
        260                 265                 270

Met Gln Ala Trp Phe Leu Ser Asn Asp Phe Lys Gly Ser Ala Ile Glu
        275                 280                 285

Ile Arg Ser Val Glu Glu Phe Ser Trp Leu Asn Ala Ser Tyr Ser Pro
        290                 295                 300

Val Val Lys Gln Leu Leu Asp Thr Asp Ala Arg Ala Tyr Tyr Phe Gly
305                 310                 315                 320

Glu Gln Thr Ser Gln Asp Thr Ile Ser Glu Pro Lys Val Arg Asn Pro
                325                 330                 335

Lys Tyr Leu Ser Leu Leu Asn His Leu Arg Phe Tyr Ile Pro Glu Ile
            340                 345                 350

Tyr Pro Gln Leu Glu Lys Ile Val Phe Leu Asp Asp Asp Val Val Val
        355                 360                 365

Gln Lys Asp Leu Thr Pro Leu Phe Ser Leu Asp Leu His Gly Asn Val
        370                 375                 380

Asn Gly Ala Val Glu Thr Cys Leu Glu Ala Phe His Arg Tyr Tyr Lys
385                 390                 395                 400

Tyr Leu Asn Phe Ser Asn Pro Leu Ile Ser Ser Lys Phe Asp Pro Gln
                405                 410                 415

Ala Cys Gly Trp Ala Phe Gly Met Asn Val Phe Asp Leu Ile Ala Trp
            420                 425                 430

Arg Asn Ala Asn Val Thr Ala Arg Tyr His Tyr Trp Gln Asp Gln Asn
        435                 440                 445

Arg Glu Arg Thr Leu Trp Lys Leu Gly Thr Leu Pro Pro Gly Leu Leu
        450                 455                 460

Ser Phe Tyr Gly Leu Thr Glu Pro Leu Asp Arg Arg Trp His Val Leu
465                 470                 475                 480

Gly Leu Gly Tyr Asp Val Asn Ile Asp Asn Arg Leu Ile Glu Thr Ala
                485                 490                 495

Ala Val Ile His Tyr Asn Gly Asn Met Lys Pro Trp Leu Lys Leu Ala
            500                 505                 510

Ile Gly Arg Tyr Lys Pro Phe Trp Leu Lys Phe Leu Asn Ser Ser His
        515                 520                 525
```

Pro Tyr Leu Gln Asp Cys Val Thr Ala
    530             535

<210> SEQ ID NO 11
<211> LENGTH: 1611
<212> TYPE: DNA
<213> ORGANISM: Arabidopsis thaliana

<400> SEQUENCE: 11

| | | |
|---|---|---|
| atgagaagga gaggagggga tagtttccgg agagctggac ggaggaagat ctcgaatgtg | 60 |
| gtatggtggg ttctctctgg tattgccctc ctgctcttct ttctcattct ctccaaagct | 120 |
| ggtcatattg aacctagacc ctctattcct aagcgacgtt accgtaatga caaatttgta | 180 |
| gagggtatga atatgactga ggaaatgttg agtcctactt ccgttgctcg tcaagttaat | 240 |
| gatcagattg ctcttgctaa agcttttgtt gtcattgcta agaaagtaa gaatcttcag | 300 |
| tttgcttggg acttaagtgc tcagatccgt aactctcagt tgcttttatc gagtgctgct | 360 |
| actaggagaa gtcccttgac tgtcttggaa tctgagtcta ctattcgtga catggctgtt | 420 |
| ttgttatatc aagctcagca gcttcactat gatagtgcta ctatgattat gaggcttaag | 480 |
| gcctcgattc aggctcttga agaacaaatg agttccgtta gcgagaagag ttccaagtat | 540 |
| ggacagattg ctgctgagga gtgcctaag agtctttact gtcttggtgt tcgtctcact | 600 |
| accgaatggt ttcagaattt agacttacag agaactctta aggaaggag tcgtgttgat | 660 |
| tcgaaactca cggataacag tctctaccat ttctgtgtgt tttccgataa cattattgct | 720 |
| acttctgttg tggttaattc tactgctctc aattccaagg cccctgagaa agttgtgttt | 780 |
| catcttgtga ctaatgagat caactatgct gcaatgaagg cttggttcgc cattaatatg | 840 |
| gacaacctca gaggagtcac tgtggaggtt cagaagttcg aggatttctc atggctgaat | 900 |
| gcttcctatg ttccggtcct caagcagctg caagactctg atacgcaaag ctattatttc | 960 |
| tctggacaca cgatgatgg gcgcactcca atcaaattca ggaaccccaa gtatctttcc | 1020 |
| atgctcaacc atcttaggtt ctacatccct gaagtgtttc ctgcgctgaa gaaggtggtc | 1080 |
| tttcttgatg atgatgttgt agttcagaag gatctttcat ctctcttttc gatcgattta | 1140 |
| aacaaaaatg tgaacggggc tgttgagacc tgcatggaga ccttccaccg ctaccacaag | 1200 |
| tacttgaact attctcatcc tctcatacgc tcccactttg atccagatgc gtgtgggtgg | 1260 |
| gcgtttggaa tgaacgtctt tgatttagtt gagtggagga agagaaatgt gaccggcata | 1320 |
| taccactact ggcaagaaaa aaacgtggac cggaccttat ggaaactggg aacactacct | 1380 |
| ccaggacttc tgacatttta cgggttaaca gaggcactag aggcgtcctg gcatatcctg | 1440 |
| ggattgggat acacgaatgt ggatgctcgt gtgatagaga aaggagctgt tcttcacttc | 1500 |
| aatgggaact taaagccatg gttgaagatc gggatagaga agtacaaacc tttgtgggag | 1560 |
| agatacgttg attacacttc tccttttatg caacaatgca attttcattg a | 1611 |

<210> SEQ ID NO 12
<211> LENGTH: 536
<212> TYPE: PRT
<213> ORGANISM: Arabidopsis thaliana

<400> SEQUENCE: 12

Met Arg Arg Arg Gly Gly Asp Ser Phe Arg Arg Ala Gly Arg Arg Lys
1               5                   10                  15

Ile Ser Asn Val Val Trp Trp Val Leu Ser Gly Ile Ala Leu Leu Leu
            20                  25                  30

```
Phe Phe Leu Ile Leu Ser Lys Ala Gly His Ile Glu Pro Arg Pro Ser
            35                  40                  45

Ile Pro Lys Arg Arg Tyr Arg Asn Asp Lys Phe Val Glu Gly Met Asn
        50                  55                  60

Met Thr Glu Glu Met Leu Ser Pro Thr Ser Val Ala Arg Gln Val Asn
 65                  70                  75                  80

Asp Gln Ile Ala Leu Ala Lys Ala Phe Val Ile Ala Lys Glu Ser
                85                  90                  95

Lys Asn Leu Gln Phe Ala Trp Asp Leu Ser Ala Gln Ile Arg Asn Ser
                100                 105                 110

Gln Leu Leu Leu Ser Ser Ala Ala Thr Arg Arg Ser Pro Leu Thr Val
            115                 120                 125

Leu Glu Ser Glu Ser Thr Ile Arg Asp Met Ala Val Leu Leu Tyr Gln
            130                 135                 140

Ala Gln Gln Leu His Tyr Asp Ser Ala Thr Met Ile Met Arg Leu Lys
145                 150                 155                 160

Ala Ser Ile Gln Ala Leu Glu Glu Gln Met Ser Ser Val Ser Glu Lys
                165                 170                 175

Ser Ser Lys Tyr Gly Gln Ile Ala Ala Glu Val Pro Lys Ser Leu
            180                 185                 190

Tyr Cys Leu Gly Val Arg Leu Thr Thr Glu Trp Phe Gln Asn Leu Asp
        195                 200                 205

Leu Gln Arg Thr Leu Lys Glu Arg Ser Arg Val Asp Ser Lys Leu Thr
            210                 215                 220

Asp Asn Ser Leu Tyr His Phe Cys Val Phe Ser Asp Asn Ile Ile Ala
225                 230                 235                 240

Thr Ser Val Val Val Asn Ser Thr Ala Leu Asn Ser Lys Ala Pro Glu
                245                 250                 255

Lys Val Val Phe His Leu Val Thr Asn Glu Ile Asn Tyr Ala Ala Met
            260                 265                 270

Lys Ala Trp Phe Ala Ile Asn Met Asp Asn Leu Arg Gly Val Thr Val
        275                 280                 285

Glu Val Gln Lys Phe Glu Asp Phe Ser Trp Leu Asn Ala Ser Tyr Val
    290                 295                 300

Pro Val Leu Lys Gln Leu Gln Asp Ser Asp Thr Gln Ser Tyr Tyr Phe
305                 310                 315                 320

Ser Gly His Asn Asp Asp Gly Arg Thr Pro Ile Lys Phe Arg Asn Pro
                325                 330                 335

Lys Tyr Leu Ser Met Leu Asn His Leu Arg Phe Tyr Ile Pro Glu Val
            340                 345                 350

Phe Pro Ala Leu Lys Lys Val Val Phe Leu Asp Asp Val Val Val
        355                 360                 365

Gln Lys Asp Leu Ser Ser Leu Phe Ser Ile Asp Leu Asn Lys Asn Val
    370                 375                 380

Asn Gly Ala Val Glu Thr Cys Met Glu Thr Phe His Arg Tyr His Lys
385                 390                 395                 400

Tyr Leu Asn Tyr Ser His Pro Leu Ile Arg Ser His Phe Asp Pro Asp
                405                 410                 415

Ala Cys Gly Trp Ala Phe Gly Met Asn Val Phe Asp Leu Val Glu Trp
            420                 425                 430

Arg Lys Arg Asn Val Thr Gly Ile Tyr His Tyr Trp Gln Glu Lys Asn
        435                 440                 445

Val Asp Arg Thr Leu Trp Lys Leu Gly Thr Leu Pro Pro Gly Leu Leu
```

|       |       |       |       | 450   |       |       |       |       | 455   |       |       |       |       | 460   |       |
|-------|-------|-------|-------|-------|-------|-------|-------|-------|-------|-------|-------|-------|-------|-------|-------|

Thr Phe Tyr Gly Leu Thr Glu Ala Leu Glu Ala Ser Trp His Ile Leu
465                 470                 475                 480

Gly Leu Gly Tyr Thr Asn Val Asp Ala Arg Val Ile Glu Lys Gly Ala
            485                 490                 495

Val Leu His Phe Asn Gly Asn Leu Lys Pro Trp Leu Lys Ile Gly Ile
        500                 505                 510

Glu Lys Tyr Lys Pro Leu Trp Glu Arg Tyr Val Asp Tyr Thr Ser Pro
    515                 520                 525

Phe Met Gln Gln Cys Asn Phe His
    530                 535

<210> SEQ ID NO 13
<211> LENGTH: 1833
<212> TYPE: DNA
<213> ORGANISM: Arabidopsis thaliana

<400> SEQUENCE: 13

```
atgaatcaag ttcgtcgttg gcagaggatt ctgatcctct cgctgctatt gttatctgtt      60
ttagctccga ttgttttcgt ttcgaatcgg ctcaagagca tcacttccgt cgatagagga     120
gaattcattg aagaattatc cgacattaca gataagaccg aggatgaact tagacttact     180
gctattgaac aggacgaaga aggcttgaag gagcctaaac gtattctgca ggatcgagat     240
tttaattctg tggttttgtc aaattcctct gataaaagta atgatactgt gcagtctaat     300
gagggagacc aaaaaaactt tctctcagaa gttgataagg gaaataatca aaaccaaag      360 gaggaacaag cagtttcaca gaaaaccaca gtaagctcga atgcggaggt gaaaatttca     420
gcaagagata ttcaacttaa tcataaaacg gaattccgac cccttcaag  taagagtgaa     480 aagaatacaa gggttcaact tgaaagagca acagatgaga gggtaaagga gatcagagac     540
aaaattatcc aagcgaaagc ctatctgaat ttggccctac ctgggaataa ctcccaaatc     600
gtaaaggagt tgagagttcg aacgaaagag ctggaacggg ctactggtga tactaccaag     660
gataaatatt tgccaaagag ctctcctaac agattgaagg ccatggaagt tgcgttatac     720
aaggtcagcc gtgcctttca caactgccct gccattgcta ccaaactcca agccatgact     780
tataaaaccg aagaacaagc tcgggcgcag aagaaacaag cagcatattt aatgcagctt     840
gcagcaagga ctaccccaaa agggcttcat tgtctctcaa tgcggttgac aacagaatat     900
tttaccctgg atcacgaaaa aaggcagctt ttgcaacaaa gttataatga tcctgatctc     960
taccattacg tagtcttctc tgacaatgtt ttggcctctt cggttgttgt taactctaca    1020
atctcctcat caaggaacc ggataaaata gtattccatg tggtgacaga ttcactcaat    1080
tacccagcaa tctcaatgtg ttttttacta aacccaagtg gcagagcttc aatccaaatc    1140
ctaaacattg atgaaatgaa tgtcctgcca ttgtaccatg ctgaattgct gatgaagcaa    1200
aattcaagtg acccaagaat catttcagcg ctcaaccatg cacgcttcta tctcccagat    1260
atcttcccag gtctaaacaa gatcgtactc ttcgatcatg atgtagtagt gcaaagggat    1320
ctaactagac tgtggagcct tgatatgacg gggaaagttg ttggagctgt agagacttgt    1380
cttgaaggtg atccttcata tcgttcgatg gactcattca ttaatttctc agatgcatgg    1440
gtttctcaga aatttgatcc caaggcttgc acttgggcat tcgggatgaa tctatttgat    1500
ctcgaagaat ggagaagaca ggagttgact tctgtatacc tgaaatactt cgacctggga    1560
gtaaaaggac atctgtggaa agcagggga ttgccagtag gttggttgac ttttttcggg    1620
```

```
caaacgtttc cgttggaaaa gagatggaac gtgggtgggt taggtcacga atcaggactc    1680
agggcaagcg acatcgaaca agcagcggtt atacactacg acgggatcat gaaaccatgg    1740
ctggacatcg gtatagacaa gtacaagcgc tactggaaca tacatgtacc ttaccatcac    1800
cctcacttac aacggtgcaa cattcacgat tga                                 1833
```

<210> SEQ ID NO 14
<211> LENGTH: 610
<212> TYPE: PRT
<213> ORGANISM: Arabidopsis thaliana

<400> SEQUENCE: 14

```
Met Asn Gln Val Arg Arg Trp Gln Arg Ile Leu Ile Leu Ser Leu Leu
1               5                   10                  15

Leu Leu Ser Val Leu Ala Pro Ile Val Phe Val Ser Asn Arg Leu Lys
            20                  25                  30

Ser Ile Thr Ser Val Asp Arg Gly Glu Phe Ile Glu Glu Leu Ser Asp
        35                  40                  45

Ile Thr Asp Lys Thr Glu Asp Glu Leu Arg Leu Thr Ala Ile Glu Gln
    50                  55                  60

Asp Glu Glu Gly Leu Lys Glu Pro Lys Arg Ile Leu Gln Asp Arg Asp
65                  70                  75                  80

Phe Asn Ser Val Val Leu Ser Asn Ser Ser Asp Lys Ser Asn Asp Thr
                85                  90                  95

Val Gln Ser Asn Glu Gly Asp Gln Lys Asn Phe Leu Ser Glu Val Asp
            100                 105                 110

Lys Gly Asn Asn His Lys Pro Lys Glu Glu Gln Ala Val Ser Gln Lys
        115                 120                 125

Thr Thr Val Ser Ser Asn Ala Glu Val Lys Ile Ser Ala Arg Asp Ile
    130                 135                 140

Gln Leu Asn His Lys Thr Glu Phe Arg Pro Ser Ser Lys Ser Glu
145                 150                 155                 160

Lys Asn Thr Arg Val Gln Leu Glu Arg Ala Thr Asp Glu Arg Val Lys
                165                 170                 175

Glu Ile Arg Asp Lys Ile Ile Gln Ala Lys Ala Tyr Leu Asn Leu Ala
            180                 185                 190

Leu Pro Gly Asn Asn Ser Gln Ile Val Lys Glu Leu Arg Val Arg Thr
        195                 200                 205

Lys Glu Leu Glu Arg Ala Thr Gly Asp Thr Thr Lys Asp Lys Tyr Leu
    210                 215                 220

Pro Lys Ser Ser Pro Asn Arg Leu Lys Ala Met Glu Val Ala Leu Tyr
225                 230                 235                 240

Lys Val Ser Arg Ala Phe His Asn Cys Pro Ala Ile Ala Thr Lys Leu
                245                 250                 255

Gln Ala Met Thr Tyr Lys Thr Glu Glu Gln Ala Arg Ala Gln Lys Lys
            260                 265                 270

Gln Ala Ala Tyr Leu Met Gln Leu Ala Ala Arg Thr Thr Pro Lys Gly
        275                 280                 285

Leu His Cys Leu Ser Met Arg Leu Thr Thr Glu Tyr Phe Thr Leu Asp
    290                 295                 300

His Glu Lys Arg Gln Leu Leu Gln Gln Ser Tyr Asn Asp Pro Asp Leu
305                 310                 315                 320

Tyr His Tyr Val Val Phe Ser Asp Asn Val Leu Ala Ser Ser Val Val
                325                 330                 335
```

```
Val Asn Ser Thr Ile Ser Ser Lys Glu Pro Asp Lys Ile Val Phe
            340                 345                 350
His Val Val Thr Asp Ser Leu Asn Tyr Pro Ala Ile Ser Met Trp Phe
            355                 360                 365
Leu Leu Asn Pro Ser Gly Arg Ala Ser Ile Gln Ile Leu Asn Ile Asp
            370                 375                 380
Glu Met Asn Val Leu Pro Leu Tyr His Ala Glu Leu Leu Met Lys Gln
385                 390                 395                 400
Asn Ser Ser Asp Pro Arg Ile Ile Ser Ala Leu Asn His Ala Arg Phe
            405                 410                 415
Tyr Leu Pro Asp Ile Phe Pro Gly Leu Asn Lys Ile Val Leu Phe Asp
            420                 425                 430
His Asp Val Val Gln Arg Asp Leu Thr Arg Leu Trp Ser Leu Asp
            435                 440                 445
Met Thr Gly Lys Val Val Gly Ala Val Glu Thr Cys Leu Glu Gly Asp
            450                 455                 460
Pro Ser Tyr Arg Ser Met Asp Ser Phe Ile Asn Phe Ser Asp Ala Trp
465                 470                 475                 480
Val Ser Gln Lys Phe Asp Pro Lys Ala Cys Thr Trp Ala Phe Gly Met
            485                 490                 495
Asn Leu Phe Asp Leu Glu Glu Trp Arg Arg Gln Glu Leu Thr Ser Val
            500                 505                 510
Tyr Leu Lys Tyr Phe Asp Leu Gly Val Lys Gly His Leu Trp Lys Ala
            515                 520                 525
Gly Gly Leu Pro Val Gly Trp Leu Thr Phe Phe Gly Gln Thr Phe Pro
            530                 535                 540
Leu Glu Lys Arg Trp Asn Val Gly Gly Leu Gly His Glu Ser Gly Leu
545                 550                 555                 560
Arg Ala Ser Asp Ile Glu Gln Ala Ala Val Ile His Tyr Asp Gly Ile
            565                 570                 575
Met Lys Pro Trp Leu Asp Ile Gly Ile Asp Lys Tyr Lys Arg Tyr Trp
            580                 585                 590
Asn Ile His Val Pro Tyr His His Pro His Leu Gln Arg Cys Asn Ile
            595                 600                 605
His Asp
    610

<210> SEQ ID NO 15
<211> LENGTH: 1587
<212> TYPE: DNA
<213> ORGANISM: Arabidopsis thaliana

<400> SEQUENCE: 15
atgactgatg cttgttgttt gaagggaaac gaggacaaaa tggttcctcg ttttggtcat      60
ggaacctgga taggaaaagc atttaatgat acaccagaga tgttgcatga aggagtctg     120 agacaggaaa aaagattgga aagggctaat gagctgatga atgatgatag tctgcaaaag     180
cttgagacgg cagccatggc acgttccaga tctgtcgatt ctgcaccact aggaaactac     240
accatttgga aaatgaata ccggaggggc aagagttttg aagatatgtt acgtttgatg     300
caagatcaaa tcatcatggc acgagtttac agtggacttg caaagtttac aaacaatctc     360
gccttgcacc aagagataga aacacaacta atgaaactag cttgggagga agaatctact     420
gatattgatc aggagcagag agtacttgac agtataagag acatgggaca atactggct     480 agagcacacg agcagctata tgaatgcaag ttggtgacaa ataagttgag agcaatgcta     540
```

-continued

```
caaacagttg aagatgaact cgaaaacgag cagacttata taacgttctt gactcagcta      600
gcttccaagg cactaccaga tgctatccac tgcttgacca tgcgcttgaa tctagagtat      660
catctcctgc ctttaccgat gagaaatttt ccaaggaggg agaatttgga gaatccaaaa      720
ctttaccact acgctctctt ctctgataat gtactggctg catcagttgt tgtcaactcc      780
acagtcatga atgcacagga tccttcaagg catgttttcc accttgtgac tgataagctc      840
aactttggag caatgagtat gtggtttctg ttgaaccctc ctggagaagc gaccatccat      900
gtccaaaggt ttgaagattt tacttggctc aactcatctt actctccagt tttgagtcag      960
ctcgagtcag cagctatgaa gaagttctac ttcaagacag cgaggtctga atcagttgaa     1020
tcaggctcag aaaaccctca agtaccggta ccgaaataca tgtcaatgct taaccacctg     1080
aggttctaca tccctaggat cttcccaaag ttggagaaaa tcttgtttgt tgacgatgat     1140
gtggttgttc agaaggattt aactccccta tggtccattg atcttaaagg gaaagtgaat     1200 gaaactttg atcccaagtt ctgcggatgg gcttatggga tgaacatctt cgacctgaaa     1260
gaatggaaga gaacaacat tacagaaact tatcacttttt ggcaaaacct gaacgaaaac     1320
cggactctat ggaaactagg aacattgcca ccagggctca taacgttcta caatctgaca     1380
caaccacttc agagaaaatg gcacttactt ggactgggtt atgataaagg aatcgatgtc     1440
aagaagattg aaagatcagc tgttatacat tacaatggac acatgaaacc atggacagag     1500
atggggataa gcaagtatca gccatattgg acgaagtaca ccaatttga ccatccttac      1560 atctttactt gcaggctgtt tgagtga                                         1587
```

<210> SEQ ID NO 16
<211> LENGTH: 528
<212> TYPE: PRT
<213> ORGANISM: Arabidopsis thaliana

<400> SEQUENCE: 16

```
Met Thr Asp Ala Cys Cys Leu Lys Gly Asn Glu Asp Lys Met Val Pro
1               5                   10                  15

Arg Phe Gly His Gly Thr Trp Ile Gly Lys Ala Phe Asn Asp Thr Pro
            20                  25                  30

Glu Met Leu His Glu Arg Ser Leu Arg Gln Glu Lys Arg Leu Glu Arg
        35                  40                  45

Ala Asn Glu Leu Met Asn Asp Asp Ser Leu Gln Lys Leu Glu Thr Ala
    50                  55                  60

Ala Met Ala Arg Ser Arg Ser Val Asp Ser Ala Pro Leu Gly Asn Tyr
65                  70                  75                  80

Thr Ile Trp Lys Asn Glu Tyr Arg Arg Gly Lys Ser Phe Glu Asp Met
                85                  90                  95

Leu Arg Leu Met Gln Asp Gln Ile Ile Met Ala Arg Val Tyr Ser Gly
            100                 105                 110

Leu Ala Lys Phe Thr Asn Asn Leu Ala Leu His Gln Glu Ile Glu Thr
        115                 120                 125

Gln Leu Met Lys Leu Ala Trp Glu Glu Ser Thr Asp Ile Asp Gln
    130                 135                 140

Glu Gln Arg Val Leu Asp Ser Ile Arg Asp Met Gly Gln Ile Leu Ala
145                 150                 155                 160

Arg Ala His Glu Gln Leu Tyr Glu Cys Lys Leu Val Thr Asn Lys Leu
                165                 170                 175

Arg Ala Met Leu Gln Thr Val Glu Asp Glu Leu Glu Asn Glu Gln Thr
```

```
                    180                 185                 190
Tyr Ile Thr Phe Leu Thr Gln Leu Ala Ser Lys Ala Leu Pro Asp Ala
            195                 200                 205

Ile His Cys Leu Thr Met Arg Leu Asn Leu Glu Tyr His Leu Leu Pro
        210                 215                 220

Leu Pro Met Arg Asn Phe Pro Arg Arg Glu Asn Leu Glu Asn Pro Lys
225                 230                 235                 240

Leu Tyr His Tyr Ala Leu Phe Ser Asp Asn Val Leu Ala Ala Ser Val
            245                 250                 255

Val Val Asn Ser Thr Val Met Asn Ala Gln Asp Pro Ser Arg His Val
        260                 265                 270

Phe His Leu Val Thr Asp Lys Leu Asn Phe Gly Ala Met Ser Met Trp
    275                 280                 285

Phe Leu Leu Asn Pro Pro Gly Glu Ala Thr Ile His Val Gln Arg Phe
290                 295                 300

Glu Asp Phe Thr Trp Leu Asn Ser Ser Tyr Ser Pro Val Leu Ser Gln
305                 310                 315                 320

Leu Glu Ser Ala Ala Met Lys Lys Phe Tyr Phe Lys Thr Ala Arg Ser
            325                 330                 335

Glu Ser Val Glu Ser Gly Ser Glu Asn Leu Lys Tyr Arg Tyr Pro Lys
        340                 345                 350

Tyr Met Ser Met Leu Asn His Leu Arg Phe Tyr Ile Pro Arg Ile Phe
    355                 360                 365

Pro Lys Leu Glu Lys Ile Leu Phe Val Asp Asp Val Val Val Val Gln
370                 375                 380

Lys Asp Leu Thr Pro Leu Trp Ser Ile Asp Leu Lys Gly Lys Val Asn
385                 390                 395                 400

Glu Asn Phe Asp Pro Lys Phe Cys Gly Trp Ala Tyr Gly Met Asn Ile
            405                 410                 415

Phe Asp Leu Lys Glu Trp Lys Lys Asn Asn Ile Thr Glu Thr Tyr His
        420                 425                 430

Phe Trp Gln Asn Leu Asn Glu Asn Arg Thr Leu Trp Lys Leu Gly Thr
    435                 440                 445

Leu Pro Pro Gly Leu Ile Thr Phe Tyr Asn Leu Thr Gln Pro Leu Gln
450                 455                 460

Arg Lys Trp His Leu Leu Gly Leu Gly Tyr Asp Lys Gly Ile Asp Val
465                 470                 475                 480

Lys Lys Ile Glu Arg Ser Ala Val Ile His Tyr Asn Gly His Met Lys
            485                 490                 495

Pro Trp Thr Glu Met Gly Ile Ser Lys Tyr Gln Pro Tyr Trp Thr Lys
        500                 505                 510

Tyr Thr Asn Phe Asp His Pro Tyr Ile Phe Thr Cys Arg Leu Phe Glu
    515                 520                 525

<210> SEQ ID NO 17
<211> LENGTH: 1602
<212> TYPE: DNA
<213> ORGANISM: Arabidopsis thaliana

<400> SEQUENCE: 17
atgcagcttc acatatcgcc tagcatgaga agcattacga tatcgagcag caatgagttt    60
attgatttga tgaagatcaa agtcgcagct cgtcacatct cttaccgaac tctcttccac   120
actatcttaa tcctcgcttt cttgttacct tttgttttca tcctaaccgc tgttgttacc   180
```

```
cttgaaggtg tcaacaagtg ctcctctttt gattgtttcg ggaggcggct aggaccacgt    240
cttcttggta ggatagatga ttcagagcag agactagtta gagattttta caaaattcta    300
aatgaagtaa gcactcaaga aattccagat ggtttaaagc ttccagagtc ttttagtcaa    360
ctggtttcgg atatgaagaa caaccactat gatgctaaaa catttgccct cgtatttcga    420
gctatggtag agaagtttga aagggattta agggaatcca aatttgcaga actcatgaac    480
aagcactttg ctgcaagttc aattccaaaa ggaattcact gtctctcttt aagactaacc    540
gatgaatatt cctccaatgc tcatgcccgg agacagcttc cttccccgga gcttctccct    600
gttctctcag acaatgctta ccaccatttt gttctagcta cagataatat cttagctgca    660
tcggttgtgg tctcatctgc tgttcaatca tcttcaaaac ccgagaaaat tgtcttccat    720
gttatcacac acaagaaaac ctatgcgggt atgcattctt ggtttgcact caattctgtt    780
gctcctgcga ttgttgaagt gaaaagcgtt catcagtttg attggttaac aagagagaat    840
gttccagttc ttgaagctgt ggaaagccat aacagtatca gaaattatta ccatgggaat    900
catattgctg gtgcaaacct cagcgaaaca accctcgaa catttgcttc gaaactgcag    960
tcaagaagtc ccaaatacat atctttgctc aaccatctta gaatatatct accagagctt   1020
tttccgaact agacaaggt agtgttctta gatgatgata tagtgataca gaaagattta   1080
tctccgcttt gggatattga ccttaacggg aaggttaatg gagctgtgga gacttgtcga   1140
ggagaagacg tatgggttat gtcaaagcgt cttaggaact acttcaattt ttctcacccg   1200
ctcatcgcaa agcatttaga tcccgaagaa tgtgcttggg cttatggaat gaatatcttt   1260
gatctacgga cttggaggaa gacaaatatc agagaaacgt atcattcttg gcttaaagag   1320
aatctgaagt cgaatctaac aatgtggaaa cttggaacat gcctcctgc tctaatagca   1380
tttaaaggtc atgttcagcc aatagattcc tcttggcata tgcttggatt aggttatcag   1440
agcaagacca acttagaaaa tgcgaagaaa gctgcagtga ttcattacaa tggccaatca   1500
aagccgtggc ttgagatagg tttcgagcat ctcagaccat tctggacaaa atatgttaac   1560
tactccaatg atttcattaa gaattgtcat atcttggaat ag                     1602
```

<210> SEQ ID NO 18
<211> LENGTH: 533
<212> TYPE: PRT
<213> ORGANISM: Arabidopsis thaliana

<400> SEQUENCE: 18

```
Met Gln Leu His Ile Ser Pro Ser Met Arg Ser Ile Thr Ile Ser Ser
1               5                   10                  15

Ser Asn Glu Phe Ile Asp Leu Met Lys Ile Lys Val Ala Ala Arg His
                20                  25                  30

Ile Ser Tyr Arg Thr Leu Phe His Thr Ile Leu Ile Leu Ala Phe Leu
            35                  40                  45

Leu Pro Phe Val Phe Ile Leu Thr Ala Val Val Thr Leu Glu Gly Val
        50                  55                  60

Asn Lys Cys Ser Ser Phe Asp Cys Phe Gly Arg Arg Leu Gly Pro Arg
65                  70                  75                  80

Leu Leu Gly Arg Ile Asp Asp Ser Glu Gln Arg Leu Val Arg Asp Phe
                85                  90                  95

Tyr Lys Ile Leu Asn Glu Val Ser Thr Gln Glu Ile Pro Asp Gly Leu
            100                 105                 110

Lys Leu Pro Glu Ser Phe Ser Gln Leu Val Ser Asp Met Lys Asn Asn
        115                 120                 125
```

```
His Tyr Asp Ala Lys Thr Phe Ala Leu Val Phe Arg Ala Met Val Glu
    130                 135                 140

Lys Phe Glu Arg Asp Leu Arg Glu Ser Lys Phe Ala Glu Leu Met Asn
145                 150                 155                 160

Lys His Phe Ala Ala Ser Ser Ile Pro Lys Gly Ile His Cys Leu Ser
                165                 170                 175

Leu Arg Leu Thr Asp Glu Tyr Ser Ser Asn Ala His Ala Arg Arg Gln
                180                 185                 190

Leu Pro Ser Pro Glu Leu Leu Pro Val Leu Ser Asp Asn Ala Tyr His
            195                 200                 205

His Phe Val Leu Ala Thr Asp Asn Ile Leu Ala Ala Ser Val Val Val
    210                 215                 220

Ser Ser Ala Val Gln Ser Ser Lys Pro Glu Lys Ile Val Phe His
225                 230                 235                 240

Val Ile Thr Asp Lys Lys Thr Tyr Ala Gly Met His Ser Trp Phe Ala
                245                 250                 255

Leu Asn Ser Val Ala Pro Ala Ile Val Glu Val Lys Ser Val His Gln
                260                 265                 270

Phe Asp Trp Leu Thr Arg Glu Asn Val Pro Val Leu Glu Ala Val Glu
            275                 280                 285

Ser His Asn Ser Ile Arg Asn Tyr Tyr His Gly Asn His Ile Ala Gly
    290                 295                 300

Ala Asn Leu Ser Glu Thr Thr Pro Arg Thr Phe Ala Ser Lys Leu Gln
305                 310                 315                 320

Ser Arg Ser Pro Lys Tyr Ile Ser Leu Leu Asn His Leu Arg Ile Tyr
                325                 330                 335

Leu Pro Glu Leu Phe Pro Asn Leu Asp Lys Val Val Phe Leu Asp Asp
            340                 345                 350

Asp Ile Val Ile Gln Lys Asp Leu Ser Pro Leu Trp Asp Ile Asp Leu
    355                 360                 365

Asn Gly Lys Val Asn Gly Ala Val Glu Thr Cys Arg Gly Glu Asp Val
370                 375                 380

Trp Val Met Ser Lys Arg Leu Arg Asn Tyr Phe Asn Phe Ser His Pro
385                 390                 395                 400

Leu Ile Ala Lys His Leu Asp Pro Glu Glu Cys Ala Trp Ala Tyr Gly
                405                 410                 415

Met Asn Ile Phe Asp Leu Arg Thr Trp Arg Lys Thr Asn Ile Arg Glu
                420                 425                 430

Thr Tyr His Ser Trp Leu Lys Glu Asn Leu Lys Ser Asn Leu Thr Met
            435                 440                 445

Trp Lys Leu Gly Thr Leu Pro Pro Ala Leu Ile Ala Phe Lys Gly His
    450                 455                 460

Val Gln Pro Ile Asp Ser Ser Trp His Met Leu Gly Leu Gly Tyr Gln
465                 470                 475                 480

Ser Lys Thr Asn Leu Glu Asn Ala Lys Lys Ala Ala Val Ile His Tyr
                485                 490                 495

Asn Gly Gln Ser Lys Pro Trp Leu Glu Ile Gly Phe Glu His Leu Arg
                500                 505                 510

Pro Phe Trp Thr Lys Tyr Val Asn Tyr Ser Asn Asp Phe Ile Lys Asn
            515                 520                 525

Cys His Ile Leu Glu
    530
```

<210> SEQ ID NO 19
<211> LENGTH: 1686
<212> TYPE: DNA
<213> ORGANISM: Arabidopsis thaliana

<400> SEQUENCE: 19

| | | | | | |
|---|---|---|---|---|---|
| atggcggtgg | ccttccgtgg | aggccgggga | ggcgtcggat | ccggccaatc | taccggactt | 60 |
| cgtagtttct | tctcctaccg | gatctttatc | tccgctttgt | tctcttttct | cttcctcgcc | 120 |
| actttctccg | tcgttcttaa | ctcctctcgt | catcagcctc | atcaggatca | tacattgccg | 180 |
| agtatgggca | acgcatatat | gcagaggacg | tttttggctt | tgcaatcgga | tccattgaaa | 240 |
| actaggttgg | atctgataca | caagcaagcc | attgatcatt | tgacactggt | gaatgcgtat | 300 |
| gctgcttacg | ctaggaagct | aaagcttgat | gcttctaagc | agcttaagct | cttcgaagat | 360 |
| ttggctatca | acttctcgga | tttgcagtcg | aaacctggtt | tgaaatctgc | tgtgtctgat | 420 |
| aatggtaatg | ctcttgagga | ggattcgttt | aggcagcttg | agaagaagt | gaaggataag | 480 |
| gtgaagacag | cgaggatgat | gatcgttgag | tctaaagaga | gttatgatac | acagcttaaa | 540 |
| atccagaagt | tgaaagatac | aatctttgct | gtccaagaac | agttgacaaa | ggctaagaaa | 600 |
| aacggtgcgg | ttgctagctt | gatttcagcc | aagtcggttc | ctaaaagtct | tcattgtttg | 660 |
| gccatgaggc | ttgtaggaga | gaggatctct | aatcctgaga | agtacaagga | tgctccacct | 720 |
| gacccagccg | cagaggatcc | aactctttac | cactatgcga | ttttctctga | taatgtcatt | 780 |
| gctgtgtctg | ttgtggtgag | atcggttgtg | atgaacgctg | aggagccatg | aagcatgtc | 840 |
| ttccatgtgg | tgacagatcg | gatgaatctc | gcagccatga | aggtgtggtt | taagatgcgt | 900 |
| cctttggacc | gtggtgccca | tgttgagatt | aaatccgtgg | aggatttcaa | gttcttaaac | 960 |
| tcttcctatg | cgccggtctt | gaggcagctt | gagtctgcca | agttgcagaa | gttttacttt | 1020 |
| gagaatcaag | ctgagaacgc | aactaaagat | tcacataacc | tcaagttcaa | gaaccccaag | 1080 |
| tatctctcga | tgttgaacca | tctcagattt | tacttaccag | agatgtatcc | gaagctgaat | 1140 |
| aagattttgt | tcttggacga | tgatgttgtg | gtgcagaaag | acgtgactgg | tttatggaaa | 1200 |
| atcaacttgg | atggcaaggt | gaatggagcc | gttgagacat | gttttggttc | ttttcatcga | 1260 |
| tatggtcaat | acttaaactt | ctctcatcct | ttgatcaaag | agaactttaa | ccccagtgcc | 1320 |
| tgtgcttggg | cctttggaat | gaacatattc | gatctcaatg | cctggagacg | cgagaagtgc | 1380 |
| accgatcaat | accattactg | gcagaacctg | aatgaagaca | gaactctctg | gaaattggga | 1440 |
| actctacctc | cgggattgat | cacattctat | tcaaagacga | aatcattgga | caaatcatgg | 1500 |
| catgtacttg | ggttaggcta | taacccggga | gtgagcatgg | acgaaatcag | aaatgcagga | 1560 |
| gtgattcatt | acaatggaaa | catgaaaccg | tggctagaca | ttgcgatgaa | ccaatacaag | 1620 |
| tctctctgga | ctaaatatgt | tgataacgaa | atggagtttg | tgcagatgtg | caattttggt | 1680 |
| ctctaa | | | | | | 1686 |

<210> SEQ ID NO 20
<211> LENGTH: 561
<212> TYPE: PRT
<213> ORGANISM: Arabidopsis thaliana

<400> SEQUENCE: 20

Met Ala Val Ala Phe Arg Gly Gly Arg Gly Val Gly Ser Gly Gln
1               5                   10                  15

Ser Thr Gly Leu Arg Ser Phe Phe Ser Tyr Arg Ile Phe Ile Ser Ala
            20                  25                  30

```
Leu Phe Ser Phe Leu Phe Leu Ala Thr Phe Ser Val Val Leu Asn Ser
             35                  40                  45

Ser Arg His Gln Pro His Gln Asp His Thr Leu Pro Ser Met Gly Asn
 50                  55                  60

Ala Tyr Met Gln Arg Thr Phe Leu Ala Leu Gln Ser Asp Pro Leu Lys
 65                  70                  75                  80

Thr Arg Leu Asp Leu Ile His Lys Gln Ala Ile Asp His Leu Thr Leu
                 85                  90                  95

Val Asn Ala Tyr Ala Ala Tyr Ala Arg Lys Leu Lys Leu Asp Ala Ser
                100                 105                 110

Lys Gln Leu Lys Leu Phe Glu Asp Leu Ala Ile Asn Phe Ser Asp Leu
            115                 120                 125

Gln Ser Lys Pro Gly Leu Lys Ser Ala Val Ser Asp Asn Gly Asn Ala
            130                 135                 140

Leu Glu Glu Asp Ser Phe Arg Gln Leu Glu Lys Glu Val Lys Asp Lys
145                 150                 155                 160

Val Lys Thr Ala Arg Met Met Ile Val Glu Ser Lys Glu Ser Tyr Asp
                165                 170                 175

Thr Gln Leu Lys Ile Gln Lys Leu Lys Asp Thr Ile Phe Ala Val Gln
            180                 185                 190

Glu Gln Leu Thr Lys Ala Lys Lys Asn Gly Ala Val Ala Ser Leu Ile
            195                 200                 205

Ser Ala Lys Ser Val Pro Lys Ser Leu His Cys Leu Ala Met Arg Leu
210                 215                 220

Val Gly Glu Arg Ile Ser Asn Pro Glu Lys Tyr Lys Asp Ala Pro Pro
225                 230                 235                 240

Asp Pro Ala Ala Glu Asp Pro Thr Leu Tyr His Tyr Ala Ile Phe Ser
                245                 250                 255

Asp Asn Val Ile Ala Val Ser Val Val Arg Ser Val Val Met Asn
                260                 265                 270

Ala Glu Glu Pro Trp Lys His Val Phe His Val Val Thr Asp Arg Met
            275                 280                 285

Asn Leu Ala Ala Met Lys Val Trp Phe Lys Met Arg Pro Leu Asp Arg
290                 295                 300

Gly Ala His Val Glu Ile Lys Ser Val Glu Asp Phe Lys Phe Leu Asn
305                 310                 315                 320

Ser Ser Tyr Ala Pro Val Leu Arg Gln Leu Glu Ser Ala Lys Leu Gln
                325                 330                 335

Lys Phe Tyr Phe Glu Asn Gln Ala Glu Asn Ala Thr Lys Asp Ser His
            340                 345                 350

Asn Leu Lys Phe Lys Asn Pro Lys Tyr Leu Ser Met Leu Asn His Leu
            355                 360                 365

Arg Phe Tyr Leu Pro Glu Met Tyr Pro Lys Leu Asn Lys Ile Leu Phe
370                 375                 380

Leu Asp Asp Asp Val Val Gln Lys Asp Val Thr Gly Leu Trp Lys
385                 390                 395                 400

Ile Asn Leu Asp Gly Lys Val Asn Gly Ala Val Glu Thr Cys Phe Gly
                405                 410                 415

Ser Phe His Arg Tyr Gly Gln Tyr Leu Asn Phe Ser His Pro Leu Ile
            420                 425                 430

Lys Glu Asn Phe Asn Pro Ser Ala Cys Ala Trp Ala Phe Gly Met Asn
            435                 440                 445
```

```
Ile Phe Asp Leu Asn Ala Trp Arg Arg Glu Lys Cys Thr Asp Gln Tyr
    450                 455                 460

His Tyr Trp Gln Asn Leu Asn Glu Asp Arg Thr Leu Trp Lys Leu Gly
465                 470                 475                 480

Thr Leu Pro Pro Gly Leu Ile Thr Phe Tyr Ser Lys Thr Lys Ser Leu
                485                 490                 495

Asp Lys Ser Trp His Val Leu Gly Leu Gly Tyr Asn Pro Gly Val Ser
            500                 505                 510

Met Asp Glu Ile Arg Asn Ala Gly Val Ile His Tyr Asn Gly Asn Met
        515                 520                 525

Lys Pro Trp Leu Asp Ile Ala Met Asn Gln Tyr Lys Ser Leu Trp Thr
    530                 535                 540

Lys Tyr Val Asp Asn Glu Met Glu Phe Val Gln Met Cys Asn Phe Gly
545                 550                 555                 560

Leu
```

<210> SEQ ID NO 21
<211> LENGTH: 1680
<212> TYPE: DNA
<213> ORGANISM: Arabidopsis thaliana

<400> SEQUENCE: 21

```
atggctaatc accaccgact tttacgcggc ggcggatctc cggccataat cggtggcaga      60
atcacactca cagctttcgc ttccactatc gcactcttcc tcttcactct ctccttcttc     120
ttcgcttcag attctaacga ttctcctgat ctccttcttc ccggtgttga gtactctaat     180
ggagtcggat ctagaagatc catgttggat atcaaatcgg atccgcttaa gccacggttg     240
attcagatcc ggaaacaagc tgatgatcat cggtcattag cattagctta tgcttcttac     300
gcgagaaagc ttaagctcga gaattcgaaa ctcgtcagga tcttcgctga tctttcgagg     360
aattacacgg atctgattaa caaaccgacg tatcgagctt gtatgattc tgatggagcc     420
tcgattgaag aatctgtgct taggcaattt gagaagaag ttaaggaacg gattaaaatg      480
actcgtcaag tgattgctga agctaaagag tcttttgata tcagttgaa gattcagaag      540
ctgaaagata cgattttcgc tgttaacgaa cagttaacta atgctaagaa gcaaggtgcg     600
ttttcgagtt tgatcgctgc gaaatcgatt ccgaaaggat gcattgtct gctatgagg      660
ctgatggaag agaggattgc tcaccctgag aagtatactg atgaagggaa agatagaccg     720
cgggagctcg aggatccgaa tctttaccat tacgctatat tttcggataa tgtgattgcg     780
gcttcggtgg ttgtgaactc tgctgtgaag aatgctaagg agccgtggaa gcatgttttt     840
cacgttgtga ctgataagat gaatcttgga gctatgcagg ttatgtttaa actgaaggag     900
tataaggag ctcatgtaga agttaaagct gttgaggatt atacgttttt gaactcttcg      960
tatgtgcctg tgttgaagca gttagaatct gcgaatcttc agaagtttta tttcgagaat    1020
aagctcgaga atgcgacgaa agataccacg aatatgaagt tcaggaaccc caagtattta    1080
tctatattga tcacttgag gttttattta cccgagatgt acccgaaact acataggata    1140
ctgttttgg acgatgatgt ggttgtgcag aaggatttaa cgggtctgtg ggagattgat    1200
atggatggga agtgaatgg agctgtgagg acttgttttg ggtcgtttca tcggtacgct    1260
caatacatga atttctcaca tcctttgatc aaagagaagt taatcccaa agcatgtgcg    1320
tgggcgtatg gaatgaactt ctttgatctt gatgctggga gagagagaa gtgcacagaa    1380
gaatatcact actggcaaaa tctgaacgag aacagggctc tatggaaact ggggacgtta    1440
```

```
ccaccgggac tgatcacctt ttactcaacc acaaagccgc tggacaaatc atggcatgtg   1500
cttgggctgg gttacaatcc gagcattagc atggatgaga tccgcaacgc tgcagtggta   1560
cacttcaacg gtaacatgaa gccatggctt gacatagcta tgaaccagtt tcgaccactt   1620
tggaccaaac acgtcgacta tgacctcgag tttgttcagg cttgcaattt tggcctctga   1680
```

<210> SEQ ID NO 22
<211> LENGTH: 559
<212> TYPE: PRT
<213> ORGANISM: Arabidopsis thaliana
<400> SEQUENCE: 22

```
Met Ala Asn His His Arg Leu Leu Arg Gly Gly Gly Ser Pro Ala Ile
1               5                   10                  15

Ile Gly Gly Arg Ile Thr Leu Thr Ala Phe Ala Ser Thr Ile Ala Leu
            20                  25                  30

Phe Leu Phe Thr Leu Ser Phe Phe Phe Ala Ser Asp Ser Asn Asp Ser
        35                  40                  45

Pro Asp Leu Leu Leu Pro Gly Val Glu Tyr Ser Asn Gly Val Gly Ser
    50                  55                  60

Arg Arg Ser Met Leu Asp Ile Lys Ser Asp Pro Leu Lys Pro Arg Leu
65                  70                  75                  80

Ile Gln Ile Arg Lys Gln Ala Asp Asp His Arg Ser Leu Ala Leu Ala
                85                  90                  95

Tyr Ala Ser Tyr Ala Arg Lys Leu Lys Leu Glu Asn Ser Lys Leu Val
            100                 105                 110

Arg Ile Phe Ala Asp Leu Ser Arg Asn Tyr Thr Asp Leu Ile Asn Lys
        115                 120                 125

Pro Thr Tyr Arg Ala Leu Tyr Asp Ser Asp Gly Ala Ser Ile Glu Glu
    130                 135                 140

Ser Val Leu Arg Gln Phe Glu Lys Glu Val Lys Glu Arg Ile Lys Met
145                 150                 155                 160

Thr Arg Gln Val Ile Ala Glu Ala Lys Glu Ser Phe Asp Asn Gln Leu
                165                 170                 175

Lys Ile Gln Lys Leu Lys Asp Thr Ile Phe Ala Val Asn Glu Gln Leu
            180                 185                 190

Thr Asn Ala Lys Lys Gln Gly Ala Phe Ser Ser Leu Ile Ala Ala Lys
        195                 200                 205

Ser Ile Pro Lys Gly Leu His Cys Leu Ala Met Arg Leu Met Glu Glu
    210                 215                 220

Arg Ile Ala His Pro Glu Lys Tyr Thr Asp Glu Gly Lys Asp Arg Pro
225                 230                 235                 240

Arg Glu Leu Glu Asp Pro Asn Leu Tyr His Tyr Ala Ile Phe Ser Asp
                245                 250                 255

Asn Val Ile Ala Ala Ser Val Val Asn Ser Ala Val Lys Asn Ala
            260                 265                 270

Lys Glu Pro Trp Lys His Val Phe His Val Val Thr Asp Lys Met Asn
        275                 280                 285

Leu Gly Ala Met Gln Val Met Phe Lys Leu Lys Glu Tyr Lys Gly Ala
    290                 295                 300

His Val Glu Val Lys Ala Val Glu Asp Tyr Thr Phe Leu Asn Ser Ser
305                 310                 315                 320

Tyr Val Pro Val Leu Lys Gln Leu Glu Ser Ala Asn Leu Gln Lys Phe
                325                 330                 335
```

```
Tyr Phe Glu Asn Lys Leu Glu Asn Ala Thr Lys Asp Thr Thr Asn Met
                340                 345                 350

Lys Phe Arg Asn Pro Lys Tyr Leu Ser Ile Leu Asn His Leu Arg Phe
            355                 360                 365

Tyr Leu Pro Glu Met Tyr Pro Lys Leu His Arg Ile Leu Phe Leu Asp
        370                 375                 380

Asp Asp Val Val Gln Lys Asp Leu Thr Gly Leu Trp Glu Ile Asp
385                 390                 395                 400

Met Asp Gly Lys Val Asn Gly Ala Val Glu Thr Cys Phe Gly Ser Phe
                405                 410                 415

His Arg Tyr Ala Gln Tyr Met Asn Phe Ser His Pro Leu Ile Lys Glu
            420                 425                 430

Lys Phe Asn Pro Lys Ala Cys Ala Trp Ala Tyr Gly Met Asn Phe Phe
        435                 440                 445

Asp Leu Asp Ala Trp Arg Arg Glu Lys Cys Thr Glu Glu Tyr His Tyr
    450                 455                 460

Trp Gln Asn Leu Asn Glu Asn Arg Ala Leu Trp Lys Leu Gly Thr Leu
465                 470                 475                 480

Pro Pro Gly Leu Ile Thr Phe Tyr Ser Thr Thr Lys Pro Leu Asp Lys
                485                 490                 495

Ser Trp His Val Leu Gly Leu Gly Tyr Asn Pro Ser Ile Ser Met Asp
            500                 505                 510

Glu Ile Arg Asn Ala Ala Val Val His Phe Asn Gly Asn Met Lys Pro
        515                 520                 525

Trp Leu Asp Ile Ala Met Asn Gln Phe Arg Pro Leu Trp Thr Lys His
    530                 535                 540

Val Asp Tyr Asp Leu Glu Phe Val Gln Ala Cys Asn Phe Gly Leu
545                 550                 555

<210> SEQ ID NO 23
<211> LENGTH: 1623
<212> TYPE: DNA
<213> ORGANISM: Arabidopsis thaliana

<400> SEQUENCE: 23
atgaagtttt acatatcagc gacggggatt aagaaggtta cgatatcaaa tcccggcgtc      60
ggaatcggta aggaagcgg aggatgtgcg gctgcagcgg cggcgttagc agcgcggaga      120
ttctctagtc gcacgttgtt actgttgctg ctgctgctcg ctatcgtcct ccctttttatc    180 ttcgtcaggt tcgcgtttct cgtcctcgaa tctgcctccg tttgcgattc accactcgat     240
tgcatgggac tcagactttt ccgtgggggc gacacatctc tgaaaattgg ggaagagttg     300
acacgggctc tagtggaaga acgacagat catcaggacg ttaatggaag aggaacgaag      360
ggatcattgg agtcattcga cgaccttgtt aaggagatga cgttaaaacg ccgtgacata     420
agggcgtttg cttccgtgac taagaagatg ctgttgcaga tggaacgtaa agtccaatca     480
gcgaaacatc atgagttagt gtactggcat ttagcctctc acggtattcc taaaagcctc     540
cattgccttt ccctcagatt aactgaagag tactctgtaa atgcaatggc tcgaatgcgt     600
ttgcctccgc tgagtccgt atcacgtctg accgacccat cttttcatca tattgtcctc     660
ctgactgaca atgtccttgc tgcctctgtc gtcatatcgt ctactgtaca aaacgctgtg     720
aatcccgaga agtttgtctt tcatattgtt accgataaga aaacctatac ccctatgcat     780
gcttggtttg ctatcaactc tgcttcatca ccagttgttg aagtaaaggg acttcatcag     840
tatgattggc ctcaagaagt gaacttcaaa gttagagaga tgctggacat tcaccgctta     900
```

```
atttggagac gacattatca aaatttgaaa gactctgatt ttagtttgt tgagggtact    960
catgagcagt ccttgcaagc tctaaatcct agctgccttg ccctttgaa ccatcttcgc   1020
atttacattc ccaagctttt tccagatctc aacaagatag tgttgttgga tgatgatgta   1080
gtagtacaga gcgatctttc gtctttatgg gaaacggatc tcaacggtaa agttgttggt   1140
gctgtcgttg attcgtggtg cggagacaac tgttgccccg gaagaaaata caaagactat   1200
ttcaacttct cacatccttt gatctcatca aacttagttc aagaagactg tgcttggctt   1260
tctggtatga atgtctttga tctcaaagcc tggagacaaa ccaatattac tgaagcttac   1320
tctacatggc taagactcag tgttaggtca ggactacaat tatggcaacc aggggcttta   1380
ccaccgacat tacttgcttt caaaggactt acacagtctc ttgaaccatc atggcacgtc   1440
gctggactag gttctcgatc cgtaaaatcc cctcaagaga ttctgaaatc tgcttcggtt   1500
ttacatttca gcggtccagc aaaaccgtgg ctagagatca gtaaccctga ggtacgatct   1560
ctttggtata gatacgtaaa ttcctccgac atcttcgtta gaaaatgcaa aatcatgaac   1620
tga                                                                1623
```

<210> SEQ ID NO 24
<211> LENGTH: 540
<212> TYPE: PRT
<213> ORGANISM: Arabidopsis thaliana

<400> SEQUENCE: 24

```
Met Lys Phe Tyr Ile Ser Ala Thr Gly Ile Lys Lys Val Thr Ile Ser
1               5                  10                  15

Asn Pro Gly Val Gly Ile Gly Lys Gly Ser Gly Gly Cys Ala Ala Ala
            20                  25                  30

Ala Ala Ala Leu Ala Ala Arg Arg Phe Ser Ser Arg Thr Leu Leu Leu
        35                  40                  45

Leu Leu Leu Leu Leu Ala Ile Val Leu Pro Phe Ile Phe Val Arg Phe
    50                  55                  60

Ala Phe Leu Val Leu Glu Ser Ala Ser Val Cys Asp Ser Pro Leu Asp
65                  70                  75                  80

Cys Met Gly Leu Arg Leu Phe Arg Gly Gly Asp Thr Ser Leu Lys Ile
                85                  90                  95

Gly Glu Glu Leu Thr Arg Ala Leu Val Glu Glu Thr Thr Asp His Gln
            100                 105                 110

Asp Val Asn Gly Arg Gly Thr Lys Gly Ser Leu Glu Ser Phe Asp Asp
        115                 120                 125

Leu Val Lys Glu Met Thr Leu Lys Arg Arg Asp Ile Arg Ala Phe Ala
    130                 135                 140

Ser Val Thr Lys Lys Met Leu Leu Gln Met Glu Arg Lys Val Gln Ser
145                 150                 155                 160

Ala Lys His His Glu Leu Val Tyr Trp His Leu Ala Ser His Gly Ile
                165                 170                 175

Pro Lys Ser Leu His Cys Leu Ser Leu Arg Leu Thr Glu Glu Tyr Ser
            180                 185                 190

Val Asn Ala Met Ala Arg Met Arg Leu Pro Pro Glu Ser Val Ser
        195                 200                 205

Arg Leu Thr Asp Pro Ser Phe His His Ile Val Leu Leu Thr Asp Asn
    210                 215                 220

Val Leu Ala Ala Ser Val Val Ile Ser Ser Thr Val Gln Asn Ala Val
225                 230                 235                 240
```

```
Asn Pro Glu Lys Phe Val Phe His Ile Val Thr Asp Lys Lys Thr Tyr
            245                 250                 255

Thr Pro Met His Ala Trp Phe Ala Ile Asn Ser Ala Ser Ser Pro Val
            260                 265                 270

Val Glu Val Lys Gly Leu His Gln Tyr Asp Trp Pro Gln Glu Val Asn
            275                 280                 285

Phe Lys Val Arg Glu Met Leu Asp Ile His Arg Leu Ile Trp Arg Arg
            290                 295                 300

His Tyr Gln Asn Leu Lys Asp Ser Asp Phe Ser Phe Val Glu Gly Thr
305                 310                 315                 320

His Glu Gln Ser Leu Gln Ala Leu Asn Pro Ser Cys Leu Ala Leu Leu
            325                 330                 335

Asn His Leu Arg Ile Tyr Ile Pro Lys Leu Phe Pro Asp Leu Asn Lys
            340                 345                 350

Ile Val Leu Leu Asp Asp Asp Val Val Gln Ser Asp Leu Ser Ser
            355                 360                 365

Leu Trp Glu Thr Asp Leu Asn Gly Lys Val Val Gly Ala Val Val Asp
370                 375                 380

Ser Trp Cys Gly Asp Asn Cys Cys Pro Gly Arg Lys Tyr Lys Asp Tyr
385                 390                 395                 400

Phe Asn Phe Ser His Pro Leu Ile Ser Ser Asn Leu Val Gln Glu Asp
            405                 410                 415

Cys Ala Trp Leu Ser Gly Met Asn Val Phe Asp Leu Lys Ala Trp Arg
            420                 425                 430

Gln Thr Asn Ile Thr Glu Ala Tyr Ser Thr Trp Leu Arg Leu Ser Val
            435                 440                 445

Arg Ser Gly Leu Gln Leu Trp Gln Pro Gly Ala Leu Pro Pro Thr Leu
            450                 455                 460

Leu Ala Phe Lys Gly Leu Thr Gln Ser Leu Glu Pro Ser Trp His Val
465                 470                 475                 480

Ala Gly Leu Gly Ser Arg Ser Val Lys Ser Pro Gln Glu Ile Leu Lys
            485                 490                 495

Ser Ala Ser Val Leu His Phe Ser Gly Pro Ala Lys Pro Trp Leu Glu
            500                 505                 510

Ile Ser Asn Pro Glu Val Arg Ser Leu Trp Tyr Arg Tyr Val Asn Ser
            515                 520                 525

Ser Asp Ile Phe Val Arg Lys Cys Lys Ile Met Asn
530                 535                 540

<210> SEQ ID NO 25
<211> LENGTH: 2043
<212> TYPE: DNA
<213> ORGANISM: Arabidopsis thaliana

<400> SEQUENCE: 25
atgacgacgt tctctacatg cgccgccttt ttatcgctgg tagtagtgct acatgctgtt      60
catgtcggtg agccattttt agagtcacaa gcaccccaca gagaacttaa agcttatcgt     120
ccgctgcaag ataataatct acaggaggtg tatgcttcct cagctgctgc agtgcactac     180
gatccagatc tgaaagatgt gaacatagtt gcgacataca gtgaccatta cggcaatata     240
cgccttggta gggtgaaaat gggggatctt tcaccttctt gggttttgga gaatcctgcc     300
tatcaagtta gccgcaaaac aaaaggttcg cagctagtta taccacggga ttcatttcaa     360
aatgatactg gaatggaaga taatgcaagc cattctacaa ctaatcagac tgatgaaagc     420
```

-continued

```
gaaaatcagt tccaaacgt ggattttgca agcccagcaa aactgaagcg gcagattta      480
cgtcaggaaa ggagaggtca cgaactttta gagctgatcc gacaagaaaa ggaaactgat    540
gagcagatgc aagaagcagc cattcagaag tcaatgagct ttgaaaactc agtcatagg     600
aaatacagta tatggaggag agactatgag agcccaaatg ctgatgctat cttgaagctt    660
atgagagacc agatcataat ggcaaaagca tatgcaaata ttgccaaatc aaaaaatgta    720
accaatctgt acgttttctt gatgcagcag tgtggagaaa ataaacgtgt tataggtaaa    780
gcaacctctg atgctgacct tccttcaagc gctcttgatc aagcaaaagc catgggccat    840
gcactctctc ttgcaaaaga cgagttatat gactgccatg aacttgcaaa aaagttccgg    900
gccatccttc agtccactga acgcaaagta gatggactga agaaaaaggg aaccttctta    960
attcagctag ctgccaaaac atttcccaag ccattgcatt gcctgagtct gcagctagcg    1020
gcagactatt ttattctagg tttcaatgaa gaggatgcag tgaaagagga tgtcagtcaa    1080
aagaagcttg aagatccttc gctctatcac tatgcgatct tttcggataa cgttctggct    1140
acatcagtgg tggtgaactc cactgtcttg aatgcaaagg aaccgcagag gcatgtgttc    1200
catatagtaa ctgacaaact gaattttggt gcaatgaaga tgtggtttcg catcaatgct    1260
cctgctgatg cgacgattca agttgaaaac ataaatgatt tcaagtggct gaactcctct    1320
tactgctctg ttctacggca gcttgaatct gcaaggctga agaatacta tttcaaagca     1380
aatcatcctt catcaatctc agctggcgca gataatctaa agtaccgcaa cccaaagtat    1440
ctatcgatgc tgaatcatct cagattctac cttcctgagg tttatccgaa gctggagaag    1500
attctgtttc tagacgatga cattgtggtg cagaaggacc tggcaccact atgggaaata    1560
gacatgcaag aaaagtgaa tggtgcggtg agacgtgca aggagagctt ccacagattt      1620
gacaagtacc tcaacttctc aaatccaaag atttcagaga attttgacgc tggtgcttgt    1680
gggtgggcat ttgggatgaa tatgtttgac ctgaaagagt ggaggaaacg gaacattaca    1740
gggatatatc actattggca agacttgaat gaagacagaa cactgtggaa gctgggatcg    1800
ttgccaccgg ggctgataac attttacaac ctgacgtatg caatggatag gagctggcac    1860
gtactagggc tgggatatga cccagcgcta aaccaaacag caatagagaa tgcagcggta    1920
gtgcattaca atgggaacta caagccatgg ctgggtttag cattcgccaa gtacaaaccg    1980
tactggtcca agtacgttga gtacgacaac ccttatctcc gacggtgcga catcaatgaa    2040
tga                                                                   2043
```

<210> SEQ ID NO 26
<211> LENGTH: 680
<212> TYPE: PRT
<213> ORGANISM: Arabidopsis thaliana

<400> SEQUENCE: 26

```
Met Thr Thr Phe Ser Thr Cys Ala Ala Phe Leu Ser Leu Val Val Val
1               5                  10                  15

Leu His Ala Val His Val Gly Gly Ala Ile Leu Glu Ser Gln Ala Pro
            20                  25                  30

His Arg Glu Leu Lys Ala Tyr Arg Pro Leu Gln Asp Asn Asn Leu Gln
        35                  40                  45

Glu Val Tyr Ala Ser Ser Ala Ala Ala Val His Tyr Asp Pro Asp Leu
    50                  55                  60

Lys Asp Val Asn Ile Val Ala Thr Tyr Ser Asp His Tyr Gly Asn Ile
65                  70                  75                  80
```

```
Arg Leu Gly Arg Val Lys Met Gly Asp Leu Ser Pro Ser Trp Val Leu
                85                  90                  95
Glu Asn Pro Ala Tyr Gln Val Ser Arg Lys Thr Lys Gly Ser Gln Leu
            100                 105                 110
Val Ile Pro Arg Asp Ser Phe Gln Asn Asp Thr Gly Met Glu Asp Asn
        115                 120                 125
Ala Ser His Ser Thr Thr Asn Gln Thr Asp Glu Ser Glu Asn Gln Phe
    130                 135                 140
Pro Asn Val Asp Phe Ala Ser Pro Ala Lys Leu Lys Arg Gln Ile Leu
145                 150                 155                 160
Arg Gln Glu Arg Arg Gly Gln Arg Thr Leu Glu Leu Ile Arg Gln Glu
                165                 170                 175
Lys Glu Thr Asp Glu Gln Met Gln Glu Ala Ala Ile Gln Lys Ser Met
            180                 185                 190
Ser Phe Glu Asn Ser Val Ile Gly Lys Tyr Ser Ile Trp Arg Arg Asp
        195                 200                 205
Tyr Glu Ser Pro Asn Ala Asp Ala Ile Leu Lys Leu Met Arg Asp Gln
    210                 215                 220
Ile Ile Met Ala Lys Ala Tyr Ala Asn Ile Ala Lys Ser Lys Asn Val
225                 230                 235                 240
Thr Asn Leu Tyr Val Phe Leu Met Gln Gln Cys Gly Glu Asn Lys Arg
                245                 250                 255
Val Ile Gly Lys Ala Thr Ser Asp Ala Asp Leu Pro Ser Ser Ala Leu
            260                 265                 270
Asp Gln Ala Lys Ala Met Gly His Ala Leu Ser Leu Ala Lys Asp Glu
        275                 280                 285
Leu Tyr Asp Cys His Glu Leu Ala Lys Lys Phe Arg Ala Ile Leu Gln
    290                 295                 300
Ser Thr Glu Arg Lys Val Asp Gly Leu Lys Lys Lys Gly Thr Phe Leu
305                 310                 315                 320
Ile Gln Leu Ala Ala Lys Thr Phe Pro Lys Pro Leu His Cys Leu Ser
                325                 330                 335
Leu Gln Leu Ala Ala Asp Tyr Phe Ile Leu Gly Phe Asn Glu Glu Asp
            340                 345                 350
Ala Val Lys Glu Asp Val Ser Gln Lys Lys Leu Glu Asp Pro Ser Leu
        355                 360                 365
Tyr His Tyr Ala Ile Phe Ser Asp Asn Val Leu Ala Thr Ser Val Val
    370                 375                 380
Val Asn Ser Thr Val Leu Asn Ala Lys Glu Pro Gln Arg His Val Phe
385                 390                 395                 400
His Ile Val Thr Asp Lys Leu Asn Phe Gly Ala Met Lys Met Trp Phe
                405                 410                 415
Arg Ile Asn Ala Pro Ala Asp Ala Thr Ile Gln Val Glu Asn Ile Asn
            420                 425                 430
Asp Phe Lys Trp Leu Asn Ser Tyr Cys Ser Val Leu Arg Gln Leu
        435                 440                 445
Glu Ser Ala Arg Leu Lys Glu Tyr Tyr Phe Lys Ala Asn His Pro Ser
    450                 455                 460
Ser Ile Ser Ala Gly Ala Asp Asn Leu Lys Tyr Arg Asn Pro Lys Tyr
465                 470                 475                 480
Leu Ser Met Leu Asn His Leu Arg Phe Tyr Leu Pro Glu Val Tyr Pro
                485                 490                 495
```

```
Lys Leu Glu Lys Ile Leu Phe Leu Asp Asp Ile Val Gln Lys
            500                 505                 510
Asp Leu Ala Pro Leu Trp Glu Ile Asp Met Gln Gly Lys Val Asn Gly
        515                 520                 525
Ala Val Glu Thr Cys Lys Glu Ser Phe His Arg Phe Asp Lys Tyr Leu
    530                 535                 540
Asn Phe Ser Asn Pro Lys Ile Ser Glu Asn Phe Asp Ala Gly Ala Cys
545                 550                 555                 560
Gly Trp Ala Phe Gly Met Asn Met Phe Asp Leu Lys Glu Trp Arg Lys
                565                 570                 575
Arg Asn Ile Thr Gly Ile Tyr His Tyr Trp Gln Asp Leu Asn Glu Asp
            580                 585                 590
Arg Thr Leu Trp Lys Leu Gly Ser Leu Pro Pro Gly Leu Ile Thr Phe
        595                 600                 605
Tyr Asn Leu Thr Tyr Ala Met Asp Arg Ser Trp His Val Leu Gly Leu
    610                 615                 620
Gly Tyr Asp Pro Ala Leu Asn Gln Thr Ala Ile Glu Asn Ala Ala Val
625                 630                 635                 640
Val His Tyr Asn Gly Asn Tyr Lys Pro Trp Leu Gly Leu Ala Phe Ala
                645                 650                 655
Lys Tyr Lys Pro Tyr Trp Ser Lys Tyr Val Glu Tyr Asp Asn Pro Tyr
            660                 665                 670
Leu Arg Arg Cys Asp Ile Asn Glu
        675                 680

<210> SEQ ID NO 27
<211> LENGTH: 1599
<212> TYPE: DNA
<213> ORGANISM: Arabidopsis thaliana

<400> SEQUENCE: 27
atgcagcttc acatatcgcc gagtatgaga agcattacga tttcgagcag caatgagttt      60
attgacttga tgaagatcaa ggtcgcagct cgtcacatct cttaccgaac tctcttccac     120
accatcttaa tcctcgcttt cttgttgcct tttgttttca ttctcaccgc tgttgttacc     180
cttgagggtg tcaacaaatg ctcctccatt gattgtttag ggaggcggat aggtccacgt     240
cttcttggta gggtagatga ttcagagaga ctagctagag acttttataa aattctaaac     300
gaagtaagca ctcaagaaat tccagatggt tgaagcttc caaattcttt tagtcaactt      360
gtttccgata tgaagaataa ccactatgat gcaaaaacat tgctcttgt gctgcgagcc      420 atgatggaga gtttgaacg tgatatgagg gaatcgaaat tgcagaact tatgaacaag      480 cactttgcag caagttccat tcccaaaggc attcattgtc tctctctaag actgacagat     540
gaatattcct ccaatgctca tgctcgaaga cagcttcctt accagagtt tctccctgtt      600 ctttcagata tgcttaccca cactttatt ttgtccacgg acaatatttt ggctgcctca      660
gttgtggtct catccgctgt tcagtcatct tcaaaacccg agaaaattgt ctttcacatc     720
attacagaca agaaaaccta tgcgggtatg cattcatggt ttgcgcttaa ttctgttgca     780
ccagcaattg ttgaggttaa aggtgttcat cagtttgact ggttgacgag agagaatgtt     840
ccggttttgg aagctgtgga aagccataat ggtgtcaggg actattatca tgggaatcat     900
gtcgctgggg caaacctcac cgaaacaact cctcgaacat tgcttcaaa attgcagtct     960 agaagtccaa atacatatc tttgctcaac catcttagaa tatatatacc agagcttttc    1020
ccgaacttgg acaaggtggt tttcttagac gatgatatag ttgtccaggg agacttaact    1080
```

-continued

```
ccactttggg atgttgacct cggtggtaag gtcaatgggg cagtagagac ttgcaggggt   1140
gaagatgaat gggtgatgtc aaagcgttta aggaactact tcaatttctc tcacccgctc   1200
atcgcaaagc atttagatcc tgaagaatgt gcttgggcat atggtatgaa tatcttcgat   1260
ctacaagctt ggaggaaaac aaatatcaga gaaacgtatc actcttggct tagagagaat   1320
ctaaagtcaa atctgacaat gtggaaactt ggaaccttgc ctcctgctct tatcgcgttc   1380
aagggtcacg tacacataat agactcgtca tggcatatgc taggattagg ctaccagagc   1440
aagaccaaca tagaaaatgt gaagaaagca gcagtgatcc actacaatgg gcagtcaaag   1500
ccatggctgg agattggttt cgagcatctg cggccattct ggaccaaata cgtcaactac   1560
tcaaatgatt tcatcaagaa ctgtcacata ttggagtag                          1599
```

<210> SEQ ID NO 28
<211> LENGTH: 532
<212> TYPE: PRT
<213> ORGANISM: Arabidopsis thaliana

<400> SEQUENCE: 28

```
Met Gln Leu His Ile Ser Pro Ser Met Arg Ser Ile Thr Ile Ser Ser
1               5                   10                  15

Ser Asn Glu Phe Ile Asp Leu Met Lys Ile Lys Val Ala Ala Arg His
                20                  25                  30

Ile Ser Tyr Arg Thr Leu Phe His Thr Ile Leu Ile Leu Ala Phe Leu
            35                  40                  45

Leu Pro Phe Val Phe Ile Leu Thr Ala Val Val Thr Leu Glu Gly Val
        50                  55                  60

Asn Lys Cys Ser Ser Ile Asp Cys Leu Gly Arg Arg Ile Gly Pro Arg
65                  70                  75                  80

Leu Leu Gly Arg Val Asp Asp Ser Glu Arg Leu Ala Arg Asp Phe Tyr
                85                  90                  95

Lys Ile Leu Asn Glu Val Ser Thr Gln Glu Ile Pro Asp Gly Leu Lys
            100                 105                 110

Leu Pro Asn Ser Phe Ser Gln Leu Val Ser Asp Met Lys Asn Asn His
        115                 120                 125

Tyr Asp Ala Lys Thr Phe Ala Leu Val Leu Arg Ala Met Met Glu Lys
    130                 135                 140

Phe Glu Arg Asp Met Arg Glu Ser Lys Phe Ala Glu Leu Met Asn Lys
145                 150                 155                 160

His Phe Ala Ala Ser Ser Ile Pro Lys Gly Ile His Cys Leu Ser Leu
                165                 170                 175

Arg Leu Thr Asp Glu Tyr Ser Ser Asn Ala His Ala Arg Arg Gln Leu
            180                 185                 190

Pro Ser Pro Glu Phe Leu Pro Val Leu Ser Asp Asn Ala Tyr His His
        195                 200                 205

Phe Ile Leu Ser Thr Asp Asn Ile Leu Ala Ala Ser Val Val Val Ser
    210                 215                 220

Ser Ala Val Gln Ser Ser Lys Pro Glu Lys Ile Val Phe His Ile
225                 230                 235                 240

Ile Thr Asp Lys Lys Thr Tyr Ala Gly Met His Ser Trp Phe Ala Leu
                245                 250                 255

Asn Ser Val Ala Pro Ala Ile Val Glu Val Lys Gly Val His Gln Phe
            260                 265                 270

Asp Trp Leu Thr Arg Glu Asn Val Pro Val Leu Glu Ala Val Glu Ser
```

```
                275                 280                 285
His Asn Gly Val Arg Asp Tyr Tyr His Gly Asn His Val Ala Gly Ala
    290                 295                 300

Asn Leu Thr Glu Thr Thr Pro Arg Thr Phe Ala Ser Lys Leu Gln Ser
305                 310                 315                 320

Arg Ser Pro Lys Tyr Ile Ser Leu Leu Asn His Leu Arg Ile Tyr Ile
                325                 330                 335

Pro Glu Leu Phe Pro Asn Leu Asp Lys Val Val Phe Leu Asp Asp Asp
            340                 345                 350

Ile Val Val Gln Gly Asp Leu Thr Pro Leu Trp Asp Val Asp Leu Gly
        355                 360                 365

Gly Lys Val Asn Gly Ala Val Glu Thr Cys Arg Gly Glu Asp Glu Trp
    370                 375                 380

Val Met Ser Lys Arg Leu Arg Asn Tyr Phe Asn Phe Ser His Pro Leu
385                 390                 395                 400

Ile Ala Lys His Leu Asp Pro Glu Glu Cys Ala Trp Ala Tyr Gly Met
                405                 410                 415

Asn Ile Phe Asp Leu Gln Ala Trp Arg Lys Thr Asn Ile Arg Glu Thr
            420                 425                 430

Tyr His Ser Trp Leu Arg Glu Asn Leu Lys Ser Asn Leu Thr Met Trp
        435                 440                 445

Lys Leu Gly Thr Leu Pro Pro Ala Leu Ile Ala Phe Lys Gly His Val
    450                 455                 460

His Ile Ile Asp Ser Ser Trp His Met Leu Gly Leu Gly Tyr Gln Ser
465                 470                 475                 480

Lys Thr Asn Ile Glu Asn Val Lys Lys Ala Ala Val Ile His Tyr Asn
                485                 490                 495

Gly Gln Ser Lys Pro Trp Leu Glu Ile Gly Phe Glu His Leu Arg Pro
            500                 505                 510

Phe Trp Thr Lys Tyr Val Asn Tyr Ser Asn Asp Phe Ile Lys Asn Cys
        515                 520                 525

His Ile Leu Glu
    530

<210> SEQ ID NO 29
<211> LENGTH: 1608
<212> TYPE: DNA
<213> ORGANISM: Arabidopsis thaliana

<400> SEQUENCE: 29
atgcagttac atatatctcc gagcttgaga catgtgactg tggtcacagg gaaaggattg      60
agagagttca taaagttaa ggttggttct agaagattct cttatcaaat ggtgttttac     120
tctctactct tcttcacttt tcttctccga ttcgtctttg ttctctccac cgttgatact     180
atcgacggcg atccctctcc ttgctcctct cttgcttgct ggggaaaag actaaagcca     240 aagcttttag gaagaagggt tgattctggt aatgttccag aagctatgta ccaagtttta     300
gaacagcctt taagcgaaca gaactcaaa ggaagatcag atatacctca aacacttcaa     360
gatttcatgt ctgaagtcaa agaagcaaa tcagacgcaa gagaatttgc tcaaaagcta     420
aaagaaatgg tgacattgat ggaacagaga acaagaacgg ctaagattca agagtattta     480
tatcgacatg tcgcatcaag cagcataccg aaacaacttc actgtttagc tcttaaacta     540
gccaacgaac actcgataaa cgcagcggcg cgtctccagc ttccagaagc tgagcttgtc     600
cctatgttgg tagacaacaa ctactttcac tttgtcttgg cttcagacaa tattcttgca     660
```

-continued

```
gcttcggttg tggctaagtc gttggttcaa aatgctttaa gacctcataa gatcgttctt    720
cacatcataa cggataggaa aacttatttc ccaatgcaag cttggttctc attgcatcct    780
ctgtctccag caataattga ggtcaaggct ttgcatcatt tcgattggtt atcgaaaggt    840
aaagtacccg ttttggaagc tatggagaaa gatcagagag tgaggtctca attcagaggt    900
ggatcatcgg ttattgtggc taataacaaa gagaacccgg ttgttgttgc tgctaagtta    960
caagctctca gccctaaata caactccttg atgaatcaca tccgtattca tctaccagag   1020
ttgtttccaa gcttaaacaa ggttgtgttt ctagacgatg acattgtgat ccaaactgat   1080
ctttcacctc tttgggacat tgacatgaat ggaaaagtaa atggagcagt ggaaacatgt   1140
agaggagaag acaagtttgt gatgtcaaag aagttcaaga gttacctcaa cttctcgaat   1200
ccgacaattg ccaaaaactt caatccagag gaatgtgcat gggcttatgg aatgaatgtt   1260
ttcgacctag cggcttggag gaggactaac ataagctcca cttactatca ttggcttgac   1320
gagaacttaa atcagacct gagtttgtgg cagctgggaa ctttgcctcc tgggctgatt   1380
gctttccacg tcatgtcca accatagat ccgttctggc atatgcttgg tctcggatac   1440
caagagacca cgagctatgc cgatgctgaa agtgccgctg ttgttcattt caatggaaga   1500
gctaagcctt ggctggatat agcatttcct catctacgtc ctctctgggc taagtatctt   1560
gattcttctg acagatttat caagagctgt cacattagag catcatga              1608
```

<210> SEQ ID NO 30
<211> LENGTH: 535
<212> TYPE: PRT
<213> ORGANISM: Arabidopsis thaliana

<400> SEQUENCE: 30

```
Met Gln Leu His Ile Ser Pro Ser Leu Arg His Val Thr Val Thr
  1               5                  10                  15

Gly Lys Gly Leu Arg Glu Phe Ile Lys Val Lys Val Gly Ser Arg Arg
             20                  25                  30

Phe Ser Tyr Gln Met Val Phe Tyr Ser Leu Leu Phe Phe Thr Phe Leu
         35                  40                  45

Leu Arg Phe Val Phe Val Leu Ser Thr Val Asp Thr Ile Asp Gly Asp
     50                  55                  60

Pro Ser Pro Cys Ser Ser Leu Ala Cys Leu Gly Lys Arg Leu Lys Pro
 65                  70                  75                  80

Lys Leu Leu Gly Arg Arg Val Asp Ser Gly Asn Val Pro Glu Ala Met
                 85                  90                  95

Tyr Gln Val Leu Glu Gln Pro Leu Ser Glu Gln Glu Leu Lys Gly Arg
            100                 105                 110

Ser Asp Ile Pro Gln Thr Leu Gln Asp Phe Met Ser Glu Val Lys Arg
        115                 120                 125

Ser Lys Ser Asp Ala Arg Glu Phe Ala Gln Lys Leu Lys Glu Met Val
    130                 135                 140

Thr Leu Met Glu Gln Arg Thr Arg Thr Ala Lys Ile Gln Glu Tyr Leu
145                 150                 155                 160

Tyr Arg His Val Ala Ser Ser Ser Ile Pro Lys Gln Leu His Cys Leu
                165                 170                 175

Ala Leu Lys Leu Ala Asn Glu His Ser Ile Asn Ala Ala Arg Leu
            180                 185                 190

Gln Leu Pro Glu Ala Glu Leu Val Pro Met Leu Val Asp Asn Asn Tyr
        195                 200                 205
```

```
Phe His Phe Val Leu Ala Ser Asp Asn Ile Leu Ala Ala Ser Val Val
    210                 215                 220

Ala Lys Ser Leu Val Gln Asn Ala Leu Arg Pro His Lys Ile Val Leu
225                 230                 235                 240

His Ile Ile Thr Asp Arg Lys Thr Tyr Phe Pro Met Gln Ala Trp Phe
                245                 250                 255

Ser Leu His Pro Leu Ser Pro Ala Ile Ile Glu Val Lys Ala Leu His
            260                 265                 270

His Phe Asp Trp Leu Ser Lys Gly Lys Val Pro Val Leu Glu Ala Met
        275                 280                 285

Glu Lys Asp Gln Arg Val Arg Ser Gln Phe Arg Gly Gly Ser Ser Val
290                 295                 300

Ile Val Ala Asn Asn Lys Glu Asn Pro Val Val Ala Ala Lys Leu
305                 310                 315                 320

Gln Ala Leu Ser Pro Lys Tyr Asn Ser Leu Met Asn His Ile Arg Ile
                325                 330                 335

His Leu Pro Glu Leu Phe Pro Ser Leu Asn Lys Val Val Phe Leu Asp
            340                 345                 350

Asp Asp Ile Val Ile Gln Thr Asp Leu Ser Pro Leu Trp Asp Ile Asp
        355                 360                 365

Met Asn Gly Lys Val Asn Gly Ala Val Glu Thr Cys Arg Gly Glu Asp
370                 375                 380

Lys Phe Val Met Ser Lys Lys Phe Lys Ser Tyr Leu Asn Phe Ser Asn
385                 390                 395                 400

Pro Thr Ile Ala Lys Asn Phe Asn Pro Glu Glu Cys Ala Trp Ala Tyr
                405                 410                 415

Gly Met Asn Val Phe Asp Leu Ala Ala Trp Arg Arg Thr Asn Ile Ser
            420                 425                 430

Ser Thr Tyr Tyr His Trp Leu Asp Glu Asn Leu Lys Ser Asp Leu Ser
        435                 440                 445

Leu Trp Gln Leu Gly Thr Leu Pro Pro Gly Leu Ile Ala Phe His Gly
450                 455                 460

His Val Gln Thr Ile Asp Pro Phe Trp His Met Leu Gly Leu Gly Tyr
465                 470                 475                 480

Gln Glu Thr Thr Ser Tyr Ala Asp Ala Glu Ser Ala Ala Val Val His
                485                 490                 495

Phe Asn Gly Arg Ala Lys Pro Trp Leu Asp Ile Ala Phe Pro His Leu
            500                 505                 510

Arg Pro Leu Trp Ala Lys Tyr Leu Asp Ser Ser Asp Arg Phe Ile Lys
        515                 520                 525

Ser Cys His Ile Arg Ala Ser
    530                 535

<210> SEQ ID NO 31
<211> LENGTH: 1086
<212> TYPE: DNA
<213> ORGANISM: Arabidopsis thaliana

<400> SEQUENCE: 31
atgcattgga ttacgagatt ctctgctttc ttctccgccg cattagccat gattctcctt    60
tctccttcgc tccaatcctt ttctccggcg gcagctatcc gatcatctca ccctacgcc    120 gacgaattca aacccaaca aaactccgat tactcctcct tcagagaatc tccaatgttc    180
cgtaacgccg aacaatgcag atcttccggc gaagattccg gcgtctgtaa ccctaatctc    240
```

```
gtccacgtag ccatcactct cgacatcgat tacctccgtg gctcaatcgc agccgtcaat    300
tcgatcctcc agcactcaat gtgccctcaa agcgtcttct tccacttcct cgtctcctcc    360
gagtctcaaa acctagaatc tctgattcgt tctactttcc ccaaattgac gaatctcaaa    420
atttactatt ttgcccctga gaccgtacag tctttgattt catcttccgt gagacaagcc    480
ctagagcaac cgttgaatta cgccagaaat tacttggcgg atctgctcga gccttgcgtt    540
aagcgagtca tctacttgga ttcggatctc gtcgtcgtcg atgatatcgt caagctttgg    600
aaaacgggtt taggccagag aacaatcgga gctccggagt attgtcacgc gaatttcacg    660
aaatacttca ccggaggttt ttggtcagat aagaggttta acgggacgtt caaagggagg    720 aaccccttgtt acttcaatac tggtgtaatg gtgattgatt tgaagaagtg gagacaattt    780
aggttcacga aacgaattga gaaatggatg gagattcaga agatagagag gatttatgag    840
cttggttctc ttcctccgtt tcttctggta tttgctggtc atgtagctcc gatttcacat    900
cggtggaatc aacatgggct tggtggtgat aatgttagag gtagttgccg tgatttgcat    960
tctggtcctg tgagtttgct tcactggtca ggtagtggta agccatggtt aagactcgat   1020
tccaagcttc catgtccttt agacacattg tgggcacctt atgatttgta taaacactcc   1080
cattga                                                              1086
```

<210> SEQ ID NO 32
<211> LENGTH: 361
<212> TYPE: PRT
<213> ORGANISM: Arabidopsis thaliana

<400> SEQUENCE: 32

```
Met His Trp Ile Thr Arg Phe Ser Ala Phe Ser Ala Ala Leu Ala
1               5                   10                  15

Met Ile Leu Leu Ser Pro Ser Leu Gln Ser Phe Ser Pro Ala Ala Ala
            20                  25                  30

Ile Arg Ser Ser His Pro Tyr Ala Asp Glu Phe Lys Pro Gln Gln Asn
        35                  40                  45

Ser Asp Tyr Ser Ser Phe Arg Glu Ser Pro Met Phe Arg Asn Ala Glu
    50                  55                  60

Gln Cys Arg Ser Ser Gly Glu Asp Ser Gly Val Cys Asn Pro Asn Leu
65                  70                  75                  80

Val His Val Ala Ile Thr Leu Asp Ile Asp Tyr Leu Arg Gly Ser Ile
                85                  90                  95

Ala Ala Val Asn Ser Ile Leu Gln His Ser Met Cys Pro Gln Ser Val
            100                 105                 110

Phe Phe His Phe Leu Val Ser Ser Glu Ser Gln Asn Leu Glu Ser Leu
        115                 120                 125

Ile Arg Ser Thr Phe Pro Lys Leu Thr Asn Leu Lys Ile Tyr Tyr Phe
    130                 135                 140

Ala Pro Glu Thr Val Gln Ser Leu Ile Ser Ser Val Arg Gln Ala
145                 150                 155                 160

Leu Glu Gln Pro Leu Asn Tyr Ala Arg Asn Tyr Leu Ala Asp Leu Leu
                165                 170                 175

Glu Pro Cys Val Lys Arg Val Ile Tyr Leu Asp Ser Asp Leu Val Val
            180                 185                 190

Val Asp Asp Ile Val Lys Leu Trp Lys Thr Gly Leu Gly Gln Arg Thr
        195                 200                 205

Ile Gly Ala Pro Glu Tyr Cys His Ala Asn Phe Thr Lys Tyr Phe Thr
```

```
          210                 215                 220
Gly Gly Phe Trp Ser Asp Lys Arg Phe Asn Gly Thr Phe Lys Gly Arg
225                 230                 235                 240

Asn Pro Cys Tyr Phe Asn Thr Gly Val Met Val Ile Asp Leu Lys Lys
                245                 250                 255

Trp Arg Gln Phe Arg Phe Thr Lys Arg Ile Glu Lys Trp Met Glu Ile
            260                 265                 270

Gln Lys Ile Glu Arg Ile Tyr Glu Leu Gly Ser Leu Pro Pro Phe Leu
        275                 280                 285

Leu Val Phe Ala Gly His Val Ala Pro Ile Ser His Arg Trp Asn Gln
    290                 295                 300

His Gly Leu Gly Gly Asp Asn Val Arg Gly Ser Cys Arg Asp Leu His
305                 310                 315                 320

Ser Gly Pro Val Ser Leu Leu His Trp Ser Gly Ser Gly Lys Pro Trp
                325                 330                 335

Leu Arg Leu Asp Ser Lys Leu Pro Cys Pro Leu Asp Thr Leu Trp Ala
            340                 345                 350

Pro Tyr Asp Leu Tyr Lys His Ser His
        355                 360

<210> SEQ ID NO 33
<211> LENGTH: 1038
<212> TYPE: DNA
<213> ORGANISM: Arabidopsis thaliana

<400> SEQUENCE: 33
atgtcttctc tgcgtttgcg tttatgtctt cttctactct tacctatcac aattagctgc    60
gtcacagtca ctctcactga cctccccgcg tttcgtgaag ctccggcgtt tcgaaacggc   120
agagaatgct ccaaaacgac atggatacct tcggatcacg aacacaaccc atcaatcatc   180
cacatcgcta tgactctcga cgcaatttac ctccgtggct cagtcgccgg cgtcttctcc   240
gttctccaac acgcttcttg tcctgaaaac atcgttttcc acttcatcgc cactcaccgt   300
cgcagcgccg atccgccg cataatctcc tcaacattcc catacctaac ctaccacatt   360
taccattttg accctaacct cgtccgcagc aaaatatctt cctctattcg tcgtgcttta   420
gaccaaccgt taaactacgc tcggatctac ctcgccgatc tcctcccaat cgccgtccgc   480
cgcgtaatct acttcgactc cgatctcgta gtcgtcgatg acgtggctaa actctggaga   540
atcgatctac gtcggcacgt cgtcggagct ccggagtact gtcacgcgaa tttcactaac   600
tacttcactt caagattctg gtcgagtcaa ggttacaaat cggcgttgaa agataggaaa   660
ccgtgttatt tcaacaccgg agtgatggtg attgatctcg gaaaatggag agaaaggaga   720
gtcacggtga agctagagac atggatgagg attcaaaaac gacatcgtat ttacgaattg   780
ggatctttgc ctccgtttct gctcgttttc gccggagatg ttgagccggt ggagcatagg   840
tggaatcagc atggtcttgg tggtgataac ttggaaggac tttgccggaa tttgcatcca   900
ggtccggtga gtttgttgca ttggagcggg aaagggaaac catggctaag gcttgactcg   960
agacgaccgt gtccgttgga ttcgttatgg gctccttatg atttgtttcg ttattcaccg  1020
ttgatctctg atagctga                                                1038

<210> SEQ ID NO 34
<211> LENGTH: 345
<212> TYPE: PRT
<213> ORGANISM: Arabidopsis thaliana
```

<400> SEQUENCE: 34

```
Met Ser Ser Leu Arg Leu Arg Leu Cys Leu Leu Leu Leu Pro Ile
1               5                   10                  15

Thr Ile Ser Cys Val Thr Val Thr Leu Thr Asp Leu Pro Ala Phe Arg
            20                  25                  30

Glu Ala Pro Ala Phe Arg Asn Gly Arg Glu Cys Ser Lys Thr Thr Trp
            35                  40                  45

Ile Pro Ser Asp His Glu His Asn Pro Ser Ile Ile His Ile Ala Met
            50                  55                  60

Thr Leu Asp Ala Ile Tyr Leu Arg Gly Ser Val Ala Gly Val Phe Ser
65                  70                  75                  80

Val Leu Gln His Ala Ser Cys Pro Glu Asn Ile Val Phe His Phe Ile
                85                  90                  95

Ala Thr His Arg Arg Ser Ala Asp Leu Arg Arg Ile Ile Ser Ser Thr
                100                 105                 110

Phe Pro Tyr Leu Thr Tyr His Ile Tyr His Phe Asp Pro Asn Leu Val
            115                 120                 125

Arg Ser Lys Ile Ser Ser Ile Arg Arg Ala Leu Asp Gln Pro Leu
130                 135                 140

Asn Tyr Ala Arg Ile Tyr Leu Ala Asp Leu Leu Pro Ile Ala Val Arg
145                 150                 155                 160

Arg Val Ile Tyr Phe Asp Ser Asp Leu Val Val Asp Asp Val Ala
                165                 170                 175

Lys Leu Trp Arg Ile Asp Leu Arg Arg His Val Gly Ala Pro Glu
            180                 185                 190

Tyr Cys His Ala Asn Phe Thr Asn Tyr Phe Thr Ser Arg Phe Trp Ser
                195                 200                 205

Ser Gln Gly Tyr Lys Ser Ala Leu Lys Asp Arg Lys Pro Cys Tyr Phe
    210                 215                 220

Asn Thr Gly Val Met Val Ile Asp Leu Gly Lys Trp Arg Glu Arg Arg
225                 230                 235                 240

Val Thr Val Lys Leu Glu Thr Trp Met Arg Ile Gln Lys Arg His Arg
                245                 250                 255

Ile Tyr Glu Leu Gly Ser Leu Pro Pro Phe Leu Leu Val Phe Ala Gly
            260                 265                 270

Asp Val Glu Pro Val Glu His Arg Trp Asn Gln His Gly Leu Gly Gly
        275                 280                 285

Asp Asn Leu Glu Gly Leu Cys Arg Asn Leu His Pro Gly Pro Val Ser
        290                 295                 300

Leu Leu His Trp Ser Gly Lys Gly Lys Pro Trp Leu Arg Leu Asp Ser
305                 310                 315                 320

Arg Arg Pro Cys Pro Leu Asp Ser Leu Trp Ala Pro Tyr Asp Leu Phe
            325                 330                 335

Arg Tyr Ser Pro Leu Ile Ser Asp Ser
            340                 345
```

<210> SEQ ID NO 35
<211> LENGTH: 1056
<212> TYPE: DNA
<213> ORGANISM: Arabidopsis thaliana

<400> SEQUENCE: 35

```
atgtcccaac atcttcttct tctcattctc ctctcgctac ttcttcttca taaacccatt    60
tccgccacta caattattca aaaattcaaa gaagccccac agttttacaa ttctgcagat   120
```

-continued

```
tgccccttaa tcgatgactc cgagtccgac gatgacgtgg tcgccaaacc aatcttctgc      180
tcacgtcgag ctgtccacgt ggcgatgaca ctcgacgccg cctacattcg tggctcagtc      240
gccgctgttc tctccgtcct ccaacactct tcttgtcctg aaaacattgt tttccacttc      300
gtcgcctctg cttccgccga cgcttcttcc ttacgagcca ccatatcctc ctctttccct      360
taccttgatt tcaccgtcta cgtcttcaac gtcctccg tctctcgcct tatctcctcc        420
tctatccgct ccgcactaga ctgtccttta aactacgcaa gaagctacct cgccgatctc      480
ctccctccct gcgtccgccg cgtcgtctac ctagactccg atctgatcct cgtcgacgac      540
atagcaaaac tcgccgccac agatctcggc cgtgattcag tcctcgccgc gccggaatac      600
tgcaacgcca atttcacttc atacttcaca tcaaccttct ggtctaatcc gactctctct      660
ttaaccttcg ccgatcggaa agcatgctac ttcaacactg gagtcatggt gatcgatctt      720
tcccggtggc gcgaaggcgc gtacacgtca cgcatcgaag agtggatggc gatgcaaaag      780
agaatgagaa tttacgagct tggttcgtta ccaccgtttt tattggtttt tgccggtttg      840
attaaaccgg ttaatcatcg gtggaaccaa cacggtttag gaggtgataa tttcagagga      900
ctgtgtagag atctccatcc tggtccggtg agtctgttgc attggagtgg gaaaggtaag      960
ccatgggcta ggcttgatgc tggtcggcct tgtcctttag acgcgctttg ggctccgtat     1020
gatcttcttc aaacgccgtt cgcgttggat tcttga                               1056
```

<210> SEQ ID NO 36
<211> LENGTH: 351
<212> TYPE: PRT
<213> ORGANISM: Arabidopsis thaliana

<400> SEQUENCE: 36

```
Met Ser Gln His Leu Leu Leu Ile Leu Leu Ser Leu Leu Leu Leu
1               5                   10                  15

His Lys Pro Ile Ser Ala Thr Thr Ile Ile Gln Lys Phe Lys Glu Ala
            20                  25                  30

Pro Gln Phe Tyr Asn Ser Ala Asp Cys Pro Leu Ile Asp Asp Ser Glu
        35                  40                  45

Ser Asp Asp Asp Val Val Ala Lys Pro Ile Phe Cys Ser Arg Arg Ala
    50                  55                  60

Val His Val Ala Met Thr Leu Asp Ala Ala Tyr Ile Arg Gly Ser Val
65                  70                  75                  80

Ala Ala Val Leu Ser Val Leu Gln His Ser Ser Cys Pro Glu Asn Ile
                85                  90                  95

Val Phe His Phe Val Ala Ser Ala Ser Ala Asp Ala Ser Ser Leu Arg
            100                 105                 110

Ala Thr Ile Ser Ser Ser Phe Pro Tyr Leu Asp Phe Thr Val Tyr Val
        115                 120                 125

Phe Asn Val Ser Ser Val Ser Arg Leu Ile Ser Ser Ser Ile Arg Ser
    130                 135                 140

Ala Leu Asp Cys Pro Leu Asn Tyr Ala Arg Ser Tyr Leu Ala Asp Leu
145                 150                 155                 160

Leu Pro Pro Cys Val Arg Arg Val Val Tyr Leu Asp Ser Asp Leu Ile
                165                 170                 175

Leu Val Asp Asp Ile Ala Lys Leu Ala Ala Thr Asp Leu Gly Arg Asp
            180                 185                 190

Ser Val Leu Ala Ala Pro Glu Tyr Cys Asn Ala Asn Phe Thr Ser Tyr
        195                 200                 205
```

```
Phe Thr Ser Thr Phe Trp Ser Asn Pro Thr Leu Ser Leu Thr Phe Ala
    210                 215                 220
Asp Arg Lys Ala Cys Tyr Phe Asn Thr Gly Val Met Val Ile Asp Leu
225                 230                 235                 240
Ser Arg Trp Arg Glu Gly Ala Tyr Thr Ser Arg Ile Glu Glu Trp Met
            245                 250                 255
Ala Met Gln Lys Arg Met Arg Ile Tyr Glu Leu Gly Ser Leu Pro Pro
        260                 265                 270
Phe Leu Leu Val Phe Ala Gly Leu Ile Lys Pro Val Asn His Arg Trp
    275                 280                 285
Asn Gln His Gly Leu Gly Gly Asp Asn Phe Arg Gly Leu Cys Arg Asp
290                 295                 300
Leu His Pro Gly Pro Val Ser Leu Leu His Trp Ser Gly Lys Gly Lys
305                 310                 315                 320
Pro Trp Ala Arg Leu Asp Ala Gly Arg Pro Cys Pro Leu Asp Ala Leu
            325                 330                 335
Trp Ala Pro Tyr Asp Leu Leu Gln Thr Pro Phe Ala Leu Asp Ser
        340                 345                 350

<210> SEQ ID NO 37
<211> LENGTH: 1182
<212> TYPE: DNA
<213> ORGANISM: Arabidopsis thaliana

<400> SEQUENCE: 37
atgtcgtcgc gtttttcttt gacggtggtg tgtttgattg ctctgttacc gtttgttgtt      60
ggtatacggt tgattccggc gaggatcacg agtgtcggtg atggcggcgg cggaggaggt     120
aataatgggt ttagtaaact tggtccgttt atggaagctc cggagtatag aaacggcaag     180
gagtgtgtat cttcatcagt gaacagagag aacttcgtgt cgtcttcttc tagttctaat     240
gatccttcgc ttgttcacat cgctatgact ttggactcag agtatctccg tggatcaatc     300
gcagccgttc attctgttct tcgccacgcg tcttgtccag agaacgtctt cttccatttc     360
atcgctgctg agtttgactc tgcgagtcct cgtgttctga gtcaactcgt gaggtcgact     420
tttccttcgt tgaactttaa agtctacatt tttagggaag atacggtgat caatctcata     480
tcttcttcga ttagactagc tttggagaat ccgttgaact atgctcggaa ctatctcgga     540
gatattcttg atcgaagtgt tgaacgagtc atttatcttg actcggatgt tataactgtg     600
gatgatatca caaagctttg gaacacggtt ttgaccgggt cacgagtcat cggagctccg     660
gagtattgtc acgcgaactt cactcagtat ttcacttccg ggttctggtc agacccggct     720
ttaccgggtc taatctcggg tcaaaagcct tgctatttca acacaggagt gatggtgatg     780
gatcttgtta gatggagaga agggaattac agagagaagt tagagcaatg gatgcaattg     840
cagaagaaga tgagaatcta cgatcttgga tcattaccac cgtttctttt ggtgtttgcg     900
ggtaatgttg aagctattga tcatagatgg aaccaacatg gtttaggagg agacaatata     960
cgaggaagtt gtcggtcatt gcatcctggt cctgtgagct tgttgcattg gagtggtaaa    1020
ggtaagccat gggttagact tgatgagaag aggccttgtc cgttggatca tctttgggag    1080
ccatatgatt tgtataagca taagattgag agagctaaag atcagtctct gcttgggttt    1140
gcttctctgt cggagttgac tgatgattca agcttcttgt ga                        1182

<210> SEQ ID NO 38
<211> LENGTH: 393
```

```
<212> TYPE: PRT
<213> ORGANISM: Arabidopsis thaliana

<400> SEQUENCE: 38

Met Ser Ser Arg Phe Ser Leu Thr Val Val Cys Leu Ile Ala Leu Leu
1               5                   10                  15

Pro Phe Val Val Gly Ile Arg Leu Ile Pro Ala Arg Ile Thr Ser Val
            20                  25                  30

Gly Asp Gly Gly Gly Gly Gly Asn Asn Gly Phe Ser Lys Leu Gly
        35                  40                  45

Pro Phe Met Glu Ala Pro Glu Tyr Arg Asn Gly Lys Glu Cys Val Ser
    50                  55                  60

Ser Ser Val Asn Arg Glu Asn Phe Val Ser Ser Ser Ser Ser Ser Asn
65                  70                  75                  80

Asp Pro Ser Leu Val His Ile Ala Met Thr Leu Asp Ser Glu Tyr Leu
                85                  90                  95

Arg Gly Ser Ile Ala Ala Val His Ser Val Leu Arg His Ala Ser Cys
            100                 105                 110

Pro Glu Asn Val Phe Phe His Phe Ile Ala Ala Glu Phe Asp Ser Ala
        115                 120                 125

Ser Pro Arg Val Leu Ser Gln Leu Val Arg Ser Thr Phe Pro Ser Leu
    130                 135                 140

Asn Phe Lys Val Tyr Ile Phe Arg Glu Asp Thr Val Ile Asn Leu Ile
145                 150                 155                 160

Ser Ser Ser Ile Arg Leu Ala Leu Glu Asn Pro Leu Asn Tyr Ala Arg
                165                 170                 175

Asn Tyr Leu Gly Asp Ile Leu Asp Arg Ser Val Glu Arg Val Ile Tyr
            180                 185                 190

Leu Asp Ser Asp Val Ile Thr Val Asp Asp Ile Thr Lys Leu Trp Asn
        195                 200                 205

Thr Val Leu Thr Gly Ser Arg Val Ile Gly Ala Pro Glu Tyr Cys His
    210                 215                 220

Ala Asn Phe Thr Gln Tyr Phe Thr Ser Gly Phe Trp Ser Asp Pro Ala
225                 230                 235                 240

Leu Pro Gly Leu Ile Ser Gly Gln Lys Pro Cys Tyr Phe Asn Thr Gly
                245                 250                 255

Val Met Val Met Asp Leu Val Arg Trp Arg Glu Gly Asn Tyr Arg Glu
            260                 265                 270

Lys Leu Glu Gln Trp Met Gln Leu Gln Lys Lys Met Arg Ile Tyr Asp
        275                 280                 285

Leu Gly Ser Leu Pro Pro Phe Leu Leu Val Phe Ala Gly Asn Val Glu
    290                 295                 300

Ala Ile Asp His Arg Trp Asn Gln His Gly Leu Gly Gly Asp Asn Ile
305                 310                 315                 320

Arg Gly Ser Cys Arg Ser Leu His Pro Gly Pro Val Ser Leu Leu His
                325                 330                 335

Trp Ser Gly Lys Gly Lys Pro Trp Val Arg Leu Asp Glu Lys Arg Pro
            340                 345                 350

Cys Pro Leu Asp His Leu Trp Glu Pro Tyr Asp Leu Tyr Lys His Lys
        355                 360                 365

Ile Glu Arg Ala Lys Asp Gln Ser Leu Leu Gly Phe Ala Ser Leu Ser
    370                 375                 380

Glu Leu Thr Asp Asp Ser Ser Phe Leu
385                 390
```

-continued

<210> SEQ ID NO 39
<211> LENGTH: 1173
<212> TYPE: DNA
<213> ORGANISM: Arabidopsis thaliana

<400> SEQUENCE: 39

| | |
|---|---:|
| atgcggttgc gttttccgat gaaatctgcc gttttagcgt ttgctatctt tctggtgttt | 60 |
| attccactgt tttccgtcgg tatacggatg attccgggaa gactcaccgc cgtatccgcc | 120 |
| accgtcggaa atggctttga tctggggtcg ttcgtggaag ctccggagta cagaaacggc | 180 |
| aaggagtgcg tgtctcaatc gttgaacaga gaaaacttcg tgtcgtcttg cgacgcttcg | 240 |
| ttagttcatg tagctatgac gcttgactcg gagtacttac gtggctcaat cgcagccgta | 300 |
| cattcaatgc tccgccacgc gtcgtgtcca gaaaacgtct tcttccatct catcgctgca | 360 |
| gagtttgacc cggcgagtcc acgcgttctg agtcaactcg tccgatctac tttcccgtcg | 420 |
| ctaaacttca aagtctacat tttccgggaa gatacggtga tcaaccttat ctcttcttca | 480 |
| atcagacaag ctttagagaa tccattgaac tatgctcgga actacctcgg agatattctt | 540 |
| gatccatgcg tagacagagt catttaccta gactcggaca tcatcgtcgt cgatgacata | 600 |
| acaaagcttt ggaacacgag tttgacaggg tcaagaatca tcggagctcc ggagtattgt | 660 |
| cacgctaact tcacaaagta cttcacttca ggtttctggt ccgacccggc tttacccggt | 720 |
| ttcttctcgg tcgaaagcc ttgttatttc aacacgggtg tgatggtgat ggatctagtt | 780 |
| agatggagag aaggaaacta cagagaaaag cttgaaactt ggatgcagat acagaagaag | 840 |
| aagagaatct acgatttggg ttctttgcct ccgtttcttc ttgtcttcgc agggaacgtt | 900 |
| gaagcaattg atcataggtg gaaccaacat ggtttaggag agacaatgt acgaggaagt | 960 |
| tgtaggtctt tgcataaagg accagtgagt tgttgcatt ggagtggtaa aggtaagcca | 1020 |
| tgggtgagac ttgatgagaa gagaccgtgt ccgttggatc atttatggga accgtatgat | 1080 |
| ttatatgagc ataagattga aagagctaaa gatcagtctt tgttcgggtt ctcttctttg | 1140 |
| tctgagttaa cagaagattc aagcttttc tga | 1173 |

<210> SEQ ID NO 40
<211> LENGTH: 390
<212> TYPE: PRT
<213> ORGANISM: Arabidopsis thaliana

<400> SEQUENCE: 40

Met Arg Leu Arg Phe Pro Met Lys Ser Ala Val Leu Ala Phe Ala Ile
1               5                   10                  15

Phe Leu Val Phe Ile Pro Leu Phe Ser Val Gly Ile Arg Met Ile Pro
            20                  25                  30

Gly Arg Leu Thr Ala Val Ser Ala Thr Val Gly Asn Gly Phe Asp Leu
        35                  40                  45

Gly Ser Phe Val Glu Ala Pro Glu Tyr Arg Asn Gly Lys Glu Cys Val
    50                  55                  60

Ser Gln Ser Leu Asn Arg Glu Asn Phe Val Ser Cys Asp Ala Ser
65                  70                  75                  80

Leu Val His Val Ala Met Thr Leu Asp Ser Glu Tyr Leu Arg Gly Ser
                85                  90                  95

Ile Ala Ala Val His Ser Met Leu Arg His Ala Ser Cys Pro Glu Asn
            100                 105                 110

Val Phe Phe His Leu Ile Ala Ala Glu Phe Asp Pro Ala Ser Pro Arg

```
              115                 120                 125
Val Leu Ser Gln Leu Val Arg Ser Thr Phe Pro Ser Leu Asn Phe Lys
    130                 135                 140

Val Tyr Ile Phe Arg Glu Asp Thr Val Ile Asn Leu Ile Ser Ser Ser
145                 150                 155                 160

Ile Arg Gln Ala Leu Glu Asn Pro Leu Asn Tyr Ala Arg Asn Tyr Leu
                165                 170                 175

Gly Asp Ile Leu Asp Pro Cys Val Asp Arg Val Ile Tyr Leu Asp Ser
            180                 185                 190

Asp Ile Ile Val Asp Asp Ile Thr Lys Leu Trp Asn Thr Ser Leu
        195                 200                 205

Thr Gly Ser Arg Ile Ile Gly Ala Pro Glu Tyr Cys His Ala Asn Phe
    210                 215                 220

Thr Lys Tyr Phe Thr Ser Gly Phe Trp Ser Asp Pro Ala Leu Pro Gly
225                 230                 235                 240

Phe Phe Ser Gly Arg Lys Pro Cys Tyr Phe Asn Thr Gly Val Met Val
                245                 250                 255

Met Asp Leu Val Arg Trp Arg Glu Gly Asn Tyr Arg Glu Lys Leu Glu
            260                 265                 270

Thr Trp Met Gln Ile Gln Lys Lys Lys Arg Ile Tyr Asp Leu Gly Ser
    275                 280                 285

Leu Pro Pro Phe Leu Leu Val Phe Ala Gly Asn Val Glu Ala Ile Asp
    290                 295                 300

His Arg Trp Asn Gln His Gly Leu Gly Gly Asp Asn Val Arg Gly Ser
305                 310                 315                 320

Cys Arg Ser Leu His Lys Gly Pro Val Ser Leu Leu His Trp Ser Gly
                325                 330                 335

Lys Gly Lys Pro Trp Val Arg Leu Asp Glu Lys Arg Pro Cys Pro Leu
            340                 345                 350

Asp His Leu Trp Glu Pro Tyr Asp Leu Tyr Glu His Lys Ile Glu Arg
        355                 360                 365

Ala Lys Asp Gln Ser Leu Phe Gly Phe Ser Ser Leu Ser Glu Leu Thr
    370                 375                 380

Glu Asp Ser Ser Phe Phe
385                 390

<210> SEQ ID NO 41
<211> LENGTH: 1056
<212> TYPE: DNA
<213> ORGANISM: Arabidopsis thaliana

<400> SEQUENCE: 41
atggcctcaa ggagcctctc ctatacacaa ctcctaggcc tcctgtcctt tatactcctc      60
ttggtcacaa ccaccactat ggcggttcgt gttggagtca ttcttcataa gccttctgct     120
ccaactcttc ctgttttcag agaagccccg gcttttcgaa acggtgatca atgcgggact     180
cgtgaggctg atcagattca tatcgccatg actctcgaca caaactacct ccgtggcaca     240
atggctgccg ttttgtctct ccttcaacat tccacttgcc ctgaaaacct ctcttttcat     300
ttcctgtccc ttcctcattt cgaaaacgac cttttcacca gcatcaaatc aacctttcct     360
tacctaaact tcaagattta tcagtttgat ccaaacctcg tccgcagcaa gatatcgaaa     420
tccatcaggc aagcccttga tcagcctctt aactacgcaa gaatctacct cgcggatatc     480
atccctagca gcgttgacag gatcatctac ttagactcag acctcgttgt ggtagacgac     540
```

-continued

```
atagagaagc tgtggcatgt ggagatggaa ggtaaagtgg tggctgctcc cgagtactgc      600
cacgcaaact tcacccatta tttcacaaga actttctggt cagacccggt attggtcaaa      660
gttcttgaag gaaaacgtcc gtgttatttc aacacagggg tgatggttgt ggatgtaaac      720
aaatggagga aaggaatgta tacacagaag gtagaagagt ggatgacaat tcagaagcag      780
aagaggatat accatttggg atcattacct ccgtttctgc tgatattcgc cggtgatata      840
aaagcggtta atcataggtg aaccagcat ggtctaggag gtgataattt cgaaggaaga      900
tgtagaacgt tgcatccggg accgataagt cttcttcact ggagtggaaa agggaagcca      960
tggttaagac tagattcaag gaagccttgt atcgttgatc atctatgggc accgtatgat     1020
ctgtaccgtt catcaagaca ttcattagaa gagtag                              1056
```

<210> SEQ ID NO 42
<211> LENGTH: 351
<212> TYPE: PRT
<213> ORGANISM: Arabidopsis thaliana

<400> SEQUENCE: 42

```
Met Ala Ser Arg Ser Leu Ser Tyr Thr Gln Leu Leu Gly Leu Leu Ser
1               5                   10                  15

Phe Ile Leu Leu Leu Val Thr Thr Thr Met Ala Val Arg Val Gly
            20                  25                  30

Val Ile Leu His Lys Pro Ser Ala Pro Thr Leu Pro Val Phe Arg Glu
        35                  40                  45

Ala Pro Ala Phe Arg Asn Gly Asp Gln Cys Gly Thr Arg Glu Ala Asp
    50                  55                  60

Gln Ile His Ile Ala Met Thr Leu Asp Thr Asn Tyr Leu Arg Gly Thr
65                  70                  75                  80

Met Ala Ala Val Leu Ser Leu Gln His Ser Thr Cys Pro Glu Asn
                85                  90                  95

Leu Ser Phe His Phe Leu Ser Leu Pro His Phe Glu Asn Asp Leu Phe
            100                 105                 110

Thr Ser Ile Lys Ser Thr Phe Pro Tyr Leu Asn Phe Lys Ile Tyr Gln
        115                 120                 125

Phe Asp Pro Asn Leu Val Arg Ser Lys Ile Ser Lys Ser Ile Arg Gln
    130                 135                 140

Ala Leu Asp Gln Pro Leu Asn Tyr Ala Arg Ile Tyr Leu Ala Asp Ile
145                 150                 155                 160

Ile Pro Ser Ser Val Asp Arg Ile Ile Tyr Leu Asp Ser Asp Leu Val
                165                 170                 175

Val Val Asp Asp Ile Glu Lys Leu Trp His Val Glu Met Glu Gly Lys
            180                 185                 190

Val Val Ala Ala Pro Glu Tyr Cys His Ala Asn Phe Thr His Tyr Phe
        195                 200                 205

Thr Arg Thr Phe Trp Ser Asp Pro Val Leu Val Lys Val Leu Glu Gly
    210                 215                 220

Lys Arg Pro Cys Tyr Phe Asn Thr Gly Val Met Val Asp Val Asn
225                 230                 235                 240

Lys Trp Arg Lys Gly Met Tyr Thr Gln Lys Val Glu Glu Trp Met Thr
                245                 250                 255

Ile Gln Lys Gln Lys Arg Ile Tyr His Leu Gly Ser Leu Pro Pro Phe
            260                 265                 270

Leu Leu Ile Phe Ala Gly Asp Ile Lys Ala Val Asn His Arg Trp Asn
        275                 280                 285
```

```
Gln His Gly Leu Gly Gly Asp Asn Phe Glu Gly Arg Cys Arg Thr Leu
    290                 295                 300

His Pro Gly Pro Ile Ser Leu Leu His Trp Ser Gly Lys Gly Lys Pro
305                 310                 315                 320

Trp Leu Arg Leu Asp Ser Arg Lys Pro Cys Ile Val Asp His Leu Trp
                325                 330                 335

Ala Pro Tyr Asp Leu Tyr Arg Ser Ser Arg His Ser Leu Glu Glu
            340                 345                 350

<210> SEQ ID NO 43
<211> LENGTH: 1098
<212> TYPE: DNA
<213> ORGANISM: Arabidopsis thaliana

<400> SEQUENCE: 43
atgatgtctg gttcaagatt agcctctaga ctaataataa tcttctcaat aatctccaca      60
tctttcttca ccgttgaatc gattcgacta ttccctgatt cattcgacga tgcatcttca     120
gatttaatgg aagctccagc atatcaaaac ggtcttgatt gctctgtttt agccaaaaac     180
agactcttgt tagcttgtga tccatcagct gttcatatag ctatgactct agatccagct     240
tacttgcgtg gcacggtatc tgcagtacat tccatcctca aacacacttc ttgccctgaa     300
aacatcttct tccacttcat tgcttcgggt acaagtcagg gttccctcgc caagacccta     360
tcctctgttt ttccttcttt gagtttcaaa gtctatacct tgaagaaac cacggtcaag      420 aatctaatct cttcttctat aagacaagct cttgatagtc ctttgaatta cgcaagaagc     480
tacttatccg agattctttc ttcgtgtgtt agtcgagtga tttatctcga ttcggatgtg     540
attgtggtcg atgatattca gaaactatgg aagatttctt tatccgggtc aagaacaatc     600
ggtgcaccag tgtattgcca cgcaaatttc accaaatact tcacagatag tttctggtcc     660
gatcaaaaac tctcgagtgt cttcgattcc aagactcctt gttatttcaa cacaggagtg     720
atggttatcg atttagagcg atggagagaa ggagattaca cgagaaagat cgaaaactgg     780
atgaagattc agaaagaaga taagagaatc tacgaattgg gttctttacc accgtttctt     840
ctagtgtttg gtggtgatat tgaagctatt gatcatcaat ggaaccaaca cggtctcggt     900
ggagacaaca ttgtgagtag ttgtagatct ttgcatcctg gtccggttag tttgatacat     960
tggagtggta agggaagcc atgggttagg cttgatgatg gtaagccttg tccaattgat     1020
tatctttggg ctcctatga tcttcacaag tcacagaggc agtatcttca atacaatcaa     1080
gagttagaaa ttctttga                                                  1098

<210> SEQ ID NO 44
<211> LENGTH: 365
<212> TYPE: PRT
<213> ORGANISM: Arabidopsis thaliana

<400> SEQUENCE: 44

Met Met Ser Gly Ser Arg Leu Ala Ser Arg Leu Ile Ile Ile Phe Ser
1               5                   10                  15

Ile Ile Ser Thr Ser Phe Phe Thr Val Glu Ser Ile Arg Leu Phe Pro
            20                  25                  30

Asp Ser Phe Asp Asp Ala Ser Ser Asp Leu Met Glu Ala Pro Ala Tyr
        35                  40                  45

Gln Asn Gly Leu Asp Cys Ser Val Leu Ala Lys Asn Arg Leu Leu Leu
    50                  55                  60
```

-continued

```
Ala Cys Asp Pro Ser Ala Val His Ile Ala Met Thr Leu Asp Pro Ala
 65                  70                  75                  80

Tyr Leu Arg Gly Thr Val Ser Ala Val His Ser Ile Leu Lys His Thr
                 85                  90                  95

Ser Cys Pro Glu Asn Ile Phe Phe His Phe Ile Ala Ser Gly Thr Ser
            100                 105                 110

Gln Gly Ser Leu Ala Lys Thr Leu Ser Ser Val Phe Pro Ser Leu Ser
        115                 120                 125

Phe Lys Val Tyr Thr Phe Glu Glu Thr Thr Val Lys Asn Leu Ile Ser
130                 135                 140

Ser Ser Ile Arg Gln Ala Leu Asp Ser Pro Leu Asn Tyr Ala Arg Ser
145                 150                 155                 160

Tyr Leu Ser Glu Ile Leu Ser Ser Cys Val Ser Arg Val Ile Tyr Leu
                165                 170                 175

Asp Ser Asp Val Ile Val Asp Asp Ile Gln Lys Leu Trp Lys Ile
            180                 185                 190

Ser Leu Ser Gly Ser Arg Thr Ile Gly Ala Pro Glu Tyr Cys His Ala
        195                 200                 205

Asn Phe Thr Lys Tyr Phe Thr Asp Ser Phe Trp Ser Asp Gln Lys Leu
    210                 215                 220

Ser Ser Val Phe Asp Ser Lys Thr Pro Cys Tyr Phe Asn Thr Gly Val
225                 230                 235                 240

Met Val Ile Asp Leu Glu Arg Trp Arg Glu Gly Asp Tyr Thr Arg Lys
                245                 250                 255

Ile Glu Asn Trp Met Lys Ile Gln Lys Glu Asp Lys Arg Ile Tyr Glu
            260                 265                 270

Leu Gly Ser Leu Pro Pro Phe Leu Leu Val Phe Gly Gly Asp Ile Glu
        275                 280                 285

Ala Ile Asp His Gln Trp Asn Gln His Gly Leu Gly Gly Asp Asn Ile
    290                 295                 300

Val Ser Ser Cys Arg Ser Leu His Pro Gly Pro Val Ser Leu Ile His
305                 310                 315                 320

Trp Ser Gly Lys Gly Lys Pro Trp Val Arg Leu Asp Asp Gly Lys Pro
                325                 330                 335

Cys Pro Ile Asp Tyr Leu Trp Ala Pro Tyr Asp Leu His Lys Ser Gln
            340                 345                 350

Arg Gln Tyr Leu Gln Tyr Asn Gln Glu Leu Glu Ile Leu
        355                 360                 365

<210> SEQ ID NO 45
<211> LENGTH: 1026
<212> TYPE: DNA
<213> ORGANISM: Arabidopsis thaliana

<400> SEQUENCE: 45
atgcactcga agtttatatt atatctcagc atcctcgccg tattcaccgt ctctttcgcc      60
ggcggcgaga gattcaaaga agctccaaag ttcttcaact ccccggagtg tctaaccatc     120
gaaaacgatg aagatttcgt tgttcagac aaagccatcc acgtggcaat gaccttagac     180
acagcttacc tccgtggctc aatggccgtg attctctccg cctccaacac ctcttcttgt     240
cctcaaaaca ttgttttcca cttcgtcact tcaaaacaaa gccaccgact ccaaaactac     300
gtcgttgctt cttttcccta cttgaaattc cgaattacc cttacgacgt agccgccatc     360
tccggcctca tctcaacctc catccgctcc gcgctagact ctccgctaaa ctacgcaaga     420
```

```
aactacctcg ccgacattct tcccacgtgc ctctcacgtg tcgtatacct agactcagat    480
ctcatactcg tcgatgacat ctccaagctc ttctccactc acatccctac cgacgtcgtt    540
ttagccgcgc ctgagtactg caacgcaaac ttcacgactt actttactcc gacgttttgg    600
tcaaacccct tctctctccat cacactatcc ctcaaccgcc gtgctacacc gtgttacttc    660
aacaccggag tgatggtcat cgagttaaag aaatggcgag aaggagatta cacgaggaag    720
atcatagagt ggatggagtt acaaaaacgg ataagaatct acgagttagg ctctttacca    780 ccgttttttac ttgtcttcgc cggaaacata gctccggtag atcaccggtg aaccaacac    840 ggtttaggag gagataattt tagaggactg tgtcgagatt tgcatccagg tccagtgagt    900
ttgttgcatt ggagtgggaa agggaagcca tgggtaaggt tagatgatgg tcgaccttgc    960
ccgcttgatg cactttgggt tccatatgat ttgttagagt cacggttcga ccttatcgag    1020
agttaa                                                                1026

<210> SEQ ID NO 46
<211> LENGTH: 341
<212> TYPE: PRT
<213> ORGANISM: Arabidopsis thaliana

<400> SEQUENCE: 46

Met His Ser Lys Phe Ile Leu Tyr Leu Ser Ile Leu Ala Val Phe Thr
1               5                   10                  15

Val Ser Phe Ala Gly Gly Glu Arg Phe Lys Glu Ala Pro Lys Phe Phe
            20                  25                  30

Asn Ser Pro Glu Cys Leu Thr Ile Glu Asn Asp Glu Asp Phe Val Cys
        35                  40                  45

Ser Asp Lys Ala Ile His Val Ala Met Thr Leu Asp Thr Ala Tyr Leu
    50                  55                  60

Arg Gly Ser Met Ala Val Ile Leu Ser Val Leu Gln His Ser Ser Cys
65                  70                  75                  80

Pro Gln Asn Ile Val Phe His Phe Val Thr Ser Lys Gln Ser His Arg
                85                  90                  95

Leu Gln Asn Tyr Val Val Ala Ser Phe Pro Tyr Leu Lys Phe Arg Ile
            100                 105                 110

Tyr Pro Tyr Asp Val Ala Ala Ile Ser Gly Leu Ile Ser Thr Ser Ile
        115                 120                 125

Arg Ser Ala Leu Asp Ser Pro Leu Asn Tyr Ala Arg Asn Tyr Leu Ala
    130                 135                 140

Asp Ile Leu Pro Thr Cys Leu Ser Arg Val Val Tyr Leu Asp Ser Asp
145                 150                 155                 160

Leu Ile Leu Val Asp Asp Ile Ser Lys Leu Phe Ser Thr His Ile Pro
                165                 170                 175

Thr Asp Val Val Leu Ala Ala Pro Glu Tyr Cys Asn Ala Asn Phe Thr
            180                 185                 190

Thr Tyr Phe Thr Pro Thr Phe Trp Ser Asn Pro Ser Leu Ser Ile Thr
        195                 200                 205

Leu Ser Leu Asn Arg Arg Ala Thr Pro Cys Tyr Phe Asn Thr Gly Val
    210                 215                 220

Met Val Ile Glu Leu Lys Lys Trp Arg Glu Gly Asp Tyr Thr Arg Lys
225                 230                 235                 240

Ile Ile Glu Trp Met Glu Leu Gln Lys Arg Ile Arg Ile Tyr Glu Leu
                245                 250                 255

Gly Ser Leu Pro Pro Phe Leu Leu Val Phe Ala Gly Asn Ile Ala Pro
```

```
                260                 265                 270
Val Asp His Arg Trp Asn Gln His Gly Leu Gly Gly Asp Asn Phe Arg
            275                 280                 285

Gly Leu Cys Arg Asp Leu His Pro Gly Pro Val Ser Leu Leu His Trp
        290                 295                 300

Ser Gly Lys Gly Lys Pro Trp Val Arg Leu Asp Asp Gly Arg Pro Cys
305                 310                 315                 320

Pro Leu Asp Ala Leu Trp Val Pro Tyr Asp Leu Glu Ser Arg Phe
                325                 330                 335

Asp Leu Ile Glu Ser
        340

<210> SEQ ID NO 47
<211> LENGTH: 1086
<212> TYPE: DNA
<213> ORGANISM: Arabidopsis thaliana

<400> SEQUENCE: 47
atgctttgga tcatgagatt ctccggttta ttctccgccg ctttggttat catcgtcctc        60
tctccttctc tccaatcgtt tcctccagct gaagctatca gatcctctca tctcgacgct       120
tacctccgtt tcccctcctc cgatccaccg ccgcatagat tctcccttcag aaaagctcct      180 gttttccgca atgccgccga ttgcgccgcc gcagatatcg attccggcgt ctgtaaccct       240
tccttggtcc acgtcgcgat tactctcgat ttcgagtacc tgcgtggctc aatcgccgcc       300
gttcattcga ttctcaagca ctcgtcgtgt cccgagagcg tcttcttcca tttcctcgtc       360
tccgagactg acctagaatc cttgattcgt tcgacttttc ccgaattgaa attaaaggtt       420
tactacttcg atccggagat tgtacggacg ctgatctcaa cctccgtgag acaagcgctc       480
gagcagccgt tgaattacgc tagaaattac ctagctgacc ttctcgagcc ttgcgtgcgt       540
cgcgtgatct acctagattc cgatctaatc gtcgtcgacg acatcgcaaa gctctggatg       600
acgaaactgg gatcgaaaac gatcggagct cccgagtact gtcacgcgaa cttcacaaag       660
tatttcacac cggcgttctg gtccgacgag aggttctccg gagctttctc cgggaggaaa       720
ccgtgctact tcaacacggg agtgatggtg atggatctag agagatggag gcgcgtaggg       780
tacacggagg tgatagagaa atggatggag attcagaaga gtgataggat ttacgagctg       840
ggatcattgc cgccgttctt gttggtgttc gccggagaag tagctccgat agagcatcgg       900
tggaaccagc atgggcttgg tggagataac gtgagaggaa gctgtagaga tttacatccc       960
ggtccggtta gcttgcttca ttggtccggt agtggtaaac cgtggtttcg gttagattcg      1020
agacggcctt gtccacttga tactctttgg gcaccttatg atttgtatgg acactactct      1080
cgctga                                                                 1086

<210> SEQ ID NO 48
<211> LENGTH: 361
<212> TYPE: PRT
<213> ORGANISM: Arabidopsis thaliana

<400> SEQUENCE: 48

Met Leu Trp Ile Met Arg Phe Ser Gly Leu Phe Ser Ala Ala Leu Val
1               5                   10                  15

Ile Ile Val Leu Ser Pro Ser Leu Gln Ser Phe Pro Pro Ala Glu Ala
            20                  25                  30

Ile Arg Ser Ser His Leu Asp Ala Tyr Leu Arg Phe Pro Ser Ser Asp
        35                  40                  45
```

```
Pro Pro Pro His Arg Phe Ser Phe Arg Lys Ala Pro Val Phe Arg Asn
         50                  55                  60
Ala Ala Asp Cys Ala Ala Asp Ile Asp Ser Gly Val Cys Asn Pro
 65              70                  75                  80
Ser Leu Val His Val Ala Ile Thr Leu Asp Phe Glu Tyr Leu Arg Gly
                 85                  90                  95
Ser Ile Ala Ala Val His Ser Ile Leu Lys His Ser Ser Cys Pro Glu
            100                 105                 110
Ser Val Phe Phe His Phe Leu Val Ser Glu Thr Asp Leu Glu Ser Leu
            115                 120                 125
Ile Arg Ser Thr Phe Pro Glu Leu Lys Leu Lys Val Tyr Tyr Phe Asp
        130                 135                 140
Pro Glu Ile Val Arg Thr Leu Ile Ser Thr Ser Val Arg Gln Ala Leu
145                 150                 155                 160
Glu Gln Pro Leu Asn Tyr Ala Arg Asn Tyr Leu Ala Asp Leu Leu Glu
                165                 170                 175
Pro Cys Val Arg Arg Val Ile Tyr Leu Asp Ser Asp Leu Ile Val Val
            180                 185                 190
Asp Asp Ile Ala Lys Leu Trp Met Thr Lys Leu Gly Ser Lys Thr Ile
        195                 200                 205
Gly Ala Pro Glu Tyr Cys His Ala Asn Phe Thr Lys Tyr Phe Thr Pro
210                 215                 220
Ala Phe Trp Ser Asp Glu Arg Phe Ser Gly Ala Phe Ser Gly Arg Lys
225                 230                 235                 240
Pro Cys Tyr Phe Asn Thr Gly Val Met Val Met Asp Leu Glu Arg Trp
                245                 250                 255
Arg Arg Val Gly Tyr Thr Glu Val Ile Glu Lys Trp Met Glu Ile Gln
            260                 265                 270
Lys Ser Asp Arg Ile Tyr Glu Leu Gly Ser Leu Pro Pro Phe Leu Leu
        275                 280                 285
Val Phe Ala Gly Glu Val Ala Pro Ile Glu His Arg Trp Asn Gln His
    290                 295                 300
Gly Leu Gly Gly Asp Asn Val Arg Gly Ser Cys Arg Asp Leu His Pro
305                 310                 315                 320
Gly Pro Val Ser Leu Leu His Trp Ser Gly Ser Gly Lys Pro Trp Phe
                325                 330                 335
Arg Leu Asp Ser Arg Arg Pro Cys Pro Leu Asp Thr Leu Trp Ala Pro
            340                 345                 350
Tyr Asp Leu Tyr Gly His Tyr Ser Arg
        355                 360

<210> SEQ ID NO 49
<211> LENGTH: 1041
<212> TYPE: DNA
<213> ORGANISM: Arabidopsis thaliana

<400> SEQUENCE: 49
atgctttgga taacgagatt tgctggatta ttctccgccg cgatggcagt gatcgtgtta    60
tctccgtcgc ttcagtcatt tcctccggcg gcggcaatcc gttcttctcc atcaccgatc   120
ttcagaaaag ctccagcggt gttcaacaac ggcgacgaat gtctctcctc cggcggcgtc   180
tgcaatccgt cgttggtcca cgtggcgatc acgttagacg tagagtacct gcgtggctca   240
atcgcagccg ttaactcgat ccttcagcac tcggtgtgtc cagagagcgt cttcttccac   300
```

-continued

```
ttcatcgccg tctccgagga aacaaacctg ttggagtcgc tggtgagatc ggttttcccg      360
agactgaaat tcaatattta cgattttgcc cctgagacag ttcgtggttt gatttcttct      420
tccgtgagac aagctctcga gcagcctctg aactacgcta gaagctactt agcggatctg      480
ctggagcctt gtgttaaccg tgtcatatac ttggattcgg atcttgtcgt cgtcgatgac      540
atcgctaagc tttggaaaac tagcctaggc tcgaggataa tcggagctcc ggagtattgt      600
cacgcgaatt tcacgaaata cttcaccgga ggattctggt cggaggagag attctccggt      660
acctttagag ggaggaagcc atgttacttc aacacaggtg tgatggtgat agatcttaag      720
aaatggagaa gaggtggtta cacgaaacgt atcgagaaat ggatggagat tcagagaaga      780
gagaggattt acgaactagg ctcgcttcca ccgtttcttc tagttttctc cggtcacgtg      840
gctcccatct ctcaccggtg gaaccagcat ggacttggtg gtgacaatgt tagaggtagc      900
tgtcgtgatt tgcatcctgg tcctgtgagt ttgctgcatt ggtctggtag tggcaagccc      960
tggataagac tcgattccaa acggccttgt cccttagacg cattatggac gccttacgac     1020
ttgtatcgac attcgcattg a                                               1041
```

<210> SEQ ID NO 50
<211> LENGTH: 346
<212> TYPE: PRT
<213> ORGANISM: Arabidopsis thaliana

<400> SEQUENCE: 50

```
Met Leu Trp Ile Thr Arg Phe Ala Gly Leu Phe Ser Ala Ala Met Ala
1               5                   10                  15

Val Ile Val Leu Ser Pro Ser Leu Gln Ser Phe Pro Pro Ala Ala Ala
            20                  25                  30

Ile Arg Ser Ser Pro Ser Pro Ile Phe Arg Lys Ala Pro Ala Val Phe
        35                  40                  45

Asn Asn Gly Asp Glu Cys Leu Ser Ser Gly Val Cys Asn Pro Ser
    50                  55                  60

Leu Val His Val Ala Ile Thr Leu Asp Val Glu Tyr Leu Arg Gly Ser
65                  70                  75                  80

Ile Ala Ala Val Asn Ser Ile Leu Gln His Ser Val Cys Pro Glu Ser
                85                  90                  95

Val Phe Phe His Phe Ile Ala Val Ser Glu Glu Thr Asn Leu Leu Glu
            100                 105                 110

Ser Leu Val Arg Ser Val Phe Pro Arg Leu Lys Phe Asn Ile Tyr Asp
        115                 120                 125

Phe Ala Pro Glu Thr Val Arg Gly Leu Ile Ser Ser Val Arg Gln
    130                 135                 140

Ala Leu Glu Gln Pro Leu Asn Tyr Ala Arg Ser Tyr Leu Ala Asp Leu
145                 150                 155                 160

Leu Glu Pro Cys Val Asn Arg Val Ile Tyr Leu Asp Ser Asp Leu Val
                165                 170                 175

Val Val Asp Asp Ile Ala Lys Leu Trp Lys Thr Ser Leu Gly Ser Arg
            180                 185                 190

Ile Ile Gly Ala Pro Glu Tyr Cys His Ala Asn Phe Thr Lys Tyr Phe
        195                 200                 205

Thr Gly Gly Phe Trp Ser Glu Glu Arg Phe Ser Gly Thr Phe Arg Gly
    210                 215                 220

Arg Lys Pro Cys Tyr Phe Asn Thr Gly Val Met Val Ile Asp Leu Lys
225                 230                 235                 240
```

-continued

```
Lys Trp Arg Arg Gly Gly Tyr Thr Lys Arg Ile Glu Lys Trp Met Glu
            245                 250                 255

Ile Gln Arg Arg Glu Arg Ile Tyr Glu Leu Gly Ser Leu Pro Pro Phe
            260                 265                 270

Leu Leu Val Phe Ser Gly His Val Ala Pro Ile Ser His Arg Trp Asn
        275                 280                 285

Gln His Gly Leu Gly Gly Asp Asn Val Arg Gly Ser Cys Arg Asp Leu
    290                 295                 300

His Pro Gly Pro Val Ser Leu Leu His Trp Ser Gly Ser Gly Lys Pro
305                 310                 315                 320

Trp Ile Arg Leu Asp Ser Lys Arg Pro Cys Pro Leu Asp Ala Leu Trp
            325                 330                 335

Thr Pro Tyr Asp Leu Tyr Arg His Ser His
            340                 345
```

NUCLEIC ACIDS ENCODING A GALACTURONOSYL TRANFERASE ENZYME (GALAT1) FROM *ARABIDOPSIS*

CROSS REFERENCE TO RELATED APPLICATIONS

The present application claims benefit of U.S. Provisional Patent Application No. 60/445,539 filed Feb. 6, 2003, which is incorporated in its entirety herein by reference to the extent not inconsistent herewith.

STATEMENT REGARDING FEDERALLY SPONSORED RESEARCH OR DEVELOPMENT

This invention was made at least in part with U.S. Government support under USDA 98-35304-6772 and USDA 2001-03351. The Government has certain rights in this invention.

BACKGROUND

This invention relates to plant physiology, growth, development, defense and, in particular, to plant genes, termed galacturonosyltransferases (GALATs), nucleic acids encoding same and the uses therefor.

Pectins are the most complex polysaccharides in the plant cell wall. They comprise 30-40% of the primary wall of dicots and non-graminaceous monocots, and ~10% of the primary wall in the grass family. Pectins are a family of polysaccharides[6,8,27] that include homogalacturonan (HGA) (FIG. 1), rhamnogalacturonan-I (RG-I) (FIG. 2) and rhamnogalacturonan II (RG-II) (FIG. 3) as well as xylogalacturonans (XGA)[32,34,38] and apiogalacturonans.[6,37] While the specific structure of each of these polysaccharides differs as shown in FIGS. 1-3, they are grouped into one family since they appear to be linked to each other in the wall and they each contain α-D-galacturonic acid connected by a 1,4-linkage.

HGA is the most abundant pectic polysaccharide, accounting for ~55%-70% of pectin[39]. HGA is a linear homopolymer of α1,4-linked D-galactosyluronic acid that is partially methylesterified at the C6 carboxyl group and may be partially acetylated at O-2 and/or O-3[8] (FIG. 1). Some plants also contain HGA that is substituted at the 2 or 3 position by D-apiofuranose, the so-called apiogalacturonans (AGA)[36,37] and/or HGA that is substituted at the 3 position with D-xylose[32-35], so-called xylogalacturonan (XGA). RG-II is a complex polysaccharide that accounts for approximately 10-11% of pectin[8,39]. RG-II has an HGA backbone with four structurally complex side chains attached to C-2 and/or C-3 of the GalA[8,27] (FIG. 3). Rhamnogalacturonan I (RG-I) accounts for 20-35% of pectin[39] (FIG. 2). RG-I is a family of polysaccharides with an alternating [→4)-α-D-GalA-(1→2)-α-L-Rha-(1→] backbone in which roughly 20-80% of the rhamnoses are substituted by arabinan, galactan, or arabinogalactan side branches[6,8,30].

Pectins are believed to have multiple roles during plant growth, development, and in plant defense responses. For example, pectic polysaccharides play essential roles in cell wall structure[43], cell adhesion[44] and cell signaling[45,46]. Pectins also appear to mediate pollen tube growth[47] and to have roles during seed hydration[48,49], leaf abscission[50], water movement[51], and fruit development[47,8]. Oligosaccharides cleaved from pectin also serve as signals to induce plant defense responses[52,53]. Studies of mutant plants with altered wall pectin reveal that modifications of pectin structure leads to dwarfed plants[43], brittle leaves[44], reduced numbers of side shoots and flowers[54], malformed stomata[44] and reduced cell adhesion[55].

Although pectins appear to have multiple roles in plants, in no case has their specific mechanism of action been determined. One way to directly test the biological roles of pectins, and to study their mechanisms of action, is to produce plants with specific alterations in pectin structure. This can be done by knocking out genes that encode the pectin biosynthetic enzymes. Such enzymes include the nucleotide-sugar biosynthetic enzymes and the glycosyltransferases that synthesize the pectic polysaccharides. Each glycosyltransferase is expected to transfer a unique glycosyl residue in a specific linkage onto a specific polymeric/oligomeric acceptor. To date, only five[56-59,136] of the more than 200 predicted wall biosynthetic glycosyltransferases have been funtionally identified at the gene level (i.e. enzyme activity of the gene product proven), and none of these have been shown to encode pectin biosynthetic enzymes.

Based on the known structure of pectin, at least 58 distinct glycosyl-, methyl- and acetyl-transferases are believed to be required to synthesize the family of polymers known as pectin. As shown in the review by Mohnen, D. (2002) "Pectins and their Manipulation", G. B. Seymour et al., Blackwell Publishing and CRC Press, Oxford, England, pp. 52-98, and Table I below, a minimum of 4-9 galacturonosyltranferases are predicted to be required for the synthesis of HGA, RG-I, RG-II and possibly for the synthesis of the modified forms of HGA known as XGA and AGA. The present invention relates to the identification of the first gene, GALAT1, encoding a galacturonosyltranferase and related genes thereto. The studies disclosed hereinbelow led the inventors to conclude that the gene GALAT1 encodes the enzyme known as UDP-GalA: Homogalacturonan α-1,4-Galacturonosyltransferase.

TABLE I

List of galacturonosyltransferase activities predicted to be required for pectin biosynthesis[9]

| Type of GalAT | Working[1] Number | Parent polymer[2] | Enzyme[3] | | Ref for Structure |
|---|---|---|---|---|---|
| | | | Acceptor substrate | Enzyme activity | |
| D-GalAT | 1 | HGA | *GalAα1→4GalA | α1,4-GalAT | 27 |
| D-GalAT | 2 | RG-I | L-Rhaα1→4GalA | α1,2-GalAT | 27-29 |
| D-GalAT | 3 | RG-II | L-Rhaβ1→3Apif | α1,2-GalAT | 30, 31 |

TABLE I-continued

List of galacturonosyltransferase activities predicted to be required for pectin biosynthesis[9]

| Type of GalAT | Working[1] Number | Parent polymer[2] | Enzyme[3] Acceptor substrate | Enzyme activity | Ref for Structure |
|---|---|---|---|---|---|
| D-GalAT | 4 | RG-II | L-Rhaβ1→3Apif | β1,3GalAT | 30, 31 |
| D-GalAT | 5?[4] | RG-I/HGA | GalAα1→2LRha | α1,4-GalAT | — |
| D-GalAT | 6? | RG-II/HGA | GalAα1→4GalA | α1,4-GalAT | — |
| D-GalAT | 7? | XGA | GalAα1→4(Xyl β1→3)GalA[5] | α1,4-GalAT | 32-35 |
| D-GalAT | 8? | AGA | GalAα1→4(Apif β1→2)GalA | α1,4-GalAT | 36, 37 |
| D-GalAT | 9? | AGA | GalAα1→4(Apif β1→3)GalA | α1,4-GalAT | 36, 37 |

[1]Numbers for different members of the same groups are given based on pectin structure and on the assumption that HGA is synthesized first, followed by RG-I and RG-II. The numbers were given[9] to facilitate a comparison of the enzymes, but final numbering will likely correspond to the order in which the genes are identified.
[2]HGA: homogalacturonan; RG-I: Rhamnogalacturonan I; RG-II: Rhamnogalacturonan II; XGA: Xylogalacturonan; AGA; Apiogalacturonan.
[3]All sugars are D sugars and have pyranose rings unless otherwise indicated. Glycosyltranferases add to the glycosyl residue on the left* of the indicated acceptor.
[4]The ? means the designated GalAT may be required if a different GalAT in the list does not perform the designated function.
[5]Glycosyl residue in the parenthesis is branched off the first GalA.

Over the years, membrane-bound α1-4galacturonosyltransferase (GalAT) activity has been identified and partially characterized in mung bean[10,11], tomato[12], turnip[12], sycamore[13], tobacco suspension[2], radish roots[5], enriched Golgi from pea[7], Azuki bean[14], Petunia[15], and *Arabidopsis* (see Table II). The pea GalAT was found to be localized to the Golgi[7] with its catalytic site facing the lumenal side of the Golgi[7]. These results provided the first direct enzymatic evidence that the synthesis of HGA occurs in the Golgi. In in vitro reactions, GalAT adds [¹⁴C]GalA from UDP-[¹⁴C]GalA[1,60] onto endogenous acceptors in microsomal membrane preparations to produce radiolabeled products of large molecular mass (i.e. ~105 kd in tobacco microsomal membranes[2] and ≧500 kd in pea Golgi[7]). The cleavage of up to 89% of the radiolabeled product into GalA, digalacturonic acid (diGalA) and trigalacturonic acid (triGalA) following exhaustive hydrolysis with a purified endopolygalacturonase confirmed that the product synthesized by tobacco GalAT was largely HGA. Thus, the crude enzyme catalyzes the reaction in vitro: UDP-GalAT+HGA(n)→HGA(n+1)+UDP. The product produced in vitro in tobacco microsomes was ~50% esterified[2] while the product produce in pea Golgi did not appear to be heavily esterified[7]. These results suggest that the degree of methyl esterification of newly synthesized HGA may be species specific and that methylesterification occurs after the synthesis of at least a short stretch of HGA. GalAT in detergent-permeabilized microsomes from azuki bean seedlings added [¹⁴C]GalA from UDP-[¹⁴C]GalA onto acid-soluble polygalacturonate (PGA) exogenous acceptors[14]. Treatment of the radiolabeled product with a purified fungal endopolygalacturonase yielded GalA and diGalA, confirming that the activity identified was a GalAT comparable to that studied in tobacco and pea. The azuki bean enzyme had a surprisingly high specific activity of 1300-2000 pmol mg⁻¹ min⁻¹, especially considering the large amount (3.1-4.1 nmol mg⁻¹ min⁻¹) of polygalacturonase activity that was also present in the microsomal preparations. As with the product-made by tobacco, no evidence for the processive transfer of galactosyluronic acid residues onto the acceptor was obtained (see below).

TABLE II

Comparison of apparent catalytic constants and pH optimum of HGA-α1,4-galacturonosyltransferases[1,2]

| Enzyme[2] | Plant Source | Apparent $K_m$ for UDP-GalA (μM) | pH optimum | Vmax (pmol mg⁻¹ min⁻¹) | Ref |
|---|---|---|---|---|---|
| GalAT[1] | mung bean | 1.7 | 6.0 | ~4700 | 10 |
| GalAT | mung bean | n.d. | n.d. | n.d. | 61 |
| GalAT | pea | n.d.[5] | 6.0 | n.d. | 62 |
| GalAT | pea | n.d. | n.d. | n.d. | 7 |
| GalAT | sycamore | 770 | n.d. | ? | 13 |
| GalAT | tobacco | 8.9 | 7.8 | 150 | 2 |
| GalAT (sol)[3] | tobacco | 37 | 6.3-7.8 | 290 | 3 |
| GalAT (sol)[3] | Petunia | 170 | 7.0 | 480 | 15 |
| GalAT (per)[4] | Azuki bean | 140 | 6.8-7.8 | 2700 | 14 |

[1]Adapted from ref 6.
[2]Unless indicated, all enzymes are measured in particulate preparations.
[3](sol): detergent-solubilized enzyme.
[4](per): detergent-permeabilized enzyme.
[5]n.d.: not determined.

GalAT can be solubilized from membranes with detergent[3]. Solubilized GalAT adds GalA onto the non-reducing end[4] of exogenous HGA (oligogalacturonide; OGA) acceptors of a degree of polymerization of at least ten[2]. The bulk of the HGA elongated in vitro by solubilized GalAT from tobacco membranes[3], or detergent-permeabilized Golgi from pea[7], at roughly equimolar UDP-GalA:acceptor concentrations is elongated by a single GalA residue. These results suggest that solubilized GalAT in vitro acts nonprocessively, (i.e. distributively). The apparent lack of in vitro processivity of GalAT was recently confirmed by Akita et al. who, using pyridylaminated oligogalacturonates as substrates and high concentrations of UDP-GalA, showed that although OGAs can be elongated in a "successive" fashion with up to 10 GalA residues by solubilized enzyme from petunia pollen[15], the kinetics of this response suggest a distributive mode of action. We have two working hypotheses as to why GalAT in vitro does not appear to act processively. One hypothesis is that the solubilized enzyme or the enzyme in particulate preparations does not have the required factors, or is not present in the required complex, to act processively. An alternative hypothesis is that for a Golgi-localized enzyme that synthesizes a complex polymer in a confined internal cellular compartment, such as GalAT, with sufficiently high concentrations of substrate, it would not necessarily be advantageous for the enzyme to act processively. In fact, the reaction velocity could be hindered under such conditions if the enzyme were processive[65].

The apparent kinetic constants and pH optimum for the characterized GalATs are shown in Table II. We have performed additional kinetic studies in tobacco and radish that suggest that solubilized and membrane bound GalAT may have unusual apparent biphasic kinetics. We tested Vo for radish GalAT at 2 µM to 80 mM UDP-GalA and obtained a biphasic curve (FIG. 4), suggesting that the kinetics of GalAT, at least in the membrane and soluble fractions, are complex. Comparable results were also obtained for the solubilized radish and tobacco enzyme. The initial Vo vs [UDP-GalA] curve was hyperbolic and appeared to reach an initial maximum Vo of ~300 pmol $mg^{-1}$ $min^{-1}$ at ~1 mM UDP-GalA, confirming previous results reported for tobacco[2,3]. However, at ≧2 mM UDP-GalA there was a second hyperbolic increase in GalAT activity that reached a maximum of ~2-4 nmol $min^{-1}$ $mg^{-1}$ with ~20 mM UDP-GalA. In crude enzyme preparations it was not possible to determine the basis for the unusual kinetics. One possibility is that two GalATs were present, one with a low Km and one with a high Km. Another possibility is that UDP-GalA is both a substrate and an allosteric regulator of GalAT. Alternatively, a more "trivial" explanation is that at low substrate concentrations the kinetics of GalAT were effected by a catabolic enzyme (e.g. a phosphodiesterase) in the enzyme preparation.

As a first step towards elucidating the role of galacturonosyltransferase (GALAT) in pectin synthesis, the inventors herein identified an *Arabidopsis* gene encoding alpha1,4-galacturonosyltransferase 1 (GALAT1). The database searches using the amino acid sequence of the GALAT1 identified fourteen additional GALAT family members and ten GALAT-like genes. The identification of these genes and the availability of the sequence information allow the characterization of the enzyme, the use of these genes to produce mutated enzymes in vivo and in vitro, and transgenic plants producing modified pectins, and studies of the role of a specific GalAT in pectin synthesis. The advantages of the present invention will become apparent in the following description.

SUMMARY OF THE INVENTION

The present invention provides an isolated nucleic acid molecule encoding the polypeptide having galacturonosyltransferase (GalAT) activity. The GALAT 1 disclosed herein represents the first functionally proven pectin biosynthetic glycosyltransferase gene isolated from plants. Also provided are additional 14 GALAT gene family members and 10 GALAT-like genes predicted to have galacturonosyltransferase activity. The identification and availability of the nucleic acid molecules as a member of the GALAT gene superfamily offer new opportunities to modulate pectin synthesis in vivo and in vitro by modulating the GALAT gene using various art-known recombinant DNA technology. For example, transgenic plants that produce modified pectins of desired properties can be generated by manipulating the gene encoding the GALAT protein i.e., mutating the gene including coding and non-coding sequences, silencing the gene by RNAi approach, or by administering a composition that would affect the GalAT activity in the plant. Since modified pectins are predicted to affect plant growth, development, and plant defense responses, the transgenic plants thus modified are expected to have improved agricultural value. The modified pectins can be isolated from such transgenic plants according to the art-known methods and serve as gelling and stabilizing agents of improved properties in the food, neutraceutical, and pharmaceutical industries.

The inventors herein identified the first gene, GALAT1, which encodes a pectin biosynthetic enzyme by employing a partial purification-tandem mass spectrometry approach combined with a search of the *Arabidopsis* gene/protein database. Two gene products, designated JS33 and JS36 herein, were identified as present only in the GalAT-containing fractions. As demonstrated hereinbelow, the expressed protein from the nucleic acid sequence of JS36 indeed exhibits the predicted GalAT enzymatic activity.

A standard protein blast and a PSI Blast of the NCBI protein database using the GALAT1 (JS36) amino acid sequence revealed that GALAT1 is a member of a 15 member GALAT gene family in *Arabidopsis*. The genes selected for this family have at least 30% amino acid identity and at least 50% amino acid similarity based on the PSI Blast. The database search using the GALAT1 sequence further identified 10 GALAT-like genes as shown in Table IV. The genes disclosed herein, fifteen GALAT genes and ten GALAT-like genes thus represent the GALAT gene superfamily members.

The availability of the amino acid and nucleotide sequences of the GALAT gene superfamily members makes it possible to identify other GALAT homologs in other plants. The nucleotide and amino acid sequences of the GALAT genes can also be used to generate specific antibodies for the protein.

DETAILED DESCRIPTION OF THE INVENTION

Figure 1:
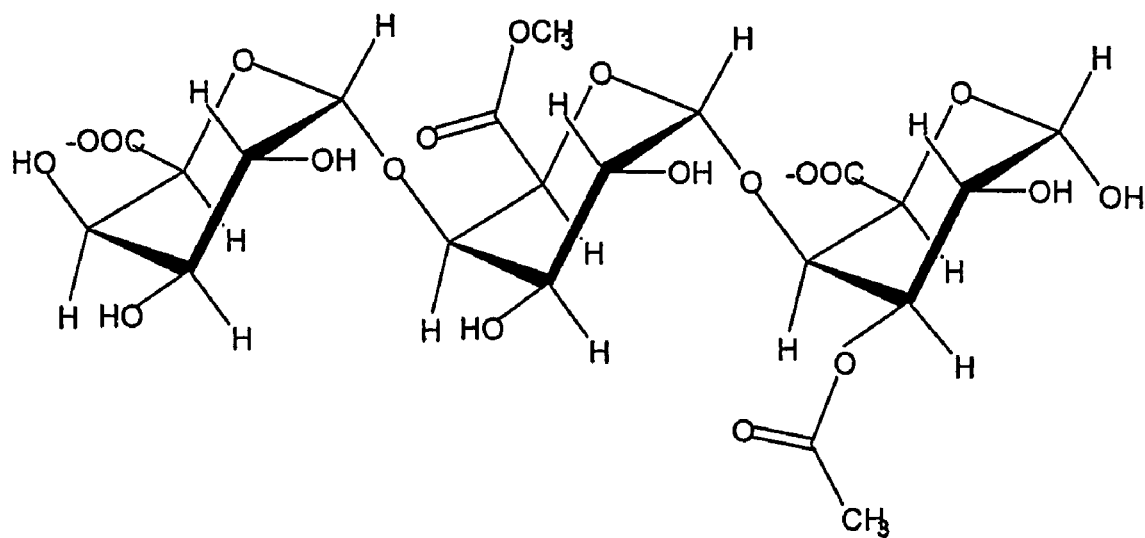
FIG. 1 shows the trimeric region of homogalacturonan (HGA). HGA is a linear homopolymer of alpha-1,4-linked galacturonic acid that may be methylesterified at C6 and acetylated at O2 or O3. Substituted galacturonans, such as RG-II and apiogalacturonan, have an HGA backbone.
Figure 2:
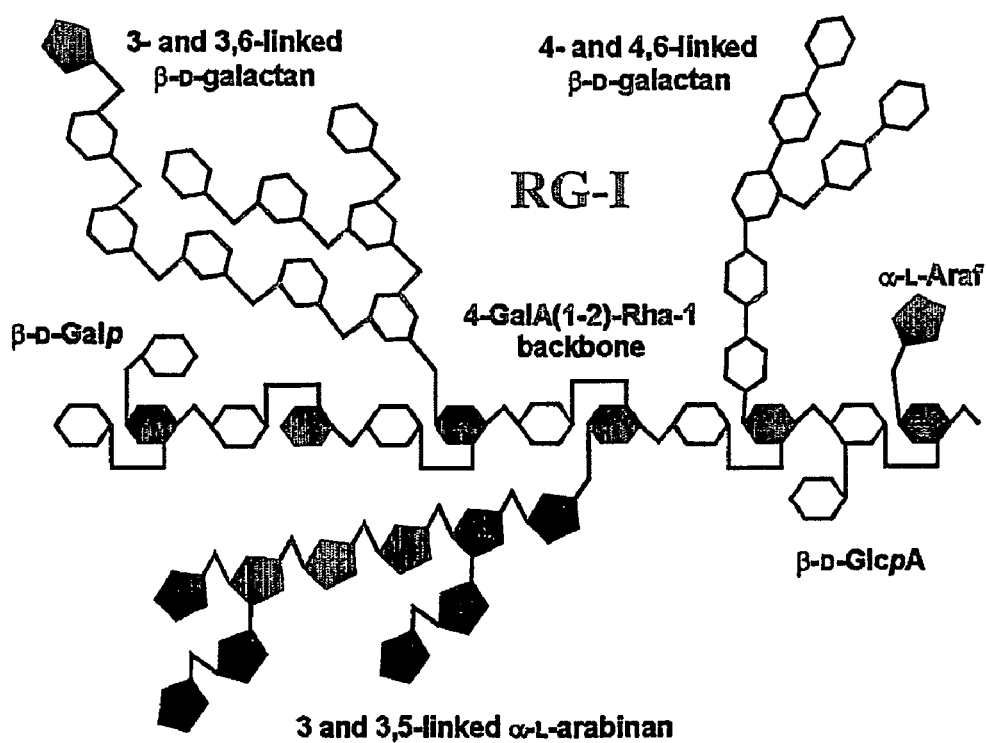
FIG. 2 shows the representative structure of rhamnogalacturonan I (RG-I). RG-I has an alternating [→4)-alpha-D-GalpA-(1→2)-alpha-L-Rhap-(1→) backbone in which roughly 20-80% of the rhamnoses are substituted by arabinans, galactans, or arabinogalactans.
Figure 3:
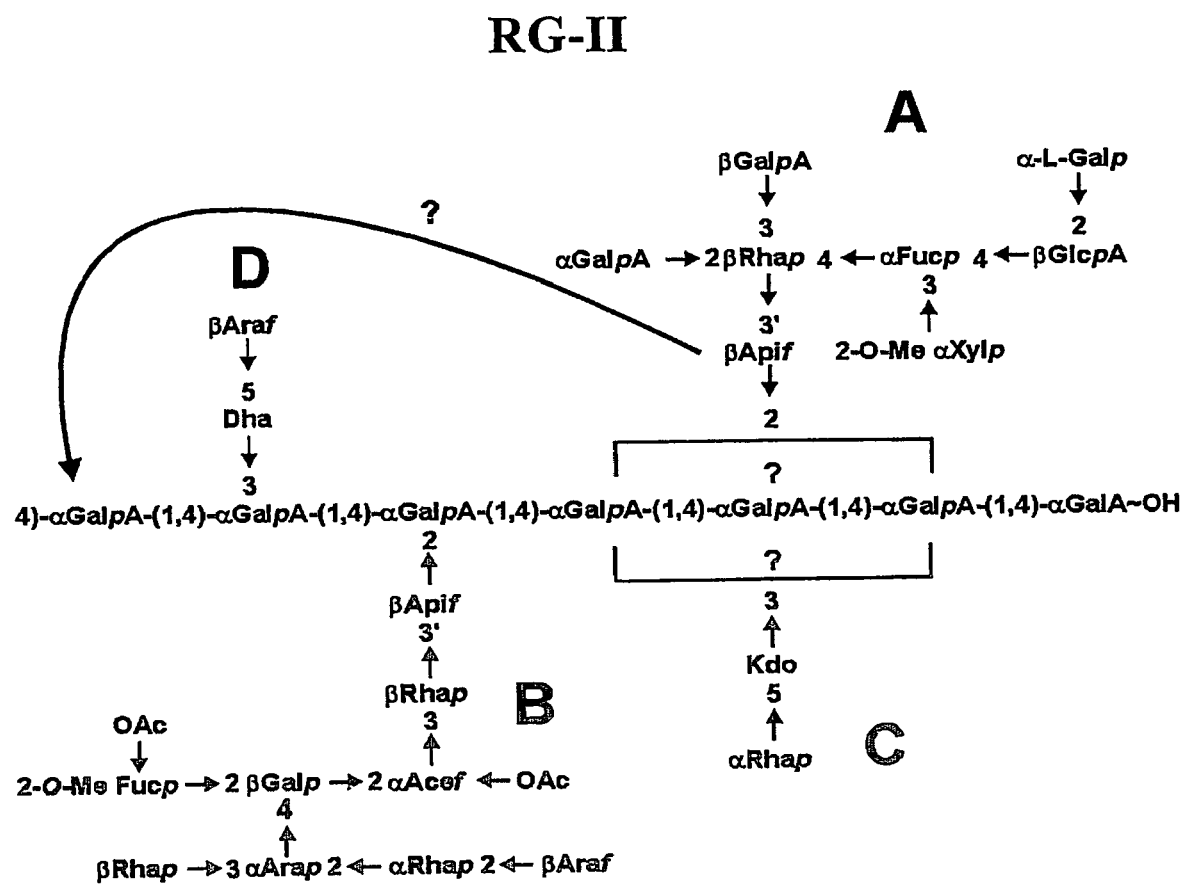
FIG. 3 shows the representative structure for rhamnogalacturonan II (RG-II). RG-II has a backbone of 1,4-linked alpha-D-GalpA residues. GalA residues are also present in RG-II side chain A. Other side chains are denoted B, C and D.
Figure 4:
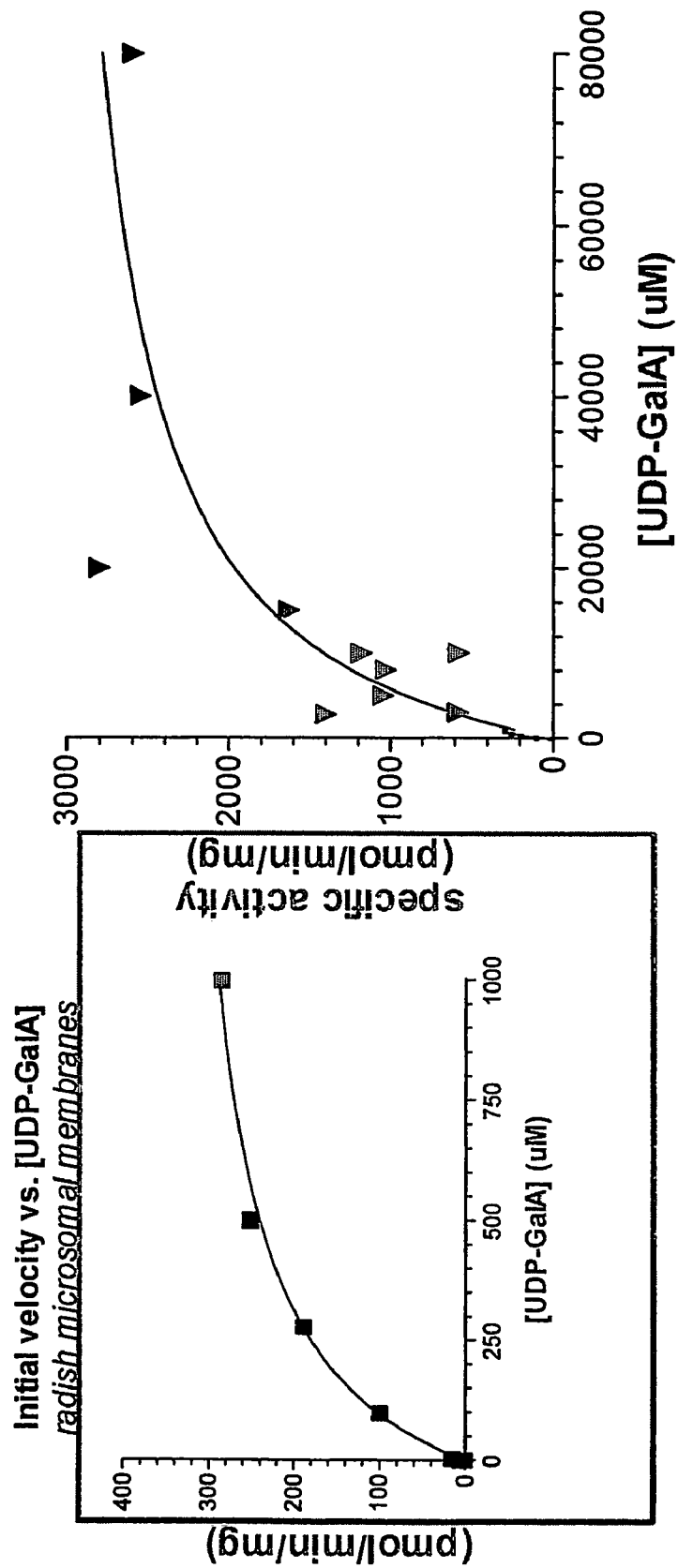
FIG. 4 illustrates the GalAT kinetics in radish microsomal membranes. Radish microsomal membranes (60-80 µg protein) were incubated with 70 µg of OGA (DP 7-23) and the indicated concentrations of UDP-GalA. Each reaction contained a small concentration of UDP-[$^{14}$C]GalA (2-3.6 µM) with larger amounts of nonradioactive UDP-GalA. The precipitated reaction products were measured by liquid scintillation counting. The data are the averages of duplicate samples from three separate experiments. The Y axis is specific activity (pmole $min^{-1}mg^{-1}$).

In general the terms and phrases used herein have their art-recognized meaning, which can be found by reference to standard texts, journal references and contexts known to those skilled in the art. The following definitions are provided to clarify their specific use in the context of the invention.

In the present application, the designation, "GALAT", is used to denote the gene for galacturonosyltransferase, "GALAT" is used to denote the protein encoded by the gene, and "GalAT" is used to indicate galacturonosyltransferase enzyme activity.

The term, "polypeptide", is used herein interchangeably with "protein" to indicate a product encoded by a given nucleic acid.

The terms, "identity" or "similarity" as used herein, are intended to indicate the degree of homology between the two or more nucleic acid or amino acid sequences. The degree of identity or similarity can be determined using any one of the computer programs that are well known in the art. The National Center for Biotechnology Information (NCBI) website on the internet provides detailed description and references necessary for this subject. Also see Karlin and Altschul (1993) *Proc. Natl. Acad. Sci. USA* 90:5873-5877; Altschul et al. (1997) *Nucl. Acids. Res.* 25:3389-3402. In the present application, the percent amino acid identity and similarity among the GALAT gene family and GALAT-like gene family members were carried out using the NCBI Pairwise Blast and Matrix Blosum62 using the GALAT1 (JS 36) amino acid sequence.

A "corresponding" nucleic acid or amino acid or sequence of either, as used herein, is one present at a site in a GALAT molecule or fragment thereof that has the same structure and/or function at a site in another GALAT molecule, although the nucleic acid or amino acid position may not be identical.

The term "gene" is used herein in the broadest context and includes a classical genomic gene consisting of transcriptional and/or translational regulatory sequences and/or a coding region and/or nontranslated sequences (i.e., introns, 5'- and 3'-untranslated sequences), or mRNA or cDNA corresponding to the coding regions (i.e., exons) and 5'- and 3'-untranslated sequences.

The meaning of a "homolog" as used herein is intended to indicate any gene or gene product which has a structural or functional similarity to the gene or gene product in point. For example, a new homolog of a given GALAT gene can be identified either by a database search using the amino acid or nucleic acid sequences of a given GALAT gene or by screening appropriate cDNA or genomic libraries according to the art-known methods.

An "expression vector" as used herein, generally refers to a nucleic acid molecule which is capable of expressing a protein or a nucleic acid molecule of interest in a host cell. Typically, such vectors comprise a promoter sequence (e.g. TATA box, CATTbox, enhancer etc) fused to a heterologous sequence (i.e., a nucleic acid of interest), sense or antisense strand, followed by a transcriptional termination sequence, a selectable marker, and other regulatory sequences necessary for transcription and translation of the nucleic acid of interest. A plant expressible promoter is a promoter comprising all the necessary so called regulatory sequences for transcription and translation of a gene of interest in plants. The linkage between the heterologous sequence and the regulatory sequences (e.g., promoter) is "in operable linkage" when a desired product can be made from the heterologous sequence under the control of the given regulatory sequences. An "expression vector" is often used interchangeably with an "expression construct" in this sense.

The term "transgenic plant" as used herein refers to a plant that has been transformed to contain a heterologous nucleic acid, i.e., a plant expression vector or construct for a desired phenotype. The transgenic plant is intended to include whole plant, plants parts (stems, roots, leaves etc.) or organs, plant cells, seeds, and progeny of same. The transgenic plant having modified pectin of the present application is one that has been generated by manipulating the gene encoding the GALAT protein. This can be achieved, for example, by mutating the gene, silencing the gene by RNAi approach, or by knocking out the gene. The transgenic plants of the invention are predicted to have properties such as changes in organ and plant size, water transport properties, ease of removal of leaves and fruits via effects on abscision, pollen development and release, fruit ripening, root mucilage production, root growth, root cell cap production and separation, stem elongation, shoot growth, flower formation, tuber yield, defense responses against pathogens, and stomata opening[8]. Thus, the invention provides new means of improving plants of agricultural value. The "modified" pectins are those that exhibit structures and properties (e.g., gelling and stabilizing) different from those of the pectins naturally present in plants. Since galacturonic acid is a component of each of the pectic polysaccharides (i.e. HGA, RG-I, RG-II and XGA), a modification of the GalATs that add the specific GalAs into the specific polysaccharides is expected to modify the unique polymers. Such changes in pectin structure would affect multiple pectin properties including ionic interactions between HGA regions, gelation properties, dimer formation of RG-II molecules, length and degree of branching of RG-I, and side branch structure of RG-II. Such modifications are predicted to not only affect the biological function of pectin in plants, and the chemical and biological properties of pectin extracted and used by the food and cosmetic industries, but also properties that affect the use of pectin as a biopolymer for industrial processes, as a drug delivery polymer, and pectins of medicinal and neutraceutical properties in human and animal health.

The term "mutation" as used herein refers to a modification of the natural nucleotide sequence of a nucleic acid molecule made by deleting, substituting, or adding a nucleotide(s) in such a way that the protein encoded by the modified nucleic acid is altered structurally and functionally. The mutation in this sense includes those modifications of a given gene outside of the coding region.

The present invention provides polypeptides and nucleic acids encoding the polypeptides belonging to a family of the pectin biosynthetic enzyme, galacturonosyltransferase (GALAT). Pectins have been implicated in a broad range of plant growth phenomena including pollen tube growth[47], seed hydration[48-49], leaf abscission[50], water movement[128], and fruit development[8]. In addition, pectic oligosaccharides serve as signals[45] during plant development[45] and induce plant defense responses[52-53]. Mutant studies have shown that altered pectin structure leads to dwarfed plants[43], brittle leaves[44], reduced numbers of side shoots and flowers[129], and plants with reduced cell-cell adhesion[130,55]. Therefore, the present invention provides the molecular and biochemical tools needed to identify additional glycosyltransferases involved in branching of the backbones, and would allow the generation of plants with altered pectin structure. While the 25 genes disclosed herein represent only ~0.1% of the ~28,000 genes in *Arabidopsis*, they are some of the most difficult genes to identify and characterize because of a lack of commercially available acceptor substrates and activated glycosyl donor substrates.

The GALAT1 gene has high sequence similarity to proteins expressed in other plants, thus using the sequences disclosed herein, a person of ordinary skill in the art can identify other pectin biosynthetic genes (i.e. homologs) in other plant species, including agriculturally important plants. Since pectin of very similar structure is present in the walls of all flowering plants and gymnosperms, the identification of functional pectin biosynthetic genes will greatly facilitate the engineering of plants with modified pectin and with altered growth characteristics, some of which are expected to yield plants of increased agronomical value. In addition, mutant plants with defined changes in pectin synthesis can allow the dissection of the biological role of each pectic component in plants. The pectin biosynthetic genes provide valuable tools for understanding mechanistically how pectin is synthesized. The glycosyltransferase-specific antibodies that can be generated using the sequences disclosed herein are also within the scope of the invention and allow the process of pectin assembly in the Golgi to be elucidated. A complete understanding of such a polysaccharide cellular trafficking process is unknown in any biological system.

Pectin is found in fruits and vegetables and is used as a gelling and stabilizing agent in the food industry. Pectin has been shown to have multiple beneficial effects on mammalian systems and on human health including the inhibition of cancer growth and metastasis, inhibition of cancer metastasis by binding of pectic oligosaccharides to cell surface receptors of cancer cells (U.S. Pat. Nos. 5,834,442, 5,895,784), immunomodulatory effects and stimulation of tumor necrosis factor by macrophages (EP03983113), interaction with mucous cell lining of the duodenum and the prevention of ulcers (U.S. Pat. Nos. 4,698,229, 6,024,959); and anti-complementary activity[125]. Many cancer cells have specific carbohydrate-binding protein molecules on their cell surfaces called galectins (galactoside-binding lectins). Galectins aid in cellular interactions by binding to beta-galactose linked molecules on neighboring cancer cells. Galectin-3 is a multifunctional lectin that is involved in tumor cell adhesion, metastasis and cancer progression. Blocking galectin-3 expression in malignant human breast, papillary and tongue carcinoma cells led to reversion of the transformed phenotype and suppression of tumor growth in nude mice[117-119]. A pH-modified citrus pectin is suggested to block binding of galectins and inhibit tumor cells adhesion. Pienta et al.[127] showed that feeding of pH-modified pectin to rats caused a reduction in metastasis of prostate cancer. Similarly, oral administration of pectin to mice carrying colon tumors, reduced tumor size compared to control animals[114], reduced metastatic colonization of B16-F1 melanoma in the lung[120-121] and reduced human breast and colon carcinoma growth, angiogenesis, and metastasis[125]. When prostate cancer patients were fed pH-modified citrus pectin, a 30% lengthening in prostate specific antigen (PSA) doubling time was observed in 57% of the patients[122].

As progression of prostate cancer is evaluated based on the time that it takes for the PSA to double, the above observations suggested that pectins may reduce tumor size. It has also been shown that fruit-derived pectins inhibit the interaction of fibroblast growth factor 1 (FGF1) to its receptor (FGFR1)[123]. Defects in the FGF signal transduction system are known to disturb cellular regulatory processes resulting in cancer, cardiovascular disease and diabetes mellitus. The availability of the gene(s) encoding galacturonosyltransferase allows the modification of neutraceutical or pharmaceutical pectins to provide pectins with novel cell and molecule binding activities and thus, with novel and specified anticancer and other physiological activities.

Figure 5:
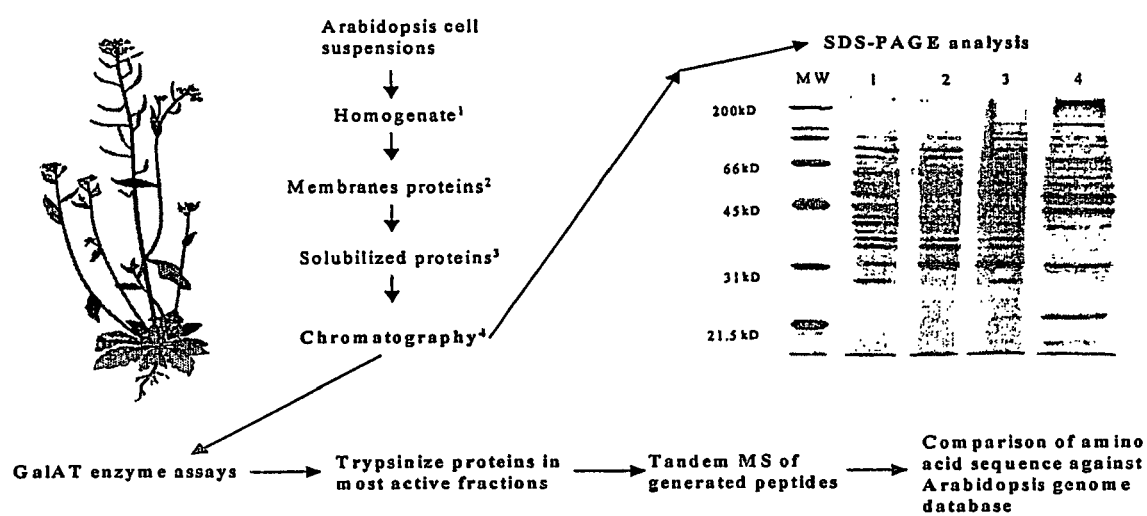
FIG. 5 shows the outline of the strategy to identify the gene for GalAT. The sequenced *Arabidopsis* genome allowed the use of a function-based partial purification-mass spectrometry approach to identify the putative galacturonosyltransferase genes. The sample analyzed in each lane is as follows: lane 1: homogenate, lane 2: total membranes, lane 3: solubilized proteins, lane 4: initial anion exchange purification step.

In order to identify a gene(s) involved in pectin biosynthesis, the inventors used a partial purification-tandem mass spectrometry approach to identify putative GALAT genes from *Arabidopsis* (see FIG. 5 for strategy). GalAT from *Arabidopsis* was partially purified from detergent-solubilized enzyme by sequential passage over two or more of the following resins: cation exchange resin SP-SEPHAROSE, reactive green 19 resin, reactive blue 72 resin, reactive yellow 3 resin, and UDP-agarose. Proteins obtained from selected fractions from these columns were treated with trypsin to generate peptides, and the amino acid sequence of the peptides identified by liquid chromatography-tandem mass spectrometry. The amino sequence thus generated was used to screen the *Arabidopsis* gene/protein database. Thirty unique proteins were solely identified in the GalAT-containing fractions (i.e. not present in fractions not containing GalAT activity). Among the 30 unique proteins that co-purified with GalAT activity, two proteins (designated JS33 and JS36) were initially identified as *Arabidopsis* putative GALAT proteins/genes based on their having at least one predicted transmembrane domain and since they contained a predicted glycosyltransferase domain (see CAZy database; website available as afmb.cnrs.mrc.fr/CASY/index.html).

These two genes, along with another *Arabidopsis* gene with high sequence similarity to JS36 (designated JS36L for JS36-like) (see below) were either cloned by RT-PCR (JS36) using mRNA from *Arabidopsis* flower and stem tissue, or a cDNA clone was obtained from the *Arabidopsis* Biological Resource Center (JS33 and JS36L). The proteins encoded by these genes each have a predicted single transmembrane domain (Table III). The genes were truncated to remove their N-terminal region including all or most of the predicted transmembrane domain (see Table III), and the truncated genes were inserted into a mammalian expression vector pEAK10 (Edge BioSystems as modified by Kelley Moremen lab, CCRC) containing an N-terminal heterologous signal sequence (targeting the protein for secretion into the medium), a polyhistidine (HIS) tag, and two influenza hemagglutinin (HA) epitopes (useful for immunoabsorption).

TABLE III

Predicted characteristics of JS36, JS33 and JS36L proteins. Predictions were made using information from the NCBI database and the SOSUI (Classic & Membrane Prediction program) at BCM Search Launcher site (searchlauncher.bcm.tmc.edu/seq-search/struc-predict.html).

| Gene | NCBI protein ID | # a-mino acids | MW (kd) | pI | Predicted trans-membrane domain | Truncated protein |
|---|---|---|---|---|---|---|
| At3g61130 (JS36) | NP_191672 | 673 | 77.4 | 9.95 | $^N 22\text{-}44^C$ | $^N 42\text{-}673^C$ |
| At2g38650 (JS33) | NP_565893 | 619 | 69.7 | 8.63 | $^N 23\text{-}45^C$ | $^N 44\text{-}619^C$ |

TABLE III-continued

Predicted characteristics of JS36, JS33 and JS36L proteins. Predictions were made using information from the NCBI database and the SOSUI (Classic & Membrane Prediction program) at BCM Search Launcher site (searchlauncher.bcm.tmc.edu/seq-search/struc-predict.html).

| Gene | NCBI protein ID | # a-mino acids | MW (kd) | pI | Predicted trans-membrane domain | Truncated protein |
|---|---|---|---|---|---|---|
| At5g47780 (JS36-like) | NP_568688 | 616 | 71.1 | 9.26 | $^N6\text{-}22^C$ | $^N26\text{-}616^C$ |

Figure 8:
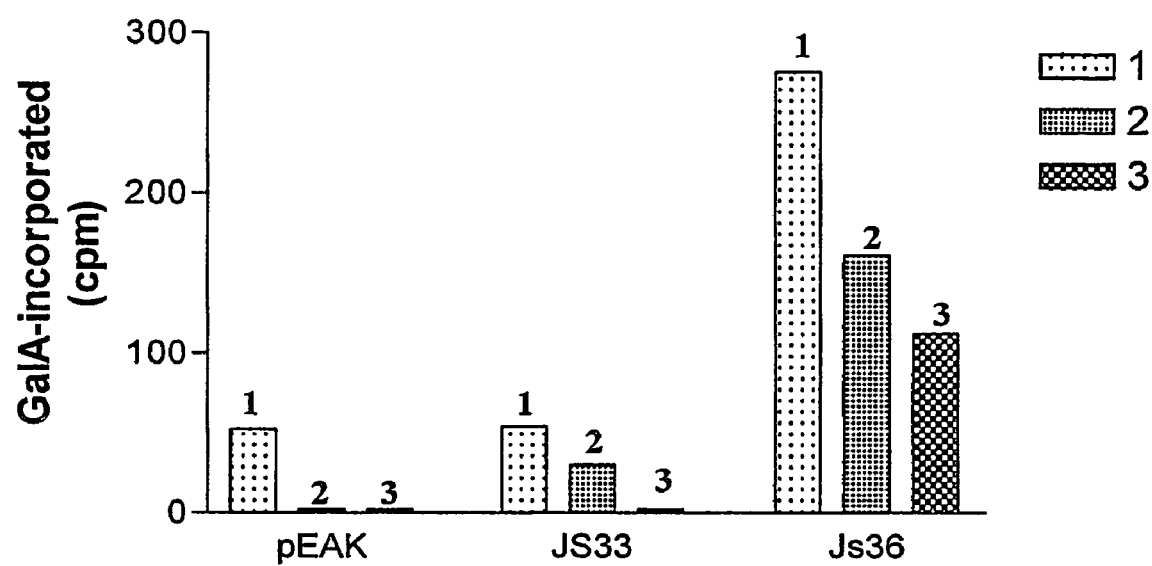
FIG. 8 demonstrates that recombinant JS36 (At3g61130) has galacturonosyltransferase (GalAT) activity. Human embryonic kidney cells (HEK293) were transiently transfected with the pEAK vector alone, or with pEAK vector containing the truncated versions of JS33 or JS36. Total media (1); protein immunoabsorbed from the medium using anti-HA epitope: Protein A SEPHAROSE (2); and protein immunoabsorbed from the medium using anti-HA epitope: Protein G SEPHAROSE (3) were tested for GalAT activity. Data are the average [$^{14}$C]GalA incorporated into product from duplicate reactions from three separate experiments.

The truncated forms of JS33, JS36 and JS36L, and the vector alone, were transiently expressed in human embryonic kidney cells (HEK293 cells) for 46 hours. Since the translational fusion proteins constructed contained two copies of the HA epitope, the culture medium was collected and a portion was treated with a mouse anti-HA IgG1 bound either to Protein A SEPHAROSE or Protein G SEPHAROSE. The immunoadsorbed protein was assayed for GalAT activity using UDP-[$^{14}$C]GalA and a mixture of OGA acceptors. FIG. 8 shows that the JS36 construct expressed a protein exhibiting GalAT activity. These studies establish that JS36 is a GalAT and thus we designated the gene GALAT1.

As mentioned above, analysis of the amino acid sequence of GALAT1 shows that the expressed protein contains one transmembrane domain. This is in agreement with the GalAT activity being membrane bound in all species tested (see Mohnen et al. (2002)[9]. Furthermore, the predicted topology of GALAT1 is that of a type-II membrane protein, in agreement with our previous determination that the catalytic site of pea GalAT lies in the lumen of the Golgi. Type-II membrane proteins have a short N-terminal cytosolic tail, a transmembrane region, a stem region, and a C-terminal catalytic domain[16].

GALAT1 is a member of the Glycosyltransferase Family 8 in the CAZy database [database of putative and proven carbohydrate modifying enzymes that currently contains 61 different proposed glycosyltransferase families website is afmb.cnrc-mrc.fr/CAZy/index/html) 66,67]. The presence of GALAT1 in Family 8 is in agreement with our demonstrated activity of GALAT1 as an α1,4-galacturonosyltransferase, since Family 8 is a family of proposed retaining glycosyltransferases and GALAT1 is a retaining enzyme, i.e., the α-configuration in the substrate UDP-α-GalA is retained in the product α1,4-linked-galacturononan (HGA).

Figure 6A:
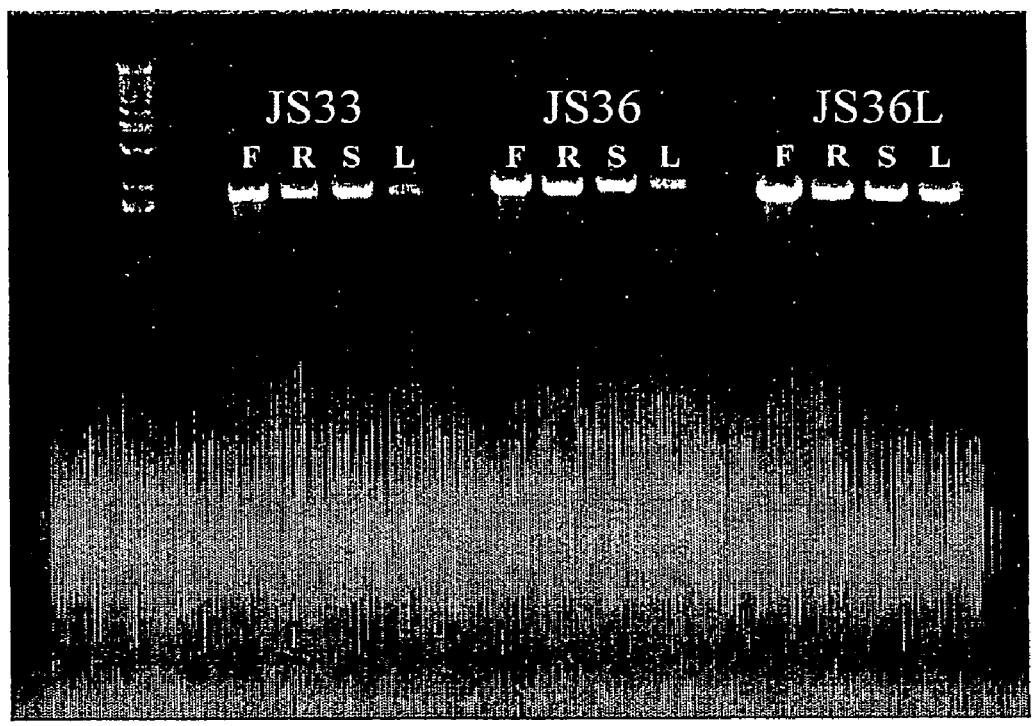
FIGS. 6A and 6B show the results of RT-PCR experiments; 6A shows the results of JS33, JS36, and JS36L (a GalAT family gene with 63% identity to JS36) using *Arabidopsis* flower (F), root (R), stem (S), and leaf (L) RNA, and B shows the RT-PCR control using *Arabidopsis* actin gene in the same tissues.
Figure 6B:
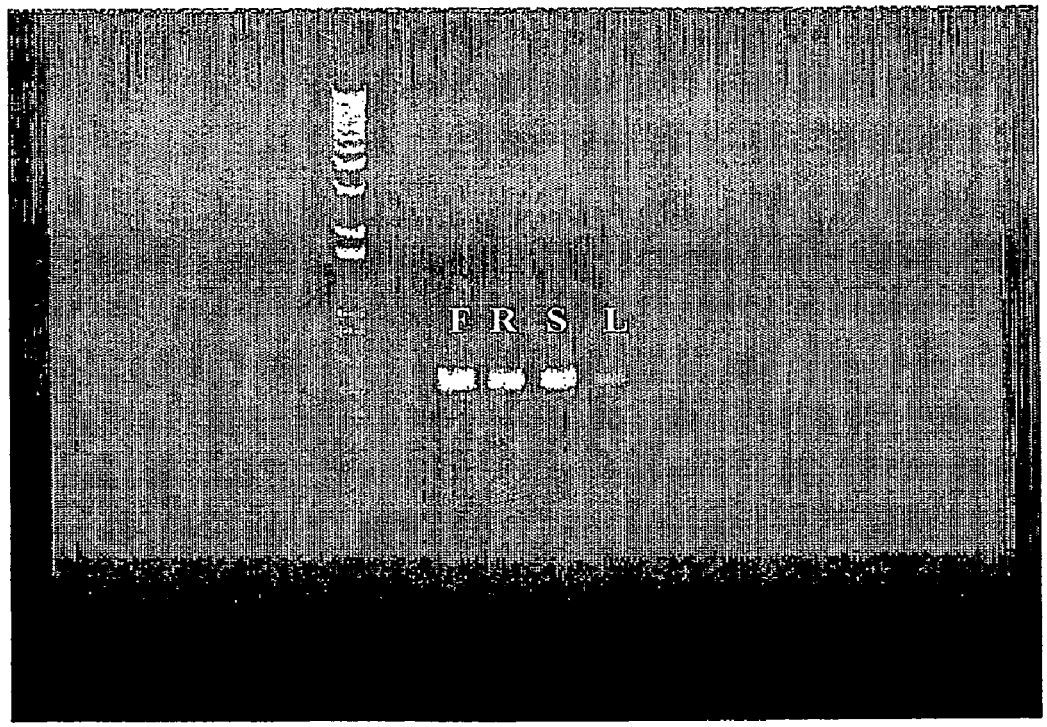

GALAT is expressed in multiple *Arabidopsis* tissues at multiple times during development. We base this on our RT-PCR analysis of RNA from *Arabidopsis* flower, root, stem and leaf tissue (FIGS. 6A and 6B) showing that GALAT1 is expressed in all these tissues, and based on the 18 EST entries for this gene in the TAIR database (website entitled arabidopsis.org) indicating that GALAT1 is expressed in developing seed, green siliques, roots and above ground organs.

Identification of the GALAT1 Gene Family

A standard protein blast and a PSI Blast of the NCBI protein database using the GALAT1 (JS36) amino acid sequence reveal that GALAT1 is a member of a at least 15 member GALAT gene family in *Arabidopsis* (see Table IV). The genes selected for this family have at least 30% amino acid identity and at least 50% amino acid similarity based on the PSI Blast. We further compared these genes along their entire coding sequences with JS36 using a Pairwise BLAST (Table IV) and show that this family of genes has at least 34% identity and at least 52% similarity to JS36 in the portion of the genes C-terminal to the membrane spanning domain. This identity is comparable to the 37-54% identity shared among the proposed ten member *Arabidopsis* fucosyltransferase gene family (AtFU1-10)[71].

Mutant studies provide further evidence that the GalAT family encodes GalATs involved in pectin synthesis. We recently used seed received from *Arabidopsis* T-DNA mutant collection (SIGnAL; website entitled signal.salk./edu/cgi-bin/tdnaexpress) to identify and generate six homozygous *Arabidopsis* GalAT family T-DNA insert mutant lines of several members of the GalAT family. We found that one GalAT family gene At1g06780, when mutated, produces leaves with cell walls that contain reduced amounts of galacturonic acid. Specifically, analysis of walls from homozygous mutant line 073484 revealed that the walls had an 18% reduction in GalA and a concomitant increase in glucose. None of the other sugars changed. Of the three available At1g06780 T-DNA insert lines, no homozygous seed was recovered from mutants where the T-DNA was inserted into an exon. Rather, seed recovered from such lines had a reduced germination rate. In line 073484, however, the T-DNA is inserted in the 5'-UTR, suggesting that it may have a leaky phenotype. The results are consistent with gene At1g06780 encoding a GalAT and with the identification of the gene family as a GalAT gene family. The GalA content of the walls of another *Arabidopsis* mutant (Quasimodo) is reduced by 25% and these plants exhibit decreased cell adhesion[55], characteristics consistent with the Quasimodo gene encoding a GalAT. Quasimodo has 53% amino acid identity and 72% similarity to GALAT1 and the gene affected in Quasimodo (At3g25140) is a member of our proposed GalAT family. There is, however, at present no direct enzymatic evidence that the protein encoded by Quasimodo is a functional GalAT.

Figure 7:
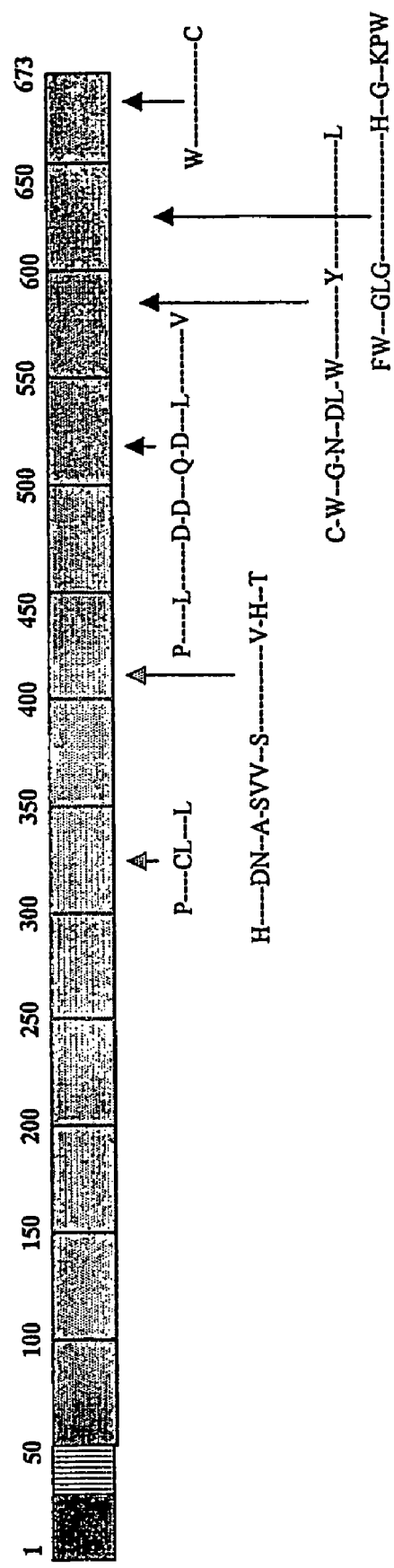
FIG. 7 is a schematic representation of the transmembrane spanning region and the conserved amino acids in the *Arabidopsis thaliana* GALAT gene family. The relative position of the strictly conserved residues among the members of the proposed GALAT family is numbered as for JS36 (i.e., GALAT1). The striped region from residues 22-44 represents the predicted transmembrane region. P----CL---L, SEQ ID NO:51; P-----L------D-D---Q-D---L--------V, SEQ ID NO:52; W-------------C, SEQ ID NO:53; H-----DN-A-SVV-S-----------V-H-T, SEQ ID NO:54; C-W-G-N-DL-W--------- Y----------------L, SEQ ID NO:55; FW---GLG---------------- H-G-KPW, SEQ ID NO:56.

The conserved amino acids in the GALAT gene family are shown in FIG. 7. Glycosyltransferases are expected to contain one or more carboxylates at the catalytic site. At least one of the carboxylates is expected to coordinate a divalent cation associated with the nucleotide-sugar. In many glycosyltransferases the metal coordination involves two carboxylates that are often present as DDx, xDD, or DDD (the so-called "D(x) D" motif)[72].

Figure 9:
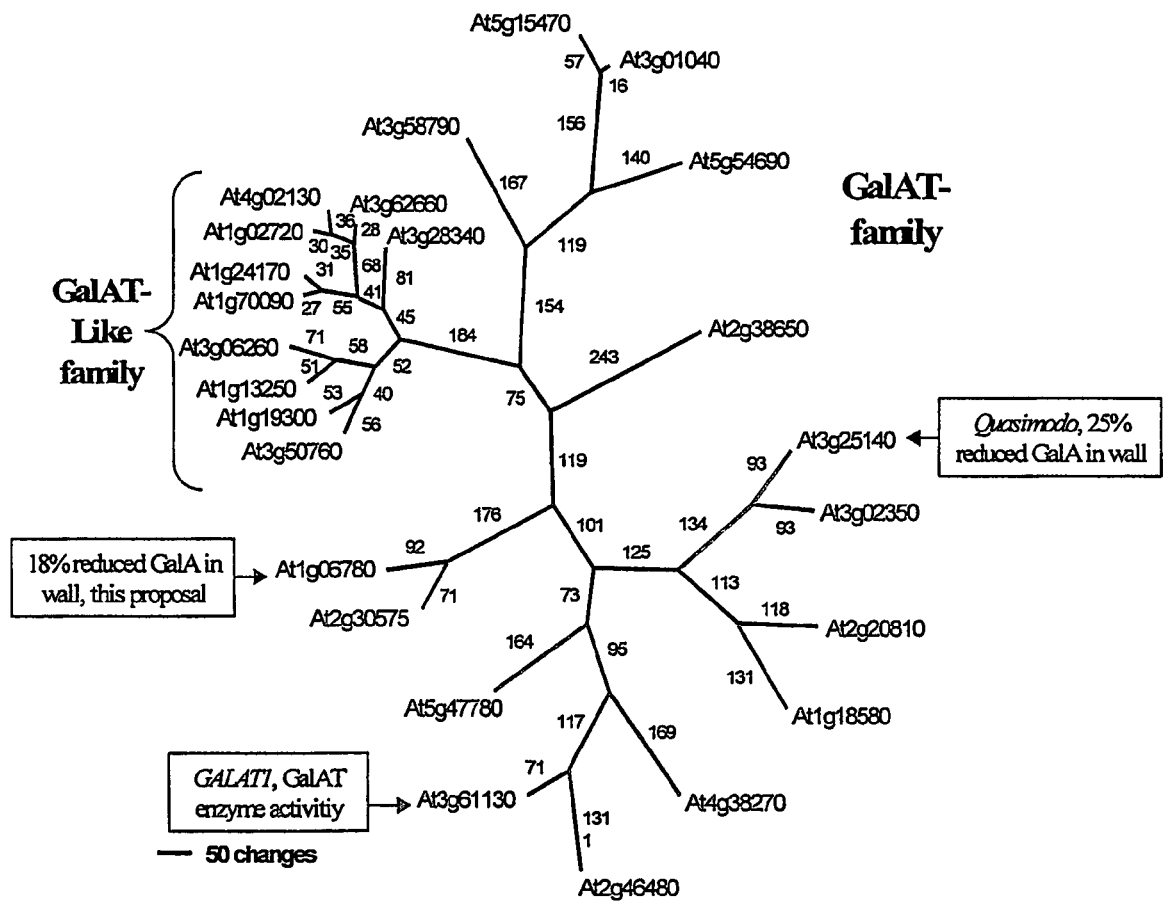
FIG. 9 shows the relationship of the *Arabidopsis* GalAT superfamily including the GalAT family and the GalAT-like family. The Neighbor-Joining Tree is based on a sequence alignment generated by ClustalX.

A PSI Blast against GALAT1 gene (JS36) further identified 10 genes that have high sequence identity (23-29%) and similarity (41-51%) to GALAT1 and form a tight cluster of highly similar genes (55-66% identity/67-77% similarity). A Neighbor Joining Tree of our proposed *Arabidopsis* GalAT Superfamily (i.e. the proposed GALAT family and the GALAT-Like family), based on a sequence alignment generated by ClustalX[128], is shown in FIG. 9. The 10 GALAT-like genes are all significantly smaller, lacking ~200 amino acids in comparison with the GALAT family. Nonetheless, they appear to be targeted to the secretory pathway based on annotation of the genes at the *Arabidopsis* Information Resources. All 10 genes appear to be expressed in *Arabidopsis*, since they are represented by one or more ESTs in the *Arabidopsis* EST collection. The GALAT-like genes also contain some of the same conserved residues as the GalAT family, namely D-D-----D---L (SEQ ID NO:57; the predicted "D(x) D" motif) and L------F----------W---GLG--------------------H-G-KPW (SEQ ID NO:58). We group the 10 GALAT-like genes into a family that encode GalATs directly involved in pectin synthesis or GalATs with, as yet, unidentified glycosylating function.

TABLE IV

Pairwise sequence alignment between JS36 and the other members of proposed GALAT gene family. The alignment was done using the NCBI Pairwise BLAST and Matrix Blosum62. The % amino acid identity and similarity are shown. In all cases the alignment compares the bulk of the C-terminal portion of the proteins on the carboxy-terminal side of the transmembrane region.

| Gene | NCBI protein ID | EMBL protein # | % Identity (#aa identical/#aa) | % Similar amino acids (aa/aa) |
|---|---|---|---|---|
| GalAT-Family | | | | |
| ***At3g61130 (GALAT1; JS36) | NP_191672 | Q9LE59 | 100% (673/673) | 100% (673/673) |
| At5g47780 (JS36-like) | NP_568688 | Q93ZX7 | 63% (290/458) | 81% (374/458) |
| At2g46480 | NP_182171 | | 61% (297/485) | 75% (365/485) |
| At4g38270 | NP_195540 | | 55% (344/620) | 73% (459/620) |
| At3g25140 (Quasimodo) | NP_189150 | Q9LSG3 | 53% (241/450) | 72% (330/450) |
| At1g18580 | AAK93644 | | 48% (226/469) | 67% (317/469) |
| At3g02350 | NP_566170 | Q9FWA4 | 47% (247/521) | 66% (350/521) |
| At2g20810 | NP_565485 | Q93VL7 | 46% (215/462) | 68% (320/462) |
| At1g06780 | NP_563771 | Q9M9Y5 | 44% (204/461) | 63% (296/461) |
| At2g30575 | NP_850150 | | 43% (203/463) | 65% (309/463) |
| At3g01040 | NP_186753 | Q9MAB8 | 42% (189/447) | 61% (227/447) |
| At5g15470 | NP_197051 | Q9LF35 | 42% (189/443) | 61% (274/443) |
| At5g54690 | NP_200280 | Q9FH36 | 38% (169/436) | 60% (265/436) |
| At2g38650 (JS33) | NP_565893 | Q949N9 | 36% (171/475) | 60% (286/475) |
| At3g58790 | NP_191438 | Q9LXS3 | 34% (160/458) | 52% (247/458) |
| GalAT-Like Family | | | | |
| At1g02720 | NP_171772 | | 26 (85/316) | 44 (143/316) |
| At1g13250 | NP_563925 | Q9FX71 | 23 (86/359) | 41 (154/359) |
| At1g19300 | NP_564077 | Q9LN68 | 29 (58/198) | 49 (98/198) |
| At1g24170 | NP_173827 | O48684 | 23 (75/322) | 41 (136/322) |
| At1g70090 | NP_564983 | O04536 | 27 (64/233) | 48 (115/233) |
| At3g06260 | NP_187277 | Q9M8J2 | 29 (52/179) | 51 (92/179) |
| At3g28340 | NP_189474 | Q9LHD2 | 28 (56/194) | 52 (104/194) |
| At3g50760 | NP_190645 | Q9S7G2 | 24 (76/308) | 43 (137/308) |
| At3g62660 | NP_191825 | Q9LZJ9 | 29 (56/191) | 51 (99/191) |
| At4g02130 | NP_192122 | | 29 (58/197) | 51 (103/197) |

The expression of the GALAT1 gene in transiently transfected mammalian cells as demonstrated herein now allows the production of stably transformed cell lines that produce GALAT1 and experiments aimed at characterizing the mechanism of the enzyme and at determining the role of GalAT1 in pectin synthesis. Specifically, the substrate specificity of GalAT1 will indicate whether it catalyzes only HGA synthesis, or also plays a role in RG-I and RG-II synthesis. Characterization of the kinetics of GalAT1 can clarify whether or not UDP-GalA is both a substrate and an allosteric regulator of the enzyme. Characterization of the mutated GalA1 enzyme can provide information regarding amino acids important in catalysis and substrate binding. The subcellular location of GALAT1 will provide the first framework for where, within the Golgi and plant endomembrane system the complex series of pectin biosynthetic reactions occur. The invention can further be used to generate transgenic plants with modified pectin, which can provide information regarding the role of GALAT1 in pectin synthesis, provide novel biosynthesis acceptors, and provide information about the role of pectin in plant growth and development. This biosynthesis framework allows further identification of GALAT1 binding proteins that would be putative pectin biosynthesis complex members. The results of these studies can serve as the foundation for a full in vitro reconstitution of functional pectin synthesis complexes.

GALAT1 has high sequence similarity to 14 other *Arabidopsis* proteins as shown in Table IV and to proteins expressed in other plants. Possible GALAT1 homologs in other plants are a 68 kd protein expressed in *Cicer arietinum* (chickpea) epicotyls (76% amino acid identity; 87% similarity), a hypothetical protein from *Oryza sativa* (japonica) (59% identify; 75% similarity) and a protein from *Populus alba* (49% identity; 72% similarity). Thus, the results from the study of GALAT1 in *Arabidopsis* can be extended to other plants, including those of high agricultural value.

Heterologous Expression of GALAT1

As described above, the media from human embryonic kidney (HEK293) cells transiently infected with recombinant expression vector bearing truncated GALAT1 expressed GALAT1. Whereas transient expression allowed the expression of sufficient GALAT to measure GalAT activity, additional expression strategies can be readily devised to produce large quantities of GALAT1 required for further characterization of the enzyme and for antibody production. Since the transiently expressed N-terminal epitope-tagged GALAT1 expressed in mammalian cells was active, one strategy is to produce stably transfected clonal HEK293 lines[75] expressing the same protein. The alternative strategy is to express the full length and N-terminal truncated forms of GALAT1 in the fungal expression system *Pichia pastoris*. These systems were chosen since we and others[56-58] have successfully used them to express plant glycosyltransferases.

For expression in *P. pastoris*, cDNA encoding the entire, and the truncated soluble forms of GALAT can be generated by PCR using gene/vector specific primers. The PCR products are then subcloned into appropriate *Pichia* expression vectors (Invitrogen, Carlsbad, Calif.) in which the cDNA is inserted downstream from an alcohol oxidase (AOX1) promoter. We have made full length coding sequence constructs for expression in the *Pichia* vector pPIC 3.5. This vector does not contain an epitope tag. One can easily make epitope tagged GALAT1 constructs in the *Pichia* vectors pPICz and pPICzα (Invitrogen) and determine whether functional C-terminal epitope-tagged constructs that do not affect GalAT activity can be recovered. Several studies have demonstrated success of the *Pichia* system[76-82]. Once a high-GALAT1-producing line is recovered, production of large amounts of protein can be carried out in fermentors or spinner flasks.

Characterization of Expressed GALAT1

To begin to address how HGA is synthesized, the kinetics, substrate specificity, and structure of the purified recombinantly expressed GALAT1 can be determined and compared to the solubilized membrane-bound *Arabidopsis* GALAT purified by immunoadsorption using the polyclonal-anti-GALAT1 (see below). Although the characteristics of GalAT1 are consistent with the enzyme being the/a catalytic subunit of the HGA synthase, GALAT1 could be a GalAT involved in RG-II or RG-I synthesis. For example, GalAT could represent an RG-I: GalAT that initially elongates HGA by a single GalA and then waits for a required NDP-Rha to start RG-I backbone synthesis. The kinetics of purified and recombinantly expressed GALAT1 for UDP-GalA and a size range of homogalacturonan and pectin acceptors can be determined. The effect of other nucleotide-sugars and oligosaccharide substrates on GalAT can also be tested to identify activators and inhibitors.

The expressed full length and truncated enzymes can be assayed in a reaction buffer in the presence, and absence, respectively, of Triton X-100. The kinetics of the enzyme for UDP-GalA can be carried out in a total of 1 µM to 80 mM UDP-GalA+UDP-[$^{14}$C]GalA. We routinely synthesize UDP-[$^{14}$C]GalA either by the 4-epimerization of UDP-[$^{14}$C]GlcA[1] or oxidation of UDP-[$^{14}$C]Gal[84] since UDP-[$^{14}$C]GalA is not commercially available. The effect of different acceptors on GALAT1 activity can be conducted using 100 µM UDP-GalA and 0.1-100 µg acceptor/30 µl reaction. The acceptors to be tested include HGA oligosaccharides (oligogalacturonides) of degrees of polymerization ranging from 2-16, polygalacturonic acid, commercially available citrus pectin of ~30, 60 and 90% esterification, RG-I and RG-II. The products made using the different acceptors can be characterized[2,3]. If RG-I is shown to serve as an acceptor, RG-I backbone fragments that have a GalA or a Rha at the non-reducing end can be used to determine acceptor specificity. The acceptors can be tested using multiple assays including the precipitation assay[2] and a filter assay[63]. The enzymes can also be tested for the effect of pH, temperature, reducing agents, divalent cations and salts on enzyme activity and product structure.

Characteristics of the recombinant truncated GALAT1 can be compared to the GALAT1 solubilized from *Arabidopsis* membranes by immunoadsorption of the solubilized GALAT1 using anti-GALAT1 antibody (see section below) bound to Protein A or G SEPHAROSE, or by coupling the anti-GALAT1 antibodies to 3M-Emphaze resin and using the resin used to purify GALAT1 from solubilized *Arabidopsis* enzyme. If the characteristics of the immunoadsorbed *Arabidopsis* GALAT1 are different from those of the recombinant truncated GALAT1, the immunoadsorbed GALAT1 can be analyzed by LC tandem mass spectrometry to determine if additional proteins are immunoadsorbed with the *Arabidopsis* solubilized GALAT1 that may have modified the activity (e.g. a heteromeric complex).

The recombinant GALAT1 and the GALAT1 immunoadsorbed-from *Arabidopsis* solubilized membranes can also be treated with N-glycanase to determine if they are N-glycosylated. To determine if they are O-glycosylated, the proteins can be exhaustively treated with N-glycanase, the released oligosaccharides removed, and the resulting protein analyzed by TMS methylation analysis to determine the glycosyl residue composition of any carbohydrates still attached to the protein. Any oligosaccharide released by the N-glycanase treatment can also be analyzed by TMS methylation. The results of these experiments would indicate whether the native *Arabidopsis* GalAT is glycosylated and whether the recombinant forms have the same or different glycosylation pattern. Changes in glycosylation could affect GalAT1 enzyme activity and/or substrate binding. GALAT1 is predicted to have 5 or 6 N-glycosylation sites (NetNGlyc 1.0 Prediction; website entitled expasy.org/sitemap.html).

As mentioned above, we have found that membrane-bound and solubilized GalAT activity in tobacco and radish has unusual apparent biphasic kinetics. Thus, we are particularly interested in determining if the expressed GALAT1 shows the same kinetics, including possible allosteric regulation by UDP-GalA. One can test for possible multimeric structure by determining the mass of the enzyme by size exclusion chromatography and comparing these with the mass obtained by SDS-PAGE. The possibility that GALAT1 exists as a heteromultimer can be tested by mixing expressed recombinant GALAT1 with solubilized *Arabidopsis* enzymes and immunoadsorbing GALAT1 and proteins bound to it using either an anti-GALAT1 antibody or an anti-HA epitope antibody (see previous section).

Production of a Series of Mutated GALAT1 Proteins by Site-Directed Mutagenesis

As discussed above, there are 45 conserved amino acids in GALAT1 among the 15 members of the GALAT family. To determine the role of these residues in substrate/acceptor binding and/or catalysis, each amino acid is systematically mutated using site-directed mutagenesis. The effect of these mutations on GALAT1 specific activity, and where warranted, on Km, Vmax, and acceptor specificity (i.e. OGA, RG-I and RG-II) and product size (i.e. enzyme processivity) is determined.

Production and Use of Antibodies

Anti-GalAT antibodies are necessary for the immunocytochemistry experiments, to immunopurify solubilized GALAT1 from *Arabidopsis*, and to select proteins that potentially bind to GALAT1 and may function in pectin biosynthetic enzyme complexes. A skilled artisan can generate anti-GalAT antibodies using the nucleic acid or amino acid sequences disclosed herein. This can be accomplished by employing the heterologously expressed truncated or full-length GALAT1. Alternatively, a small peptide derived from the GALAT1 sequence can be synthesized and used to generate anti-GALAT1 antibodies. One can generate either polyclonal or monoclonal antibodies. Such antibodies are useful for a range of types of experiments, including subcellular immunocytochemistry, immunoprecipitation/adsorption, and enzyme activity inhibition studies. Monoclonal or polyclonal antibodies, specifically reacting with a protein of interest can be made by methods well known in the art. See, e.g., Harlow and Lane (1988) *Antibodies: A Laboratory Manual*, Cold Spring Harbor Laboratories; Goding (1996) *Monoclonal Antibodies: Principles and Practice*, 3rd ed., Academic Press, San Diego, Calif., and Ausubel et al. (1993) *Current Protocols in Molecular Biology*, Wiley Interscience/Greene Publishing, New York, N.Y.

Subcellular Localization of GALAT1

All available data, including the localization of the catalytic domain of GalAT in the Golgi lumen[7], suggest that pectin is synthesized in the Golgi and transferred via vesicles to the wall. However, it is not known how the different glycosyltransferases function to make specific pectin structures. We predict that different glycosyltransferases are localized in a sequential manner to different cisternae of the Golgi[22,91] in an order indicative of the order in which pectin is synthesized as it moves from the cis, through the medial and to the trans Golgi. Evidence from both animal[92,93] and plants[94] suggests that, either individually or in combination, the transmembrane domain (i.e. the bilayer thickness model[95]), the N- or C-terminal sequences flanking the transmembrane domain, and/or the lumenal domain (i.e. the 'kin recognition model'[96]) contribute to localization of proteins within the Golgi system. The anti-GalAT antibodies generated as described above can be used to determine the subcellular localization of GALAT1 within the Golgi in order to provide additional information on the role of GalAT1 in pectin synthesis. For example, a location of GALAT1 in the cis and medial Golgi cisternae would be consistent with a function of GALAT1 in HGA synthesis, while a localization primarily in the late medial or trans Golgi would be more suggestive of a role in RG-I or possible RG-II synthesis. It should be noted that such subcompartment localization studies, while important and novel for the pectin biosynthetic enzymes, are also novel in any species since the "precise location of only a small number of the glycosyltransferase proteins within the Golgi apparatus have been determined"[93]. Anti-GALAT1 antibodies can be used to identify where in the Golgi GALAT1 is localized by, for example, immunogold label of thin sections from *Arabidopsis*[97,91,98,99] including both developing *Arabidopsis* seedlings and growing suspension cultures which have cells actively making wall.

Use of Mutants and RNAi to Generate and Characterize GALAT1 and GalAT Gene Superfamily Knockouts.

Double-stranded RNA-mediated interference (RNAi) is a method to study the function of genes in plants 100. Transgenic plants harboring an RNAi construct often have reduced expression of the gene-specific mRNA. The resulting plants may display either complete gene silencing, thus having a knockout phenotype, or a partial "knockout" phenotype due to 'leaky' expression. The RNAi approach should allow the suppression of GALAT1 expression and a reduction or loss of GALAT1. This enables one to elucidate the function of GALAT in pectin synthesis and in the plant. Simultaneously, the sequence-indexed T-DNA insertion mutants listed in the Salk Institute Genomic Analysis Laboratory (SIGnAL) *Arabidopsis* T-DNA mutant collection (website entitled signal.salk./edu/cgi-bin/tdnaexpress) can be monitored to determine if any T-DNA insert lines for GALAT become available. If so, the seed can be obtained and the mutants generated therefrom can be characterized (as described above).

The putative pectin biosynthesis mutants can aid in the identification of gene function in two ways. The visible phenotypes of the mutants can provide information on the biological function of the gene (if there is no redundancy in gene function) by demonstrating when during growth and development the particular gene product is needed (as shown above). Structural analysis of the pectin in the mutant walls can provide information about the specific enzyme activity of the gene in pectin synthesis (as shown above).

Of particular importance regarding pectin synthesis, the cell walls are isolated and analyzed for glycosyl residue composition (see above) and linkage to provide information about the possible role of GALAT1 in pectin synthesis.

Identification of the Members of HGA Biosynthetic Complexes.

There is growing evidence that glycoconjugates are synthesized by complexes of glycosyltransferases and other types of proteins[102]. For example, ganglioside synthesis occurs via a tightly regulated formation of multiple glycosyltransferase complexes[102]. Thus, any protein members of HGA biosynthetic complexes can be isolated by immunoadsorbing such proteins bound to GALAT1 using anti-GALAT1 antibodies or anti-HA epitope antibodies. The immunoadsorbed proteins can be identified by SDS-PAGE, removed from the gel, and their amino acid sequence determined by LC-tandem mass spectrometry. The amino acid sequences thus obtained can then be used to search the available protein databases for their identities.

Characterization of Mutant Phenotypes and Bulking Up of Seed.

A person of ordinary skill in the art can use mutant seeds to probe gene function. For example, the initial mutant seed (often a segregating T3 line, see (website entitled signal.salk./edu/tdna$_{13}$FACs.html) can be grown and selfed to increase the seed stock (T4). Multiple plants from T4 seed can be grown and the presence of, for example) the T-DNA insert determined by PCR of plant genomic DNA using a T-DNA primer and a gene specific primer. The same DNA can be analyzed with gene specific primers that should span the T-DNA insertion site. These analyses should indicate whether the given plant contains a T-DNA insert and if so, whether it is homozygous or heterozygous for the mutation. If necessary, Southern blotting and hybridization with the specific genes can be used to determine if the gene contains the expected T-DNA insert. Seed homozygous for the T-DNA insertion (when not lethal) or heterozygous (when no viable TDNA homozygous plants are obtained) can be selfed to amplify the seed and, for heterozygous plants, to test for segregation of any phenotype or T-DNA insert. Plants can be scored as heterozygous or homozygous by PCR analysis of the T-DNA insert and by any visible phenotype. Homozygous or heterozygous plants can be used for growth phenotype and cell wall analysis. The seed can also be crossed with wild type Columbia and then selfed to eliminate the possibility that the lines contain an unexpected mutation or additional T-DNA insert(s).

Growth Phenotype Analysis

Several growth parameters of the mutant and wild type plants are recorded to yield a general phenotypic characterization of the mutant plants.[134]

Analysis of Cell Walls

Homozygous or heterozygous plants are grown and analyzed for wall composition and linkage. Cell walls can, for example. be prepared as alcohol insoluble residues (AIRs) from WT and (homozygous) mutant *Arabidopsis* plant tissues[135]. AIRs are prepared by homogenizing leaves and stems (from soil-grown plants) and roots (from liquid-cultured plants) in aquous 80% EtOH followed by washes with absolute EtOH, chloroform-methanol, and acetone. Separate fractions containing RG-I, RG-II and oligogalacturonides can be obtained by size-exclusion chromatography (SEC) and ion exchange chromatography of the material solubilized from the cell walls by treatment with pectin methyl esterase (PME) and endo-polygalacturonase (EPG). The yields, glycosyl residue compositions, and glycosyl linkage compositions of each fraction can be determined[27].

The nucleotide and amino acid sequences of the fifteen GALAT gene family members are shown as follows.

```
Sequence #1 (SEQ ID NO:1)
Gene name: At3g61130
GeneBank accession # for reference: NM_115977 GI:18411855
Nucleotide sequence of Sequence #1:
Positions 1-2022 of CDS of NM_115977.
   1 atggcgctaa agcgagggct atctggagtt aaccggatta gaggaagtgg tggtggatct 61 cgatctgtgc ttgtgcttct catattttc  tgtgttttg  cacctctttg cttctttgtt 121 ggccgaggag tgtatatcga ttcctcaaat gattattcaa ttgtttctgt gaagcagaat 181 cttgactgga gagaacgttt agcaatgcaa tctgttagat ctcttttctc gaaagagata 241 ctagatgtta tagcaaccag cacagctgat ttgggtcctc ttagccttga ttcttttaag 301 aaaaacaatt tgtctgcatc atggcgggga accggagtag accctcctt  tagacattct 361 gagaatccag caactcctga tgtcaaatct aataacctga atgaaaaacg tgacagcatt 421 tcaaaagata gtatccatca gaaagttgag acacctacaa agattcacag aaggcaacta 481 agagagaaaa ggcgtgagat gcgggcaaat gagttagttc agcacaatga tgacacgatt 541 ttgaaactcg aaaatgctgc cattgaacgc tctaagtctg ttgattctgc agtccttggt 601 aaatacagta tttggagaag agaaaatgag aatgacaact ctgattcaaa tatacgcttg 661 atgcgggatc aagtaataat ggctagagtc tatagtggga ttgcaaaatt gaaaaacaag 721 aacgatttgt tacaagaact ccaggcccga cttaaggaca gccaacgggt tttggggaa 781 gcaacatctg atgctgatct tcctcggagt gcgcatgaga aactcagagc catgggtcaa 841 gtcttggcta aagctaagat gcagttatat gactgcaagc tggttactgg aaagctgaga 901 gcaatgcttc agactgccga cgaacaagtg aggagcttaa agaagcagag tactttctg 961 gctcagttag cagcaaaaac cattccaaat cctatccatt gcctatcaat gcgcttgact 1021 atcgattact atcttctgtc tccggagaaa agaaaattcc ctcggagtga aaacctagaa 1081 aaccctaatc tttatcatta tgccctcttt tccgacaatg tattagctgc atcagtagtt 1141 gttaactcaa ccatcatgaa tgccaaggat ccttctaagc atgtttttca ccttgtcacg 1201 gataaactca atttcggagc aatgaacatg tggttcctcc taaacccacc cggaaaggca 1261 accatacatg tggaaaacgt cgatgagttt aagtggctca attcatctta ctgtcctgtc 1321 cttcgtcagc ttgaatctgc agcaatgaga gagtactatt ttaaagcaga ccatccaact 1381 tcaggctctt cgaatctaaa atacagaaac ccaaagtatc tatccatgtt gaatcacttg 1441 agattctacc tccctgaggt ttatcccaag ctgaacaaaa tcctcttcct ggacgatgac 1501 atcattgttc agaaagactt gactccactc tgggaagtta acctgaacgg caaagtcaac 1561 ggtgcagtcg aaacctgtgg ggaaagtttc cacagattcg acaagtatct caacttttcg 1621 aatcctcaca ttgcgaggaa cttcaatcca aatgcttgtg gatgggctta tggaatgaac 1681 atgttcgacc taaaggaatg gaagaagaga gacatcactg gtatatacca caagtggcaa
```

-continued

```
1741 aacatgaatg agaacaggac actatggaag ctagggacat tgccaccagg attaataaca 1801 ttctacggat taacacatcc cttaaacaag gcgtggcatg tgctgggact tggatataac 1861 ccgagtatcg acaagaagga cattgagaat gcagcagtgg ttcactataa cgggaacatg 1921 aaaccatggt tggagttggc aatgtccaaa tatcggccgt attggaccaa gtacatcaag 1981 tttgatcacc catatcttcg tcgttgcaac cttcatgaat aa
```

Amino Acid Sequence of Sequence #1: (SEQ ID NO:2)
GeneBank ID# NP_191672
Positions 1-673 of NP_191672.

```
  1 malkrglsgv nrirgsgggs rsvlvlliff cvfaplcffv grgvyidssn dysivsvkqn 61 ldwrerlamq svrslfskei tdviatstad lgplsldsfk knnlsaswrg tgvdpsfrhs 121 enpatpdvks nnlnekrdsi skdsihqkve tptkihrrql rekrremran elvqhnddti 181 lklenaaier sksvdsavlg kysiwrrene ndnsdsnirl mrdqvimarv ysgiaklknk 241 ndllqelqar lkdsqrvlge atsdadlprs aheklramgq vlakakmqly dcklvtgklr 301 amlqtadeqv rslkkqstfl aqlaaktipn pihclsmrlt idyyllspek rkfprsenle 361 npntyhyalf sdnvlaasvv vnstimnakd pskhvfhlvt dklnfgamnm wfllnppgka 421 tihvenvdef kwlnssycpv lrqlesaamr eyyfkadhpt sgssnlkyrn pkylsmlnhl 481 rfylpevypk lnkilflddd iivqkdltpt wevnlngkvn gavetcgesf hrfdkylnfs 541 nphiarnfnp nacgwaygmn mfdlkewkkr ditgiyhkwq nmnenrtlwk lgtlppglit 601 fyglthplnk awhvlglgyn psidkkdien aavvhyngnm kpwlelamsk yrpywtkyik 661 fdhpylrrcn lhe
```

Sequence #2 (SEQ ID NO:3)
Gene name: At2g38650
GeneBank accession # for reference: NM_129422 GI:30687590
Nucleotide sequence of Sequence #2:
Positions 1-1860 of CDS of NM_129422

```
   1 atgaaaggcg gaggcggtgg tggaggaggt ggtggcggag gaaaacgccg gtggaaagtt 61 ctggtgattg gagttttggt tcttgttatt ctttctatgc ttgttcctct tgctttctta 121 ctcggtcttc acaatggctt tcactctcct ggatttgtca ctgttcaacc ggcttcttca 181 tttgagagct ttaccagaat caatgctact aagcatacac agagagatgt atccgaacgg 241 gtcgatgagg ttcttcaaaa aatcaatcca gttcttccca agaaaagcga cataaacgtg 301 ggttccagag atgtgaatgc aacaagcggc actgattcta aaaaagagg attaccagtg 361 tccccaactg ttgttgccaa tccaagccct gcaaataaaa caaaatcgga agcctcatat 421 acaggtgttc agaggaaaat agtaagtggt gatgaaactt ggagaacttg tgaagtgaaa 481 tatgggagct actgcctctg gagggaggaa ataaggaac caatgaaaga tgccaaggtg 541 aagcaaatga aggaccagct gtttgtggct agagcatact atcccagtat tgctaaaatg 601 ccttctcaaa gcaagttgac tcgggatatg aaacagaata tccaagagtt tgagcgtatt 661 cttagtgaaa gttctcaaga tgctgacctt ccaccacagg ttgataaaaa gttgcagaag 721 atggaagctg taattgcaaa ggcaaagtct tttccagtcg actgtaacaa tgttgacaag 781 aaattgagac agatccttga tttgactgag gatgaagcta gtttccacat gaaacagagt 841 gtgttcctct accagcttgc agtacagaca atgcctaaga gtcttcattg cttgtcaatg 901 cgactaactg tggaacattt caagtcagat tcacttgagg atcccattag tgagaaattt 961 tcagatccct cattacttca ctttgttatc atctccgata atatactagc atcgtccgtt 1021 gtgatcaact caacggttgt acatgcaagg gacagtaaaa actttgtttt ccatgtactg 1081 acagacgagc agaattactt tgcaatgaaa caatggttta ttaggaatcc ttgcaaacaa
```

-continued

```
1141 tcaactgttc aagtattgaa cattgaaaaa ctcgagctgg acgattctga tatgaaactg 1201 tctttgtctg cggagttccg tgtttccttc cccagtggtg accttttggc gtctcaacag 1261 aatagaacac actacttatc cctttctctc caatctcact atcttcttcc caaattattt 1321 gacaaattgg agaaggttgt gattctggat gatgacgttg tagtccagcg agacttatct 1381 cccctttggg accttgatat ggaagggaaa gtgaatggcg ctgttaagtc gtgcactgtg 1441 agattgggtc agctaaggag tctcaagaga ggaaattttg ataccaatgc ttgtctctgg 1501 atgtctggtt tgaatgtcgt tgatcttgct agatggaggg cattgggtgt ttcagaaacc 1561 tatcaaaaat attataaaga gatgagtagt ggagatgagt cgagcgaagc aattgcattg 1621 caggcaagct tgctcacatt tcaagaccaa gtatatgctc ttgacgacaa atgggctcta 1681 tcagggcttg gttatgacta ctacatcaat gcacaagcca taaaaaacgc agccatattg 1741 cactataacg ggaacatgaa gccgtggctt gagctgggaa tcccaaatta caaaaactat 1801 tggagaaggc atctgagtcg ggaagatcgg ttcttgagtg actgtaacgt gaatccttga
```

Amino Acid Sequence of Sequence #2: (SEQ ID NO:4)
GeneBank ID# NP_565893
Positions 1-619 of NP_565893.

```
  1 mkgggggggg ggggkrrwkv lvigvlvlvi lsmlvplafl lgthngfhsp gfvtvqpass 61 fesftrinat khtqrdvser vdevlqkinp vlpkksdinv gsrdvnatsg tdskkrglpv 121 sptvvanpsp anktkseasy tgvqrkivsg detwrtcevk ygsyclwree nkepmkdakv 181 kqmkdqlfva rayypsiakm psqskltrdm kqniqeferi lsessqdadl ppqvdkklqk 241 meaviakaks fpvdcnnvdk klrqildlte deasfhmkqs vflyqlavqt mpkslhclsm 301 rltvehfksd sledpisekf sdpsllhfvi isdnilassv vinstvvhar dsknfvfhvl 361 tdeqnyfamk qwfirnpckq stvqvlniek lelddsdmkl slsaefrvsf psgdllasqq 421 nrthylslfs qshyllpklf dklekvvild ddvvvqrdls plwdldmegk vngavksctv 481 rlgqlrslkr gnfdtnaclw msglnvvdla rwralgvset yqkyykemss gdesseaial 541 qaslltfqdq vyalddkwal sglgydyyin aqaiknaail hyngnmkpwl elgipnykny 601 wrrhlsredr flsdcnvnp
```

Sequence #3 (SEQ ID NO:5)
Gene name: At5g47780
GeneBank accession # for reference: NM_124152 GI:30695292
Nucleotide sequence of Sequence #3:
Positions 1-1851 of CDS of NM_124152.

```
  1 atgatggtga agcttcgcaa tcttgttctt ttcttcatgc tcctcaccgt cgttgctcat 61 atccttctct acaccgatcc cgctgcctcc ttcaagaccc cctttctaa cgcgatttc 121 ctcgaggacg taaccgcctt gactttcaat tccgatgaga atcgtttgaa tcttcttcct 181 cgggaatctc ccgctgtgct cagaggagga ctcgtcggtg ctgtctattc cgataagaat 241 tcacggcggc tagaccaatt gtctgctcga gttctttccg ccaccgacga tgatactcac 301 tcacatactg acatttccat caaacaagtc actcatgatg cagcctcaga ctcgcatatt 361 aatagggaaa atatgcatgt tcaattgacc caacaaacct ctgaaaaagt tgatgagcaa 421 ccagagccta atgcttttgg agctaagaaa gatactggaa acgtgttgat gcctgatgct 481 caagtgaggc atcttaaaga tcagcttatt agggcaaagg tttatctttc ccttccatct 541 gcaaaggcca atgctcattt tgtgagagag cttcgactcc gtattaaaga agttcaacgg 601 gcacttgcag atgcctccaa ggattcggat ctgccaaaga ctgctataga aaagctaaaa 661 gcaatggagc aaacactggc caaaggcaag cagatccaag atgactgttc tacagtggtc 721 aagaagctac gtgctatgct ccactccgca gatgagcagc tacgggtcca taagaagcaa
```

-continued

```
 781 accatgtttt tgactcaatt gactgctaag accattccta aaggacttca ctgccttcct 841 ctgcgcctca ctacagacta ttatgcttta aattcatctg aacaacaatt tccaaatcag 901 gagaaactag aagatactca gctgtatcac tatgcccttt tctctgataa tgttttggct 961 acgtcagttg ttgttaactc taccataacc aatgcaaagc atcccttaaa gcatgtcttc 1021 cacatcgtca cagacagact caattatgcg gcaatgagga tgtggttcct ggacaatcca 1081 cctggcaaag ccaccatcca ggttcagaat gttgaagaat ttacatggct gaattcaagc 1141 tacagtcccg ttctcaaaca gcttagttct agatcgatga tagattatta cttcagagcc 1201 caccatacaa attcagacac caacttgaag ttccggaatc caaaatactt atcgatcctt 1261 aatcatcttc gttttttactt gcctgagatc tttcccaagc tcagcaaagt gctcttcttg 1321 gatgatgata tagttgtgca gaaggacctt tctggtcttt ggtcagttga tctgaaaggt 1381 aatgttaacg gtgctgtaga gacgtgtggg gaaagctttc atcgctttga ccgttatctg 1441 aacttctcaa atccactcat ttccaagaac tttgaccctc gagcttgtgg ttgggcgtat 1501 ggtatgaatg tctttgatct ggatgaatgg aagaggcaaa acatcacaga gtttatcat 1561 cgatggcagg atctgaatca agaccgaaaa ttgtggaagc tagggacgtt gccgcctggt 1621 ctaatcacat tttggagacg aacatatccg ctagaccgga aatggcacat actagggctt 1681 ggatacaacc cgagtgtgaa ccaaagggat attgagaggg cagccgtgat acactataat 1741 ggcaacctca aaccatggct agagattggg attccaagat acagaggctt ctggtcaaag 1801 catgtagact atgagcacgt ttatctcaga gaatgcaaca tcaatcctta g
```

Amino Acid Sequence of Sequence #3: (SEQ ID NO:6)
Genebank ID# NP_568688
Positions 1-616 of NP_568688.

```
  1 mmvklrnlvl ffmlltvvah illytdpaas fktpfskrdf ledvtalffn sdenrlnllp 61 respavlrgg lvgavysdkn srrldqlsar vlsatdddth shtdisikqv thdaasdshi 121 nrenmhvqlt qqtsekvdeq pepnafgakk dtgnvlmpda qvrhtkdqli rakvylslps 181 akanahfvre lrlrikevqr aladaskdsd lpktaieklk ameqtlakgk qiqddcstvv 241 kklramlhsa deqlrvhkkq tmfltqltak tipkglhclp lrlttdyyal nsseqqfpnq 301 ekledtqlyh yalfsdnvla tsvvvnstit nakhplkhvf hivtdrlnya amrmwfldnp 361 pgkatiqvqn veeftwlnss yspvlkqlss rsmidyyfra hhtnsdtnlk frnpkylsil 421 nhlrfylpei fpklskvlfl dddivvqkdl sglwsvdlkg nvngavetcg esfhrfdryl 481 nfsnpliskn fdpracgway gmnvfdldew krqnitevyh rwqdtnqdre lwklgtlppg 541 litfwrrtyp ldrkwhilgl gynpsvnqrd ieraavihyn gnlkpwleig ipryrgfwsk 601 hvdyehvylr ecninp
```

Sequence #4 (SEQ ID NO:7)
Gene name: At1g06780
GeneBank accession # for reference: NM_100555 GI:30679825
Nucleotide sequence of Sequence #4:
Positions 1-1770 of CDS of NM_100555.

```
  1 atgaaacaaa ttcgtcgatg gcagaggatt ttgatcctcg ctctgctatc gatatcagta 61 ttcgctccgc ttattttcgt atcgaatcgg cttaagagca tcactcccgt tggtcgtaga 121 gaatttattg aagagttatc caaaattaga ttcacgacaa atgaccttag acttagcgct 181 attgaacatg aggatggaga aggcttgaag gggccaaggc tcattctctt caaggatggg 241 gagtttaatt cgtctgctga aagtgatggt ggtaatactt acaaaaacag ggaagaacaa 301 gtgattgttt cacagaagat gacagttagc tctgatgaaa agggtcaaat tctaccaaca 361 gtcaaccaac ttgctaataa aacggatttc aagccccctt tatctaaggg tgaaaagaac
```

-continued

```
 421 acaagggttc agcccgacag agcaacagat gtgaaaacga aggagatcag agacaaaatt
 481 attcaagcta aagcctacct gaatttcgct ccacctggaa gtaactctca agttgtgaag
 541 gagttgagag gtcggctgaa agagctggaa cggtctgttg gtgatgcaac aaaggacaag
 601 gacttatcaa agggcgctct ccgcagggtg aagcccatgg aaaatgtgtt atataaggct
 661 agtcgtgtct ttaacaattg ccctgccatc gctaccaaac tccgtgccat gaattataac
 721 acagaagaac aagttcaggc gcagaaaaat caagcagcgt atctaatgca gcttgcagca
 781 aggaccaccc caaaagggct tcactgtctc tcaatgcggc tgacatcaga atacttttca
 841 ctggatcctg aaaaaggca gatgcctaac agcaaaatt attttgacgc taatttcaat
 901 cattatgttg tcttctctga caatgttttg gcttcttcag tcgttgttaa ctctacgata
 961 tcttcatcaa aggagccaga agaatagtc ttccatgtcg tgactgattc acttaattac
1021 ccagcaatct caatgtggtt tctgctaaac attcaaagta aagctactat ccaaatccta
1081 aacattgatg atatggatgt cctgcctaga gattatgatc aattactgat gaagcaaaac
1141 tctaatgacc caagattcat ttctacactc aatcacgcac gcttctatct cccggatata
1201 ttcccgggtt tgaacaagat ggtactcttg gaccatgatg tagttgttca aagagattta
1261 agtagactgt ggagcattga tatgaaagga aaggtggttg gagctgtaga gacttgtctt
1321 gaaggtgaat cttcatttcg atcaatgagc acatttatta atttctcaga cacatgggtc
1381 gctgggaaat ttagtcctag agcttgcaca tgggctttcg ggatgaatct aattgatctc
1441 gaagaatgga gaatacggaa gttgacttct acatacataa aatacttcaa cctgggaaca
1501 aagagaccat tgtggaaagc tgggagctta ccaataggtt ggttgacttt ctataggcaa
1561 acattagcat tggacaagag atggcatgtg atggggttag gtcgcgaatc aggagtcaaa
1621 gcggttgaca tcgaacaagc ggcagttata cactacgatg gggtcatgaa gccgtggttg
1681 gacattggaa aagagaatta caaacgttac tggaacatac acgtcccta ccatcacacc
1741 tacttgcaac agtgcaatct tcaagcttga
```

Amino Acid Sequence of Sequence #4: (SEQ ID NO: 8)
Genebank ID# NP_563771
Positions 1-589.

```
  1 mkqirrwqri lilallsisv faplifvsnr lksitpvgrr efieelskir fttndlrlsa
 61 iehedgeglk gprlilfkdg efnssaesdg gntyknreeq vivsqkmtvs sdekgqilpt
121 vnqlanktdf kpplskgekn trvqpdratd vktkeirdki iqakayinfa ppgsnsqvvk
181 elrgrtkele rsvgdatkdk dlskgalrrv kpmenvlyka srvfnncpai atklramnyn
241 teeqvqaqkn qaaylmqlaa rttpkglhcl smrltseyfs ldpekrqmpn qqnyfdanfn
301 hyvvfsdnvl assvvvnsti ssskeperiv fhvvtdslny paismwflln iqskatiqil
361 niddmdvlpr dydqllmkqn sndprfistl nharfylpdi fpglnkmvll dhdvvvqrdl
421 srlwsidmkg kvvgavetcl egessfrsms tfinfsdtwv agkfspract wafgmnlidl
481 eewrirklts tyikyfnlgt krplwkagsl pigwltfyrq tlaldkrwhv mglgresgvk
541 avdieqaavi hydgvmkpwl digkenykry wnihvpyhht ylqqcnlqa
```

Sequence #5 (SEQ ID NO:9)
Gene name: At1g18580
GeneBank accession # for reference: AY062444 GI:17064735
Nucleotide sequence of Sequence #5:
Positions 1-1614 of CDS of AY062444.

```
  1 atgaggcggt ggccggtgga tcaccggcgg cgaggtagaa ggagattgtc gagttggata
 61 tggtttctcc ttggttcttt ctctgtcgct ggtttagttc tcttcatcgt tcagcattat
121 caccatcaac aagatccatc ccagctttta cttgagagag cacgagaaac cgaaatggta
```

-continued

```
 181 tctcctcccc atttaaactt cacggaagag gtcacaagtg cttcctcctt ctctaggcag 241 ttagcagagc aaatgacact tgccaaagct tatgtgttta tagctaaaga gcataataat 301 cttcatttag cttgggaatt gagttctaag atcagaagtt gtcagttttt gctttccaaa 361 gcagctatga gaggacaacc tatttcgttt gatgaggcta aaccgattat tactggtcta 421 tcagctctta tctacaaggc tcaagatgca cattatgata ttgccaccac tatgatgacc 481 atgaaatctc acatccaagc acttgaagag cgtgcaaatg cagctactgt tcagaccaca 541 atatttgggc aattggttgc tgaggcatta ccaaagagcc tccactgttt gacgataaag 601 ctcacatctg attgggtaac agagccatct cgccatgaac tggcagatga aacagaaac 661 tcacctagac ttgtcgacaa caacctctac cacttctgca tcttctcgga caacgtgatt 721 gccacctcgg ttgttgttaa ttcaactgtc tcgaatgctg atcatccaaa gcagcttgtt 781 ttccacatag tgacgaatcg agtgagctac aaagctatgc aggcctggtt tctaagtaat 841 gacttcaagg gctcagcaat agagatcagg agcgtagagg agttttcttg gttgaatgct 901 tcatattctc ctgttgttaa gcaactgctg gacacagatg caagagctta ctatttcggg 961 gaacagacaa gtcaagatac gatttccgag ccaaaagtga ggaacccaaa gtacttgtca 1021 ttactgaacc atctcagatt ctacattccg gagatctatc cacagctaga gaagattgtt 1081 ttcctagacg atgatgttgt tgttcagaaa gatttgactc cactcttctc cttggatctg 1141 catggaaacg tcaatggagc tgtggaaaca tgtcttgaag cctttcaccg atattacaag 1201 tatctaaatt tctcgaaccc actcatcagc tcaaagttcg acccacaagc atgtggatgg 1261 gcttttggta tgaacgtttt tgatctgatc gcttggagga tgcaaacgt gactgctcgg 1321 taccattact ggcaagatca gaacagagaa cgaacgcttt ggaaactcgg gacactccct 1381 ccaggtctac tatctttcta tggtctcaca gagccactgg acagaagatg gcatgtcttg 1441 ggtttaggtt acgatgtgaa catcgataac cgtctgatcg aaacagcagc tgtgattcac 1501 tataatggta acatgaagcc ttggctaaag ctggctattg gtaggtataa acctttctgg 1561 ttaaagtttt tgaactcgag ccatccttat ttacaagatt gtgtcacagc ttaa
```

Amino Acid Sequence of Sequence #5: (SEQ ID NO: 10)
Genebank ID# AAK93644 GI:15293067
Positions 1-537 of AAK93644.

```
   1 mrrwpvdhrr rgrrrlsswi wfllgsfsva glvlfivqhy hhqqdpsqll lerdtrtemv 61 spphlnftee vtsassfsrq laeqmtlaka yvfiakehnn lhlawelssk irscqlllsk 121 aamrgqpisf deakpiitgl saliykaqda hydiattmmt mkshiqalee ranaatvqtt 181 ifgqlvaeal pkslhcltik ltsdwvteps rheladenrn sprlvdnnly hfcifsdnvi 241 atsvvvnstv snadhpkqlv fhivtnrvsy kamqawflsn dfkgsaieir sveefswlna 301 syspvvkqll dtdarayyfg eqtsqdtise pkvrnpkyls linhirfyip eiypqlekiv 361 flddvvvvqk dltplfsldl hgnvngavet cleafhryyk ylnfsnplis skfdpqacgw 421 afgmnvfdli awrnanvtar yhywqdqnre rtlwklgtlp pgllsfyglt epldrrwhvl 481 glgydvnidn rlietaavih yngnmkpwlk laigrykpfw lkflnsshpy lqdcvta
```

Sequence #6 (SEQ ID NO: 11)
Gene name: At2g20810
GeneBank accession # for reference: NM_127647 GI:30681142
Nucleotide sequence of Sequence #6:
Positions 1-1611 of CDS of NM_127647.

```
   1 atgagaagga gaggagggga tagtttccgg agagctggac ggaggaagat ctcgaatgtg 61 gtatggtggg ttctctctgg tattgccctc ctgctcttct ttctcattct ctccaaagct 121 ggtcatattg aacctagacc ctctattcct aagcgacgtt accgtaatga caaatttgta
```

-continued

```
 181 gagggtatga atatgactga ggaaatgttg agtcctactt ccgttgctcg tcaagttaat
 241 gatcagattg ctcttgctaa agcttttgtt gtcattgcta aagaaagtaa gaatcttcag
 301 tttgcttggg acttaagtgc tcagatccgt aactctcagt tgcttttatc gagtgctgct
 361 actaggagaa gtcccttgac tgtcttggaa tctgagtcta ctattcgtga catggctgtt
 421 ttgttatatc aagctcagca gcttcactat gatagtgcta ctatgattat gaggcttaag
 481 gcctcgattc aggctcttga agaacaaatg agttccgtta gcgagaagag ttccaagtat
 541 ggacagattg ctgctgagga agtgcctaag agtctttact gtcttggtgt tcgtctcact
 601 accgaatggt ttcagaattt agacttacag agaactctta aggaaaggag tcgtgttgat
 661 tcgaaactca cggataacag tctctaccat ttctgtgtgt tttccgataa cattattgct
 721 acttctgttg tggttaattc tactgctctc aattccaagg cccctgagaa agttgtgttt
 781 catcttgtga ctaatgagat caactatgct gcaatgaagg cttggttcgc cattaatatg
 841 gacaacctca gaggagtcac tgtggaggtt cagaagttcg aggatttctc atggctgaat
 901 gcttcctatg ttccggtcct caagcagctg caagactctg atacgcaaag ctattatttc
 961 tctggacaca cgatgatgg gcgcactcca atcaaattca ggaaccccaa gtatctttcc
1021 atgctcaacc atcttaggtt ctacatccct gaagtgtttc ctgcgctgaa gaaggtggtc
1081 tttcttgatg atgatgttgt agttcagaag gatctttcat ctctcttttc gatcgattta
1141 aacaaaaatg tgaacggggc tgttgagacc tgcatggaga ccttccaccg ctaccacaag
1201 tacttgaact attctcatcc tctcatacgc tcccactttg atccagatgc gtgtgggtgg
1261 gcgtttggaa tgaacgtctt tgatttagtt gagtggagga agaaaatgt gaccggcata
1321 taccactact ggcaagaaaa aaacgtggac cggacttat ggaaactggg aacactacct
1381 ccaggacttc tgacatttta cgggttaaca gaggcactag aggcgtcctg gcatatcctg
1441 ggattgggat acacgaatgt ggatgctcgt gtgatagaga aaggagctgt tcttcacttc
1501 aatgggaact aaagccatg gttgaagatc gggatagaga agtacaaacc tttgtgggag
1561 agatacgttg attacacttc tccttttatg caacaatgca attttcattg a
```

Amino Acid Sequence of Sequence #6: (SEQ ID NO: 12)
Genebank ID# NP_565485
Positions 1-536 of NP_565485.

```
   1 mrrrggdsfr ragrrkisnv vwwvlsgial llffflulska ghieprpsip krryrndkfv
  61 egmnmteeml sptsvarqvn dqialakafv viakesknlq fawdisaqir nsqlllssaa
 121 trrspltvle sestirdmav llyqaqqlhy dsatmimrlk asiqaleeqm ssvsekssky
 181 gqiaaeevpk slyclgvrlt tewfqnldlq rtlkersrvd skltdnslyh fcvfsdniia
 241 tsvvvnstal nskapekvvf hlvtneinya amkawfainm dnlrgvtvev qkfedfswln
 301 asyvpvlkql qdsdtqsyyf sghnddgrtp ikfrnpkyls minhirfyip evfpalkkvv
 361 fldddvvvqk dlsslfsidl nknvngavet cmetfhryhk ylnyshplir shfdpdacgw
 421 afgmnvfdlv ewrkrnvtgi yhywqeknvd rtlwktgtlp pglltfyglt eateaswhil
 481 glgytnvdar viekgavlhf ngnlkpwlki giekykplwe ryvdytspfm qqcnfh
```

Sequence #7 (SEQ ID NO: 13)
Gene name: At2g30575
GeneBank accession # for reference: NM_179819 GI:30684641
Nucleotide sequence of Sequence #7:
Positions 1-1833 of NM_179819.

```
   1 atgaatcaag ttcgtcgttg gcagaggatt ctgatcctct cgctgctatt gttatctgtt
  61 ttagctccga ttgttttcgt ttcgaatcgg ctcaagagca tcacttccgt cgatagagga
 121 gaattcattg aagaattatc cgacattaca gataagaccg aggatgaact tagacttact
```

-continued

```
 181 gctattgaac aggacgaaga aggcttgaag gagcctaaac gtattctgca ggatcgagat 241 tttaattctg tggttttgtc aaattcctct gataaaagta atgatactgt gcagtctaat 301 gagggagacc aaaaaaactt tctctcagaa gttgataagg gaaataatca aaaccaaag 361 gaggaacaag cagtttcaca gaaaaccaca gtaagctcga atgcggaggt gaaaatttca 421 gcaagagata ttcaacttaa tcataaaacg gaattccgac ccccttcaag taagagtgaa 481 aagaatacaa gggttcaact tgaaagagca acagatgaga gggtaaagga gatcagagac 541 aaaattatcc aagcgaaagc ctatctgaat ttggccctac ctgggaataa ctcccaaatc 601 gtaaaggagt tgagagttcg aacgaaagag ctggaacggg ctactggtga tactaccaag 661 gataaatatt tgccaaagag ctctcctaac agattgaagg ccatggaagt tgcgttatac 721 aaggtcagcc gtgcctttca caactgccct gccattgcta ccaaactcca agccatgact 781 tataaaaccg aagaacaagc tcgggcgcag aagaaacaag cagcatattt aatgcagctt 841 gcagcaagga ctaccccaaa agggcttcat tgtctctcaa tgcggttgac aacagaatat 901 tttaccctgg atcacgaaaa aaggcagctt ttgcaacaaa gttataatga tcctgatctc 961 taccattacg tagtcttctc tgacaatgtt ttggcctctt cggttgttgt taactctaca 1021 atctcctcat caaaggaacc ggataaaata gtattccatg tggtgacaga ttcactcaat 1081 tacccagcaa tctcaatgtg gttttttacta aacccaagtg gcagagcttc aatccaaatc 1141 ctaaacattg atgaaatgaa tgtcctgcca ttgtaccatg ctgaattgct gatgaagcaa 1201 aattcaagtg acccaagaat catttcagcg ctcaaccatg cacgcttcta tctcccagat 1261 atcttcccag gtctaaacaa gatcgtactc ttcgatcatg atgtagtagt gcaaagggat 1321 ctaactagac tgtggagcct tgatatgacg gggaaagttg ttggagctgt agagacttgt 1381 cttgaaggtg atccttcata tcgttcgatg gactcattca ttaatttctc agatgcatgg 1441 gtttctcaga aatttgatcc caaggcttgc acttgggcat tcgggatgaa tctatttgat 1501 ctcgaagaat ggagaagaca ggagttgact tctgtatacc tgaaatactt cgacctggga 1561 gtaaaaggac atctgtggaa agcaggggga ttgccagtag ttggttgac tttttttcggg 1621 caaacgtttc cgttggaaaa gagatggaac gtgggtgggt taggtcacga atcaggactc 1681 agggcaagcg acatcgaaca agcagcggtt atacactacg acgggatcat gaaaccatgg 1741 ctggacatcg gtatagacaa gtacaagcgc tactggaaca tacatgtacc ttaccatcac 1801 cctcacttac aacggtgcaa cattcacgat tga
```

Amino Acid Sequence of Sequence #7: (SEQ ID NO: 14)
Genebank ID# NP_850150
Positions 1-610 of NP_850150.

```
   1 mnqvrrwqri lilsllllsv lapivfvsnr lksitsvdrg efieelsdit dktedelrlt 61 aieqdeeglk epkrilqdrd fnsvvlsnss dksndtvqsn egdqknflse vdkgnnhkpk 121 eeqavsqktt vssnaevkis ardiqlnhkt efrppssksk kntrvqlera tdervkeird 181 kiiqakayln lalpgnnsqi vkelrvrtke leratgdttk dkylpksspn rikamevaly 241 kvsrafhncp aiatklqamt ykteeqaraq kkqaaylmql aarttpkglh clsmrittey 301 ftldhekrql lqqsyndpdl yhyvvfsdnv lassvvvnst isssskepdki vfhvvtdsln 361 ypaismwfll npsgrasiqi lnidemnvlp lyhaellmkq nssdpriisa lnharfylpd 421 ifpglnkivl fdhdvvvqrd ltrlwsldmt gkvvgavetc legdpsyrsm dsfinfsdaw 481 vsqkfdpkac twafgmnlfd leewrrqett svylkyfdlg vkghlwkagg lpvgwltffg 541 qtfplekrwn vgglghesgl rasdieqaav ihydgimkpw ldigidkykr ywnihvpyhh 601 phlqrcnihd
```

-continued

Sequence #8 (SEQ ID NO: 15)
Gene name: At2g46480
GeneBank accession # for reference: NM_130212 GI:22326493
Nucleotide sequence of Sequence #8:
Positions 1-1587 of NM_130212.

```
   1 atgactgatg cttgttgttt gaagggaaac gaggacaaaa tggttcctcg ttttggtcat 61 ggaacctgga taggaaaagc atttaatgat acaccagaga tgttgcatga aggagtctg 121 agacaggaaa aagattgga aagggctaat gagctgatga atgatgatag tctgcaaaag 181 cttgagacgg cagccatggc acgttccaga tctgtcgatt ctgcaccact aggaaactac 241 accatttgga aaatgaata ccggaggggc aagagttttg aagatatgtt acgtttgatg 301 caagatcaaa tcatcatggc acgagtttac agtggacttg caaagtttac aaacaatctc 361 gccttgcacc aagagataga aacacaacta atgaaactag cttgggagga agaatctact 421 gatattgatc aggagcagag agtacttgac agtataagag acatgggaca aatactggct 481 agagcacacg agcagctata tgaatgcaag ttggtgacaa ataagttgag agcaatgcta 541 caaacagttg aagatgaact cgaaaacgag cagacttata taacgttctt gactcagcta 601 gcttccaagg cactaccaga tgctatccac tgcttgacca tgcgcttgaa tctagagtat 661 catctcctgc ctttaccgat gagaaatttt ccaaggaggg agaatttgga gaatccaaaa 721 ctttaccact acgctctctt ctctgataat gtactggctg catcagttgt tgtcaactcc 781 acagtcatga atgcacagga tccttcaagg catgttttcc accttgtgac tgataagctc 841 aactttggag caatgagtat gtggtttctg ttgaaccctc ctggagaagc gaccatccat 901 gtccaaaggt ttgaagattt tacttggctc aactcatctt actctccagt tttgagtcag 961 ctcgagtcag cagctatgaa gaagttctac ttcaagacag cgaggtctga atcagttgaa 1021 tcaggctcag aaaacctcaa gtaccggtac ccgaaataca tgtcaatgct taaccacctg 1081 aggttctaca tccctaggat cttcccaaag ttggagaaaa tcttgtttgt tgacgatgat 1141 gtggttgttc agaaggattt aactcccta tggtccattg atcttaaagg gaaagtgaat 1201 gaaaactttg atcccaagtt ctgcggatgg gcttatggga tgaacatctt cgacctgaaa 1261 gaatggaaga agaacaacat tacagaaact tatcactttt ggcaaaacct gaacgaaaac 1321 cggactctat ggaaactagg aacattgcca ccagggctca taacgttcta caatctgaca 1381 caaccacttc agagaaaatg gcacttactt ggactgggtt atgataaagg aatcgatgtc 1441 aagaagattg aaagatcagc tgttatacat tacaatggac acatgaaacc atggacagag 1501 atggggataa gcaagtatca gccatattgg acgaagtaca ccaattttga ccatccttac 1561 atctttactt gcaggctgtt tgagtga
```

Amino Acid Sequence of Sequence #8: (SEQ ID NO: 16)
Genebank ID# NP_182171
Positions 1-528 of NP_182171.

```
   1 mtdacclkgn edkmvprfgh gtwigkafnd tpemlhersl rqekrleran elmnddslqk 61 letaamarsr svdsaplgny tiwkneyrrg ksfedmlrlm qdqiimarvy sglakftnnl 121 alhqeietql mklaweeest didqeqrvld sirdmgqila raheqlyeck lvtnklraml 181 qtvedelene qtyitfltql askalpdaih cltmrlnley hllplpmrnf prrenlenpk 241 lyhyalfsdn vlaasvvvns tvmnaqdpsr hvfhlvtdkl nfgamsmwfl lnppgeatih 301 vqrfedftwl nssyspvlsq lesaamkkfy fktarsesve sgsenlkyry pkymsmlnhl 361 rfyiprifpk lekilfvddd vvvqkdltpl wsidlkgkvn enfdpkfcgw aygmnifdlk 421 ewkknnitet yhfwqnlnen rtlwklgtlp pglitfynlt qplqrkwhll gtgydkgidv 481 kkiersavih ynghmkpwte mgiskyqpyw tkytnfdhpy iftcrlfe
```

-continued

Sequence #9 (SEQ ID NO: 17)
Gene name: At3g01040
GeneBank accession # for reference: NM_110969 GI:30678269
Nucleotide sequence of Sequence #9:
Positions 1-1602 of CDS of NM_110969.

```
   1 atgcagcttc acatatcgcc tagcatgaga agcattacga tatcgagcag caatgagttt 61 attgatttga tgaagatcaa agtcgcagct cgtcacatct cttaccgaac tctcttccac 121 actatcttaa tcctcgcttt cttgttacct tttgttttca tcctaaccgc tgttgttacc 181 cttgaaggtg tcaacaagtg ctcctctttt gattgtttcg ggaggcggct aggaccacgt 241 cttcttggta ggatagatga ttcagagcag agactagtta gagattttta caaaattcta 301 aatgaagtaa gcactcaaga aattccagat ggtttaaagc ttccagagtc ttttagtcaa 361 ctggtttcgg atatgaagaa caaccactat gatgctaaaa catttgccct cgtatttcga 421 gctatggtag agaagtttga aggggattta agggaatcca aatttgcaga actcatgaac 481 aagcactttg ctgcaagttc aattccaaaa ggaattcact gtctctcttt aagactaacc 541 gatgaatatt cctccaatgc tcatgcccgg agacagcttc cttccccgga gcttctccct 601 gttctctcag acaatgctta ccaccatttt gttctagcta cagataatat cttagctgca 661 tcggttgtgg tctcatctgc tgttcaatca tcttcaaaac ccgagaaaat tgtcttccat 721 gttatcacag acaagaaaac ctatgcgggt atgcattctt ggtttgcact caattctgtt 781 gctcctgcga ttgttgaagt gaaaagcgtt catcagtttg attggttaac aagagagaat 841 gttccagttc ttgaagctgt ggaaagccat aacagtatca gaattattat ccatgggaat 901 catattgctg gtgcaaaacct cagcgaaaca accctcgaa catttgcttc gaaactgcag 961 tcaagaagtc ccaaatacat atctttgctc aaccatctta aatatatct accagagctt 1021 tttccgaact agacaaggt agtgttctta gatgatgata tagtgataca gaaagattta 1081 tctccgcttt gggatattga ccttaacggg aaggttaatg gagctgtgga gacttgtcga 1141 ggagaagacg tatgggttat gtcaaagcgt cttaggaact acttcaattt ttctcacccg 1201 ctcatcgcaa agcatttaga tcccgaagaa tgtgcttggg cttatggaat gaatatcttt 1261 gatctacgga cttggaggaa gacaaatatc agagaaacgt atcattcttg gcttaaagag 1321 aatctgaagt cgaatctaac aatgtggaaa cttggaacat tgcctcctgc tctaatagca 1381 tttaaaggtc atgttcagcc aatagattcc tcttggcata tgcttggatt aggttatcag 1441 agcaagacca acttagaaaa tgcgaagaaa gctgcagtga ttcattacaa tggccaatca 1501 aagccgtggc ttgagatagg tttcgagcat ctcagaccat tctggacaaa atatgttaac 1561 tactccaatg atttcattaa gaattgtcat atcttggaat ag
```

Amino Acid Sequence of Sequence #9: (SEQ ID NO: 18)
Genebank ID# NP_186753
Positions 1-533 of NP_186753.

```
   1 mqlhispsmr sitisssnef idlmkikvaa rhisyrtlfh tililaflip fvfiltavvt 61 legvnkcssf dcfgrrlgpr llgriddseq rlvrdfykil nevstqeipd glklpesfsq 121 lvsdmknnhy daktfalvfr amvekferdl reskfaelmn khfaassipk gihclslrlt 181 deyssnahar rqlpspellp vlsdnayhhf vlatdnilaa svvvssavqs sskpekivfh 241 vitdkktyag mhswfalnsv apaivevksv hqfdwltren vpvleavesh nsirnyyhgn 301 hiaganlset tprtfasklq srspkyisll nhlriylpel fpnldkvvfl dddiviqkdl 361 splwdiding kvngavetcr gedvwvmskr lrnyfnfshp liakhldpee cawaygmnif 421 dlrtwrktni retyhswlke nlksnltmwk lgtlppalia fkghvqpids swhmlglgyq 481 sktnlenakk aavihyngqs kpwleigfeh lrpfwtkyvn ysndfiknch ile
```

-continued

Sequence #10 (SEQ ID NO: 19)
Gene name: At3g02350
GeneBank accession # for reference: NM_111102 GI:18396158
Nucleotide sequence of Sequence #10:
Positions 1-1686 of CDS of NM_111102.

```
   1 atggcggtgg ccttccgtgg aggccgggga ggcgtcggat ccggccaatc taccggactt 61 cgtagtttct tctcctaccg gatctttatc tccgctttgt tctcttttct cttcctcgcc 121 actttctccg tcgttcttaa ctcctctcgt catcagcctc atcaggatca tacattgccg 181 agtatgggca acgcatatat gcagaggacg tttttggctt tgcaatcgga tccattgaaa 241 actaggttgg atctgataca caagcaagcc attgatcatt tgacactggt gaatgcgtat 301 gctgcttacg ctaggaagct aaagcttgat gcttctaagc agcttaagct cttcgaagat 361 ttggctatca acttctcgga tttgcagtcg aaacctggtt tgaaatctgc tgtgtctgat 421 aatggtaatg ctcttgagga ggattcgttt aggcagcttg agaagaagt gaaggataag 481 gtgaagacag cgaggatgat gatcgttgag tctaaagaga gttatgatac acagcttaaa 541 atccagaagt tgaaagatac aatctttgct gtccaagaac agttgacaaa ggctaagaaa 601 aacggtgcgg ttgctagctt gatttcagcc aagtcggttc ctaaaagtct tcattgtttg 661 gccatgaggc ttgtaggaga gaggatctct aatcctgaga agtacaagga tgctccacct 721 gacccagccg cagaggatcc aactctttac cactatgcga tttctctga taatgtcatt 781 gctgtgtctg ttgtggtgag atcggttgtg atgaacgctg aggagccatg gaagcatgtc 841 ttccatgtgg tgacagatcg gatgaatctc gcagccatga aggtgtggtt taagatgcgt 901 cctttggacc gtggtgccca tgttgagatt aaatccgtgg aggatttcaa gttcttaaac 961 tcttcctatg cgccggtctt gaggcagctt gagtctgcca agttgcagaa gttttacttt 1021 gagaatcaag ctgagaacgc aactaaagat tcacataacc tcaagttcaa gaaccccaag 1081 tatctctcga tgttgaacca tctcagattt tacttaccag atgtgtatcc gaagctgaat 1141 aagattttgt tctggacga tgatgttgtg gtgcagaaag acgtgactgg tttatggaaa 1201 atcaacttgg atggcaaggt gaatggagcc gttgagacat gttttggttc ttttcatcga 1261 tatggtcaat acttaaactt ctctcatcct ttgatcaaag agaactttaa ccccagtgcc 1321 tgtgcttggg cctttggaat gaacatattc gatctcaatg cctggagacg cgagaagtgc 1381 accgatcaat accattactg gcagaacctg aatgaagaca gaactctctg gaaattggga 1441 actctacctc cgggattgat cacattctat tcaaagacga aatcattgga caaatcatgg 1501 catgtacttg ggttaggcta taacccggga gtgagcatgg acgaaatcag aaatgcagga 1561 gtgattcatt acaatggaaa catgaaaccg tggctagaca ttgcgatgaa ccaatacaag 1621 tctctctgga ctaaatatgt tgataacgaa atggagtttg tgcagatgtg caattttggt 1681 ctctaa
```

Amino Acid Sequence of Sequence #10: (SEQ ID NO: 20)
Genebank ID# NP_566170.1
Positions 1-561 of NP_566170.

```
   1 mavafrggrg gvgsgqstgl rsffsyrifi salfsflfla tfsvvlnssr hqphqdhtlp 61 smgnaymqrt flalqsdplk trldlihkqa idhltlvnay aayarklkld askqlklfed 121 lainfsdlqs kpglksavsd ngnaleedsf rqlekevkdk vktarmmive skesydtqlk 181 iqklkdtifa vqeqltkakk ngavaslisa ksvpksthcl amrlvgeris npekykdapp 241 dpaaedptly hyaifsdnvi avsvvvrsvv mnaeepwkhv fhvvtdrmnl aamkvwfkmr 301 pldrgahvei ksvedfkfln ssyapvlrql esaklqkfyf enqaenatkd shnlkfknpk 361 ylsmlnhlrf ylpemypkln kilflddddvv vqkdvtglwk inldgkvnga vetcfgsfhr
```

-continued

```
    421 ygqylnfshp likenfnpsa cawafgmnif dlnawrrekc tdqyhywqnl nedrtlwklg 481 tlppglitfy sktksldksw hvlglgynpg vsmdeirnag vihyngnmkp wldiamnqyk 541 slwtkyvdne mefvqmcnfg l Sequence#11 (SEQ ID NO: 21)
Gene name: at3g25140
GeneBank accession # for reference: NM_113418 GI:30687767
Nucleotide sequence of Sequence #11:
Positions 1-1680 of COS of NM_113418.
      1 atggctaatc accaccgact tttacgcggc ggcggatctc cggccataat cggtggcaga 61 atcacactca cagctttcgc ttccactatc gcactcttcc tcttcactct ctccttcttc 121 ttcgcttcag attctaacga ttctcctgat ctccttcttc ccggtgttga gtactctaat 181 ggagtcggat ctagaagatc catgttggat atcaaatcgg atccgcttaa gccacggttg 241 attcagatcc ggaaacaagc tgatgatcat cggtcattag cattagctta tgcttcttac 301 gcgagaaagc ttaagctcga gaattcgaaa ctcgtcagga tcttcgctga tctttcgagg 361 aattacacgg atctgattaa caaaccgacg tatcgagctt tgtatgattc tgatggagcc 421 tcgattgaag aatctgtgct taggcaattt gagaaagaag ttaaggaacg gattaaaatg 481 actcgtcaag tgattgctga agctaaagag tcttttgata atcagttgaa gattcagaag 541 ctgaaagata cgattttcgc tgttaacgaa cagttaacta atgctaagaa gcaaggtgcg 601 ttttcgagtt tgatcgctgc gaaatcgatt ccgaaggat tgcattgtct tgctatgagg 661 ctgatggaag agaggattgc tcaccctgag aagtatactg atgaagggaa agatagaccg 721 cgggagctcg aggatccgaa tctttaccat tacgctatat tttcggataa tgtgattgcg 781 gcttcggtgg ttgtgaactc tgctgtgaag aatgctaagg agccgtggaa gcatgttttt 841 cacgttgtga ctgataagat gaatcttgga gctatgcagg ttatgtttaa actgaaggag 901 tataaaggag ctcatgtaga agttaaagct gttgaggatt atacgttttt gaactcttcg 961 tatgtgcctg tgttgaagca gttagaatct gcgaatcttc agaagtttta tttcgagaat 1021 aagctcgaga tgcgacgaa agataccacg aatatgaagt tcaggaaccc caagtattta 1081 tctatattga atcacttgag gttttatttt cccgagatgt acccgaaact acataggata 1141 ctgttttttgg acgatgatgt ggttgtgcag aaggatttaa cgggtctgtg ggagattgat 1201 atggatggga aagtgaatgg agctgtagag acttgttttg ggtcgtttca tcggtacgct 1261 caatacatga atttctcaca tcctttgatc aaagagaagt ttaatcccaa agcatgtgcg 1321 tgggcgtatg aatgaacttt cttttgatctt gatgcttgga gaagagagaa gtgcacagaa 1381 gaatatcact actggcaaaa tctgaacgag aacagggctc tatggaaact ggggacgtta 1441 ccaccgggac tgatcacctt ttactcaacc acaaagccgc tggacaaatc atggcatgtg 1501 cttgggctgg gttacaatcc gagcattagc atggatgaga tccgcaacgc tgcagtggta 1561 cacttcaacg gtaacatgaa gccatggctt gacatagcta tgaaccagtt tcgaccactt 1621 tggaccaaac acgtcgacta tgacctcgag tttgttcagg cttgcaattt tggcctctga Amino Acid Sequence of Sequence #11: (SEQ ID NO: 22)
Genebank ID# NP_189150
Positions 1-559 of NP_189150.
      1 manhhrllrg ggspaiiggr ititafasti alfiftlsff fasdsndspd lllpgveysn 61 gvgsrrsmld iksdplkprl iqirkqaddh rslalayasy arklklensk lvrifadlsr 121 nytdlinkpt yralydsdga sieesvlrqf ekevkerikm trqviaeake sfdnqlkiqk 181 lkdtifavne qltnakkqga fssliaaksi pkglhclamr lmeeriahpe kytdegkdrp 241 reledpnlyh yaifsdnvia asvvvnsavk nakepwkhvf hvvtdkmnlg amqvmfklke
```

```
301 ykgahvevka vedytflnss yvpvlkqles anlqkfyfen klenatkdtt nmkfrnpkyl 361 silnhlrfyl pemypklhri lflddddvvvq kdltglweid mdgkvngave tcfgsfhrya 421 qymnfshpli kekfnpkaca waygmnffdl dawrrekcte eyhywqnlne nralwklgtl 481 ppglitfyst tkpldkswhv lglgynpsis mdeirnaaw hfngnmkpwl diamnqfrpl 541 wtkhvdydle fvqacnfgl
```

Sequence #12 (SEQ ID NO: 23)
Gene name: At3g58790
GeneBank accession # for reference: NM_115741 GI:22331856
Nucleotide sequence of Sequence #12:
Positions 1-1623 of CDS of NM_115741.

```
   1 atgaagtttt acatatcagc gacggggatt aagaaggtta cgatatcaaa tcccggcgtc 61 ggaatcggta aaggaagcgg aggatgtgcg gctgcagcgg cggcgttagc agcgcggaga 121 ttctctagtc gcacgttgtt actgttgctg ctgctgctcg ctatcgtcct ccctttttatc 181 ttcgtcaggt tcgcgtttct cgtcctcgaa tctgcctccg tttgcgattc accactcgat 241 tgcatgggac tcagactttt ccgtggggc gacacatctc tgaaaattgg ggaagagttg 301 acacgggctc tagtggaaga cgacgacagat catcaggacg ttaatggaag aggaacgaag 361 ggatcattgg agtcattcga cgaccttgtt aaggagatga cgttaaaacg ccgtgacata 421 agggcgtttg cttccgtgac taagaagatg ctgttgcaga tggaacgtaa agtccaatca 481 gcgaaacatc atgagttagt gtactggcat ttagcctctc acggtattcc taaaagcctc 541 cattgccttt ccctcagatt aactgaagag tactctgtaa atgcaatggc tcgaatgcgt 601 ttgcctccgc ctgagtccgt atcacgtctg accgacccat cttttcatca tattgtcctc 661 ctgactgaca atgtccttgc tgcctctgtc gtcatatcgt ctactgtaca aaacgctgtg 721 aatcccgaga gtttgtcttt tcatattgtt accgataaga aaacctatac ccctatgcat 781 gcttggtttg ctatcaactc tgcttcatca ccagttgttg aagtaaaggg acttcatcag 841 tatgattggc ctcaagaagt gaacttcaaa gttagagaga tgctggacat tcaccgctta 901 atttggagac gacattatca aaatttgaaa gactctgatt ttagttttgt tgagggtact 961 catgagcagt ccttgcaagc tctaaatcct agctgccttg ccctttttgaa ccatcttcgc 1021 atttacattc caagcttttt tccagatctc aacaagatag tgttgttgga tgatgatgta 1081 gtagtacaga gcgatctttc gtctttatgg gaaacggatc tcaacggtaa agttgttggt 1141 gctgtcgttg attcgtggtg cggagacaac tgttgccccg gaagaaaata caaagactat 1201 ttcaacttct cacatccttt gatctcatca aacttagttc aagaagactg tgcttggctt 1261 tctggtatga atgtctttga tctcaaagcc tggagacaaa ccaatattac tgaagcttac 1321 tctacatggc taagactcag tgttaggtca ggactacaat tatggcaacc aggggcttta 1381 ccaccgacat tacttgcttt caaaggactt acacagtctc ttgaaccatc atggcacgtc 1441 gctggactag ttctcgatc cgtaaaatcc cctcaagaga ttctgaaatc tgcttcggtt 1501 ttacatttca gcggtccagc aaaaccgtgg ctagagatca gtaaccctga ggtacgatct 1561 ctttggtata gatacgtaaa ttcctccgac atcttcgtta gaaaatgcaa aatcatgaac 1621 tga
```

Amino Acid Sequence of Sequence #12: (SEQ ID NO: 24)
Genebank ID# NP_191438.2
Positions 1-540 of NP_191438.

```
   1 mkfyisatgi kkvtisnpgv gigkgsggca aaaalaarr fssrtllll lllaivlpfi 61 fvrfaflvle sasvcdspld cmglrlfrgg dtslkigeel tralveettd hqdvngrgtk 121 gslesfddlv kemtlkrrdi rafasvtkkm llqmerkvqs akhhelvywh lashgipksl
```

```
181 hclslrltee ysvnamarmr lpppesvsrl tdpsfhhivl ltdnvlaasv visstvqnav
241 npekfvfhiv tdkktytpmh awfainsass pvvevkglhq ydwpqevnfk vremldihrl
301 iwrrhyqnlk dsdfsfvegt heqstqalnp scialinhir iyipklfpdl nkivlldddv
361 vvqsdlsslw etdlngkvvg avvdswcgdn ccpgrkykdy fnfshpliss nlvqedcawl
421 sgmnvfdlka wrqtniteay stwlrlsvrs glqlwqpgal pptllafkgl tqslepswhv
481 aglgsrsvks pqeilksasv lhfsgpakpw leisnpevrs lwyryvnssd ifvrkckimn
```

Sequence#13 (SEQ ID NO: 25)
Gene name: At4g38270
GeneBank accession # for reference: NM_119989 GI: 30691874
Nucleotide sequence of Sequence #13
Positions 1-2043 of CDS of NM_119989.

```
   1 atgacgacgt tctctacatg cgccgccttt ttatcgctgg tagtagtgct acatgctgtt
  61 catgtcggtg gagccatttt agagtcacaa gcaccccaca gagaacttaa agcttatcgt
 121 ccgctgcaag ataataatct acaggaggtg tatgcttcct cagctgctgc agtgcactac
 181 gatccagatc tgaaagatgt gaacatagtt gcgacataca gtgaccatta cggcaatata
 241 cgccttggta gggtgaaaat gggggatctt tcaccttctt gggttttgga gaatcctgcc
 301 tatcaagtta gccgcaaaac aaaaggttcg cagctagtta taccacggga ttcatttcaa
 361 aatgatactg aatggaaga taatgcaagc cattctacaa ctaatcagac tgatgaaagc
 421 gaaaatcagt ttccaaacgt ggattttgca agcccagcaa aactgaagcg gcagatttta
 481 cgtcaggaaa ggagaggtca cgaactttta gagctgatcc gacaagaaaa ggaaactgat
 541 gagcagatgc aagaagcagc cattcagaag tcaatgagct ttgaaaaactc agtcataggg
 601 aaatacagta tatggaggag agactatgag agcccaaatg ctgatgctat cttgaagctt
 661 atgagagacc agatcataat ggcaaaagca tatgcaaata ttgccaaatc aaaaaatgta
 721 accaatctgt acgttttctt gatgcagcag tgtggagaaa ataaacgtgt tataggtaaa
 781 gcaacctctg atgctgacct tccttcaagc gctcttgatc aagcaaaagc catgggccat
 841 gcactctctc ttgcaaaaga cgagttatat gactgccatg aacttgcaaa aaagttccgg
 901 gccatccttc agtccactga acgcaaagta gatggactga gaaaaaaggg aaccttctta
 961 attcagctag ctgccaaaac atttcccaag ccattgcatt gcctgagtct gcagctagcg
1021 gcagactatt ttattctagg tttcaatgaa gaggatgcag tgaaagagga tgtcagtcaa
1081 aagaagcttg aagatccttc gctctatcac tatgcgatct tttcggataa cgttctggct
1141 acatcagtgg tggtgaactc cactgtcttg aatgcaaagg aaccgcagag gcatgtgttc
1201 catatagtaa ctgacaaaact gaattttggt gcaatgaaga tgtggtttcg catcaatgct
1261 cctgctgatg cgacgattca agttgaaaac ataaatgatt tcaagtggct gaactcctct
1321 tactgctctg ttctacggca gcttgaatct gcaaggctga agaatacta tttcaaagca
1381 aatcatcctt catcaatctc agctggcgca gataatctaa agtaccgcaa cccaaagtat
1441 ctatcgatgc tgaatcatct cagattctac cttcctgagg tttatccgaa gctggagaag
1501 attctgtttc tagacgatga cattgtggtg cagaaggacc tggcaccact atgggaaata
1561 gacatgcaag gaaaagtgaa tggtgcggtg gagacgtgca aggagagctt ccacagattt
1621 gacaagtacc tcaacttctc aaatccaaag atttcagaga atttttgacgc tggtgcttgt
1681 gggtgggcat ttgggatgaa tatgtttgac ctgaaagagt ggaggaaacg gaacattaca
1741 gggatatatc actattggca agacttgaat gaagacagaa cactgtggaa gctgggatcg
1801 ttgccaccgg ggctgataac attttacaac ctgacgtatg caatggatag gagctggcac
```

-continued

```
1861 gtactagggc tgggatatga cccagcgcta aaccaaacag caatagagaa tgcagcggta 1921 gtgcattaca atgggaacta caagccatgg ctgggtttag cattcgccaa gtacaaaccg 1981 tactggtcca agtacgttga gtacgacaac ccttatctcc gacggtgcga catcaatgaa 2041 tga
```

```
Amino Acid Sequence of Sequence #13: (SEQ ID NO: 26)
Genebank ID# NP_195540.2
Positions 1-680 of NP_195540.
    1 mttfstcaaf lslvvvlhav hvggailesq aphrelkayr plqdnnlqev yassaaavhy 61 dpdlkdvniv atysdhygni rlgrvkmgdl spswvlenpa yqvsrktkgs qlviprdsfq 121 ndtgmednas hsttnqtdes enqfpnvdfa spaklkrqil rqerrgqrtl elirqeketd 181 eqmqeaaiqk smsfensvig kysiwrrdye spnadailkl mrdqiimaka yaniaksknv 241 tnlyvflmqq cgenkrvigk atsdadlpss aldqakamgh alslakdely dchelakkfr 301 ailqsterkv dglkkkgtfl iqlaaktfpk plhclslqla adyfilgfne edavkedvsq 361 kkledpslyh yaifsdnvla tsvvvnstvl nakepqrhvf hivtdklnfg amkmwfrina 421 padatiqven indfkwlnss ycsvlrqles arlkeyyfka nhpssisaga dnlkyrnpky 481 lsmlnhirfy lpevypklek ilflddivv qkdlaplwei dmqgkvngav etckesfhrf 541 dkylnfsnpk isenfdagac gwafgmnmfd lkewrkrnit giyhywqdln edrtlwklgs 601 lppglitfyn ltyamdrswh vlgtgydpal nqtaienaav vhyngnykpw lglafakykp 661 ywskyveydn pylrrcdine
```

```
Sequence #14 (SEQ ID NO: 27)
Gene name: At5g15470
GeneBank accession # for reference: NM_121551 GI:30685368
Nucleotide sequence of Sequence #14:
Positions 1-1599 of CDS of NM_121551.
    1 atgcagcttc acatatcgcc gagtatgaga agcattacga tttcgagcag caatgagttt 61 attgacttga tgaagatcaa ggtcgcagct cgtcacatct cttaccgaac tctcttccac 121 accatcttaa tcctcgcttt cttgttgcct tttgttttca ttctcaccgc tgttgttacc 181 cttgagggtg tcaacaaatg ctcctccatt gattgtttag ggaggcggat aggtccacgt 241 cttcttggta gggtagatga ttcagagaga ctagctagag acttttataa aattctaaac 301 gaagtaagca ctcaagaaat tccagatggt ttgaagcttc caaattcttt tagtcaactt 361 gtttccgata tgaagaataa ccactatgat gcaaaaacat tgctcttgt gctgcgagcc 421 atgatggaga agtttgaacg tgatatgagg gaatcgaaat tgcagaact tatgaacaag 481 cactttgcag caagttccat tcccaaaggc attcattgtc tctctctaag actgacagat 541 gaatattcct ccaatgctca tgctcgaaga cagcttcctt caccagagtt tctccctgtt 601 ctttcagata tgcttacca ccactttatt tgtccacgg acaatatttt ggctgcctca 661 gttgtggtct catccgctgt tcagtcatct tcaaaacccg agaaaattgt ctttcacatc 721 attacagaca agaaaaccta tgcgggtatg cattcatggt ttgcgcttaa ttctgttgca 781 ccagcaattg ttgaggttaa aggtgttcat cagtttgact ggttgacgag agagaatgtt 841 ccggttttgg aagctgtgga aagccataat ggtgtcaggg actattatca tgggaatcat 901 gtcgctgggg caaacctcac cgaaacaact cctcgaacat tgcttcaaa attgcagtct 961 agaagtccaa aatacatatc tttgctcaac catcttagaa tatatatacc agagcttttc 1021 ccgaacttgg acaaggtggt tttcttagac gatgatatag ttgtccaggg agacttaact 1081 ccactttggg atgttgacct cggtggtaag gtcaatgggg cagtagagac ttgcaggggt 1141 gaagatgaat gggtgatgtc aaagcgttta aggaactact tcaatttctc tcacccgctc
```

-continued

```
1201 atcgcaaagc atttagatcc tgaagaatgt gcttgggcat atggtatgaa tatcttcgat 1261 ctacaagctt ggaggaaaac aaatatcaga gaaacgtatc actcttggct tagagagaat 1321 ctaaagtcaa atctgacaat gtggaaactt ggaaccttgc ctcctgctct tatcgcgttc 1381 aagggtcacg tacacataat agactcgtca tggcatatgc taggattagg ctaccagagc 1441 aagaccaaca tagaaaatgt gaagaaagca gcagtgatcc actacaatgg gcagtcaaag 1501 ccatggctgg agattggttt cgagcatctg cggccattct ggaccaaata cgtcaactac 1561 tcaaatgatt tcatcaagaa ctgtcacata ttggagtag
```

Amino Acid Sequence of Sequence #14: (SEQ ID NO: 28)
Genebank ID# NP_197051
Positions 1-532 of NP_197051.

```
   1 mqlhispsmr sitissssnef idlmkikvaa rhisyrtlfh tililaflip fvfiltavvt 61 legvnkcssi dclgrrigpr llgrvddser lardfykiln evstqeipdg lklpnsfsql 121 vsdmknnhyd akifalvira mmekferdmr eskfaelmnk hfaassipkg ihctslrltd 181 eyssnaharr qlpspeflpv lsdnayhhfi lstdnitaas vvvssavqss skpekivfhi 241 itdkktyagm hswfalnsva paivevkgvh qfdwltrenv pvleaveshn gvrdyyhgnh 301 vaganltett prtfasklqs rspkyislln hlriyipelf pnldkvvfld ddivvqgdlt 361 plwdvdlggk vngavetcrg edewvmskrl rnyfnfshpl iakhldpeec awaygmnifd 421 lqawrktnir etyhswlren lksnltmwkl gtlppaliaf kghvhiidss whmlglgyqs 481 ktnienvkka avihyngqsk pwleigfehl rpfwtkyvny sndfiknchi le
```

Sequence #15 (SEQ ID NO: 29)
Gene name: At5g54690
GeneBank accession # for reference: NM_124850 GI:30696504
Nucleotide sequence of Sequence #15:
Positions 1-1608 of CDS of NM_124850.

```
   1 atgcagttac atatatctcc gagcttgaga catgtgactg tggtcacagg gaaaggattg 61 agagagttca taaaagttaa ggttggttct agaagattct cttatcaaat ggtgttttac 121 tctctactct tcttcacttt tcttctccga ttcgtctttg ttctctccac cgttgatact 181 atcgacggcg atccctctcc ttgctcctct cttgcttgct ggggaaaag actaaagcca 241 aagcttttag gaagaagggt tgattctggt aatgttccag aagctatgta ccaagttta 301 gaacagcctt taagcgaaca agaactcaaa ggaagatcag atataccttca aacacttcaa 361 gatttcatgt ctgaagtcaa aagaagcaaa tcagacgcaa gagaatttgc tcaaaagcta 421 aaagaaatgg tgacattgat ggaacagaga acaagaacgg ctaagattca agagtattta 481 tatcgacatg tcgcatcaag cagcataccg aaacaacttc actgtttagc tcttaaacta 541 gccaacgaac actcgataaa cgcagcggcg cgtctccagc ttccagaagc tgagcttgtc 601 cctatgttgg tagacaacaa ctactttcac tttgtcttgg cttcagacaa tattcttgca 661 gcttcggttg tggctaagtc gttggttcaa aatgctttaa gacctcataa gatcgttctt 721 cacatcataa cggataggaa aacttatttc ccaatgcaag cttggttctc attgcatcct 781 ctgtctccag caataattga ggtcaaggct ttgcatcatt tcgattggtt atcgaaaggt 841 aaagtacccg ttttggaagc tatggagaaa gatcagagag tgaggtctca attcagaggt 901 ggatcatcgg ttattgtggc taataacaaa gagaacccgg ttgttgttgc tgctaagtta 961 caagctctca gccctaaata caactccttg atgaatcaca tccgtattca tctaccagag 1021 ttgtttccaa gcttaaacaa ggttgtgttt ctagacgatg acattgtgat ccaaactgat 1081 ctttcacctc tttgggacat tgacatgaat ggaaaagtaa atggagcagt ggaaacatgt 1141 agaggagaag acaagtttgt gatgtcaaag aagttcaaga gttacctcaa cttctcgaat
```

```
1201 ccgacaattg ccaaaaactt caatccagag gaatgtgcat gggcttatgg aatgaatgtt 1261 ttcgacctag cggcttggag gaggactaac ataagctcca cttactatca ttggcttgac 1321 gagaacttaa aatcagacct gagtttgtgg cagctgggaa ctttgcctcc tgggctgatt 1381 gctttccacg gtcatgtcca aaccatagat ccgttctggc atatgcttgg tctcggatac 1441 caagagacca cgagctatgc cgatgctgaa agtgccgctg ttgttcattt caatggaaga 1501 gctaagcctt ggctggatat agcatttcct catctacgtc ctctctgggc taagtatctt 1561 gattcttctg acagatttat caagagctgt cacattagag catcatga
```

Amino Acid Sequence of Sequence #15: (SEQ ID NO: 30)
Genebank ID# NP_200280
Positions 1-535 of NM_200280.

```
  1 mqlhispslr hvtvvtgkgl refikvkvgs rrfsyqmvfy sllfftfllr fvfvlstvdt 61 idgdpspcss laclgkrlkp kllgrrvdsg nvpeamyqvl eqplseqelk grsdipqtlq 121 dfmsevkrsk sdarefaqkl kemvtlmeqr trtakiqeyl yrhvasssip kqlhclalkl 181 anehsinaaa rlqlpeaelv pmlvdnnyfh fvlasdnita asvvakslvq nalrphkivl 241 hiitdrktyf pmqawfslhp lspaiievka lhhfdwlskg kvpvleamek dqrvrsqfrg 301 gssvivannk enpvvvaakl qalspkynsl mnhirihlpe lfpslnkvvf ldddiviqtd 361 lsplwdidmn gkvngavetc rgedkfvmsk kfksylnfsn ptiaknfnpe ecawaygmnv 421 fdlaawrrtn isstyyhwld enlksdlslw qlgtlppgli afhghvqtid pfwhmlglgy 481 qettsyadae saavvhfngr akpwldiafp hirpiwakyl dssdrfiksc hiras
```

The nucleotide and amino acid sequences of the ten GALAT-LIKE gene family members are shown as follows.
Sequence #16 (SEQ ID NO:31)
Gene name: At1g02720
GeneBank accession # for reference: NM_100152, GI: 30678358
Nucleotide sequence of Sequence #16:
Positions 1-1086 of CDS of NM_100152.

```
   1 atgcattgga ttacgagatt ctctgctttc ttctccgccg cattagccat gattctcctt 61 tctccttcgc tccaatcctt ttctccggcg gcagctatcc gatcatctca cccctacgcc 121 gacgaattca accccaaca aaactccgat tactcctcct tcagagaatc tccaatgttc 181 cgtaacgccg aacaatgcag atcttccggc gaagattccg gcgtctgtaa ccctaatctc 241 gtccacgtag ccatcactct cgacatcgat tacctccgtg gctcaatcgc agccgtcaat 301 tcgatcctcc agcactcaat gtgccctcaa agcgtcttct tccacttcct cgtctcctcc 361 gagtctcaaa acctagaatc tctgattcgt tctactttcc ccaaattgac gaatctcaaa 421 atttactatt ttgcccctga daccgtacag tcttttgattt catcttccgt gagacaagcc 481 ctagagcaac cgttgaatta cgccagaaat tacttggcgg atctgctcga gccttgcgtt 541 aagcgagtca tctacttgga ttcggatctc gtcgtcgtcg atgatatcgt caagctttgg 601 aaaacgggtt taggccagag aacaatcgga gctccggagt attgtcacgc gaatttcacg 661 aaatacttca ccggaggttt ttggtcagat aagaggttta acgggacgtt caaagggagg 721 aacccttgtt acttcaatac tggtgtaatg gtgattgatt tgaagaagtg gagacaattt 781 aggttcacga acgaattga gaatggatg gagattcaga agatagagag gatttatgag 841 cttggttctc ttcctccgtt tcttctggta tttgctggtc atgtagctcc gatttcacat 901 cggtggaatc aacatgggct tggtggtgat aatgttagag gtagttgccg tgatttgcat 961 tctggtcctg tgagtttgct tcactggtca ggtagtggta agccatggtt aagactcgat 1021 tccaagcttc catgtccttt agacacattg tgggcacctt atgatttgta taaacactcc 1081 cattga
```

-continued

Amino Acid Sequence of Sequence #16: (SEQ ID NO: 32)
Genebank ID# NP_171772
Positions 1-361.

```
  1 mhwitrfsaf fsaalamill spslqsfspa aairsshpya defkpqqnsd yssfrespmf 61 rnaeqcrssg edsgvcnpnl vhvaitldid ylrgsiaavn silqhsmcpq svffhflvss 121 esqnleslir stfpkltnlk iyyfapetvq slissvrqa leqplnyarn yladllepcv 181 krviyldsdl vvvddivklw ktglgqrtig apeychanft kyftggfwsd krfngtfkgr 241 npcyfntgvm vidlkkwrqf rttkriekwm eiqkieriye lgslppfllv faghvapish 301 rwnqhglggd nvrgscrdlh sgpvsllhws gsgkpwlrld sklpcpldtl wapydlykhs 361 h
```

Sequence #17 (SEQ ID NO:33)
Gene name: At1g13250
GeneBank accession # for reference: NM_101196, GI:30683194
Nucleotide sequence of Sequence #17:
Positions 1-1038 of CDS of NM_101196.

```
   1 atgtcttctc tgcgtttgcg tttatgtctt cttctactct tacctatcac aattagctgc 61 gtcacagtca ctctcactga cctccccgcg tttcgtgaag ctccggcgtt tcgaaacggc 121 agagaatgct ccaaaacgac atggataccc tcggatcacg aacacaaccc atcaatcatc 181 cacatcgcta tgactctcga cgcaatttac ctccgtggct cagtcgccgg cgtcttctcc 241 gttctccaac acgcttcttg tcctgaaaac atcgttttcc acttcatcgc cactcaccgt 301 cgcagcgccg atctccgccg cataatctcc tcaacattcc catacctaac ctaccacatt 361 taccattttg accctaacct cgtccgcagc aaaatatctt cctctattcg tcgtgcttta

421 gaccaaccgt taaactacgc tcggatctac ctcgccgatc tcctcccaat cgccgtccgc 481 cgcgtaatct acttcgactc cgatctcgta gtcgtcgatg acgtggctaa actctggaga 541 atcgatctac gtcggcacgt cgtcggagct ccggagtact gtcacgcgaa tttcactaac 601 tacttcactt caagattctg gtcgagtcaa ggttacaaat cggcgttgaa agataggaaa 661 ccgtgttatt tcaacaccgg agtgatggtg attgatctcg gaaatggag agaaaggaga 721 gtcacggtga agctagagac atggatgagg attcaaaaac gacatcgtat ttacgaattg 781 ggatctttgc ctccgtttct gctcgttttc gccggagatg ttgagccggt ggagcatagg 841 tggaatcagc atggtcttgg tggtgataac ttggaaggac tttgccggaa tttgcatcca 901 ggtccggtga gtttgttgca ttggagcggg aaagggaaac catggctaag gcttgactcg 961 agacgaccgt gtccgttgga ttcgttatgg gctccttatg atttgtttcg ttattcaccg 1021 ttgatctctg atagctga
```

Amino Acid Sequence of Sequence #17: (SEQ ID NO: 34)
Genebank ID# NP_563925
Positions 1-345.

```
  1 msslrlrlcl llllpitisc vtvtltdlpa freapafrng recskttwip sdhehnpsii 61 hiamtldaiy lrgsvagvfs vlqhascpen ivfhfiathr rsadlrriis stfpyltyhi 121 yhfdpnlvrs kisssirral dqplnyariy ladllpiavr rviyfdsdlv vvddvaklwr 181 idlrrhvvga peychanftn yftsrfwssq gyksalkdrk pcyfntgvmv idlgkwrerr 241 vtvkletwmr iqkrhriyel gslppfllvf agdvepvehr wnqhglggdn leglcrnlhp 301 gpvsllhwsg kgkpwlrlds rrpcpldslw apydlfrysp lisds
```

Sequence#18 (SEQ ID NO:35)
Gene name: At1g19300
GeneBank accession # for reference: NM_101787, GI:30686302
Nucleotide sequence of Sequence #18:
Positions 1-1056 of CDS of NM_101787.

```
   1 atgtcccaac atcttcttct tctcattctc ctctcgctac ttcttcttca taaacccatt
```

-continued

```
  61 tccgccacta caattattca aaaattcaaa gaagccccac agttttacaa ttctgcagat 121 tgcccttaa tcgatgactc cgagtccgac gatgacgtgg tcgccaaacc aatcttctgc 181 tcacgtcgag ctgtccacgt ggcgatgaca ctcgacgccg cctacattcg tggctcagtc 241 gccgctgttc tctccgtcct ccaacactct tcttgtcctg aaaacattgt tttccacttc 301 gtcgcctctg cttccgccga cgcttcttcc ttacgagcca ccatatcctc ctctttccct 361 taccttgatt tcaccgtcta cgtcttcaac gtctcctccg tctctcgcct tatctcctcc 421 tctatccgct ccgcactaga ctgtccttta aactacgcaa gaagctacct cgccgatctc 481 ctccctccct gcgtccgccg cgtcgtctac ctagactccg atctgatcct cgtcgacgac 541 atagcaaaac tcgccgccac agatctcggc cgtgattcag tcctcgccgc gccggaatac 601 tgcaacgcca atttcacttc atacttcaca tcaaccttct ggtctaatcc gactctctct 661 ttaaccttcg ccgatcggaa agcatgctac ttcaacactg gagtcatggt gatcgatctt 721 tcccggtggc gcgaaggcgc gtacacgtca cgcatcgaag agtggatggc gatgcaaaag 781 agaatgagaa tttacgagct tggttcgtta ccaccgtttt tattggtttt tgccggtttg 841 attaaaccgg ttaatcatcg gtggaaccaa cacggtttag gaggtgataa tttcagagga 901 ctgtgtagag atctccatcc tggtccggtg agtctgttgc attggagtgg aaaggtaag 961 ccatgggcta ggcttgatgc tggtcggcct tgtcctttag acgcgctttg ggctccgtat 1021 gatcttcttc aaacgccgtt cgcgttggat tcttga
```

Amino Acid Sequence of Sequence #18: (SEQ ID NO: 36)
Genebank ID# NP_564077
Positions 1-351.

```
   1 msqhllllil lsllllhkpi sattiiqkfk eapqfynsad cpliddsesd ddvvakpifc 61 srravhvamt ldaayirgsv aavlsvlqhs scpenivfhf vasasadass lratissfp 121 yldftvyvfn vssvsrliss sirsaldcpl nyarsyladi lppcvrrvvy ldsdlilvdd 181 iaklaatdlg rdsvlaapey cnanftsyft stfwsnptls ltfadrkacy fntgvmvidl 241 srwregayts rieewmamqk rmriyelgsl ppfllvfagl ikpvnhrwnq hglggdnfrg 301 lcrdlhpgpv sllhwsgkgk pwarldagrp cpldalwapy dllqtpfald s
```

Sequence #19 (SEQ ID NO:37)
Gene name: At1g24170
GeneBank accession # for reference: NM_102263, GI:30688765
Nucleotide sequence of Sequence #19:
Positions 1-1182 of CDS of NM_102263.

```
   1 atgtcgtcgc gttttctttt gacggtggtg tgtttgattg ctctgttacc gtttgttgtt 61 ggtatacggt tgattccggc gaggatcacg agtgtcggtg atggcggcgg cggaggaggt 121 aataatgggt ttagtaaact tggtccgttt atggaagctc cggagtatag aaacggcaag 181 gagtgtgtat cttcatcagt gaacagagag aacttcgtgt cgtcttcttc tagttctaat 241 gatccttcgc ttgttcacat cgctatgact ttggactcag agtatctccg tggatcaatc 301 gcagccgttc attctgttct tcgccacgcg tcttgtccag agaacgtctt cttccatttc 361 atcgctgctg agtttgactc tgcgagtcct cgtgttctga gtcaactcgt gaggtcgact 421 tttccttcgt tgaactttaa agtctacatt tttaggggag atacggtgat caatctcata 481 tcttcttcga ttagactagc tttggagaat ccgttgaact atgctcggaa ctatctcgga 541 gatattcttg atcgaagtgt tgaacgagtc atttatcttg actcggatgt tataactgtg 601 gatgatatca caaagctttg gaacacggtt ttgacccgggt cacgagtcat cggagctccg 661 gagtattgtc acgcgaactt cactcagtat ttcacttccg ggttctggtc agacccggct 721 ttaccgggtc taatctcggg tcaaaagcct tgctatttca acacaggagt gatggtgatg
```

-continued

```
 781 gatcttgtta gatggagaga agggaattac agagagaagt tagagcaatg gatgcaattg 841 cagaagaaga tgagaatcta cgatcttgga tcattaccac cgtttctttt ggtgtttgcg 901 ggtaatgttg aagctattga tcatagatgg aaccaacatg gtttaggagg agacaatata 961 cgaggaagtt gtcggtcatt gcatcctggt cctgtgagct tgttgcattg gagtggtaaa 1021 ggtaagccat gggttagact tgatgagaag aggccttgtc cgttggatca tctttgggag 1081 ccatatgatt tgtataagca taagattgag agagctaaag atcagtctct gcttgggttt 1141 gcttctctgt cggagttgac tgatgattca agcttcttgt ga
```

Amino Acid Sequence of Sequence #19: (SEQ ID NO: 38)
Genebank ID# NP_173827
Positions 1-393.

```
   1 mssrfsltvv cliallpfvv girliparit svgdgggggg nngfsklgpf meapeyrngk 61 ecvsssvnre nfvsssssssn dpslvhiamt ldseylrgsi aavhsvlrha scpenvffhf 121 iaaefdsasp rvlsqlvrst fpslnfkvyi fredtvinli sssirlalen pinyarnyig 181 dildrsverv iyldsdvitv dditklwntv ltgsrvigap eychanftqy ftsgfwsdpa 241 lpglisgqkp cyfntgvmvm dlvrwregny rekleqwmql qkkmriydlg slppfllvfa 301 gnveaidhrw nqhglggdni rgscrslhpg pvsllhwsgk gkpwvrldek rpcpldhlwe 361 pydlykhkie rakdqsllgf aslseltdds sfl
```

Sequence #20 (SEQ ID NO:39)
Gene name: At1g70090
GeneBank accession # for reference: NM_105677, GI:30697975
Nucleotide sequence of Sequence #20:
Positions 1-1173 of CDS of NM_105677.

```
   1 atgcggttgc gttttccgat gaaatctgcc gttttagcgt tgctatctt tctggtgttt 61 attccactgt tttccgtcgg tatacggatg attccgggaa gactcaccgc cgtatccgcc 121 accgtcggaa atggctttga tctggggtcg ttcgtggaag ctccggagta cagaaacggc 181 aaggagtgcg tgtctcaatc gttgaacaga gaaaacttcg tgtcgtcttg cgacgcttcg 241 ttagttcatg tagctatgac gcttgactcg gagtacttac gtggctcaat cgcagccgta 301 cattcaatgc tccgccacgc gtcgtgtcca gaaaacgtct tcttccatct catcgctgca 361 gagtttgacc cggcgagtcc acgcgttctg agtcaactcg tccgatctac tttcccgtcg 421 ctaaacttca agtctacat tttccgggaa gatacggtga tcaaccttat ctcttcttca 481 atcagacaag ctttagagaa tccattgaac tatgctcgga actacctcgg agatattctt 541 gatccatgcg tagacagagt catttaccta gactcggaca tcatcgtcgt cgatgacata 601 acaaagcttt ggaacacgag tttgacaggg tcaagaatca tcggagctcc ggagtattgt 661 cacgctaact tcacaaagta cttcacttca ggtttctggt ccgacccggc tttacccggt 721 ttcttctcgg gtcgaaagcc ttgttatttc aacacgggtg tgatggtgat ggatctagtt 781 agatggagag aaggaaacta cagagaaaag cttgaaactt ggatgcagat acagaagaag 841 aagagaatct cgatttggg ttctttgcct ccgtttcttc ttgtcttcgc agggaacgtt 901 gaagcaattg atcataggtg gaaccaacat ggtttaggag agacaatgt cgaggaagt 961 tgtaggtctt tgcataaagg accagtgagt tgttgcattg gagtggtaa aggtaagcca 1021 tgggtgagac ttgatgagaa gagaccgtgt ccgttggatc atttatggga accgtatgat 1081 ttatatgagc ataagattga aagagctaaa gatcagtctt gttcgggtt ctcttctttg 1141 tctgagttaa cagaagattc aagcttttc tga
```

Amino Acid Sequence of Sequence #20: (SEQ ID NO: 40)
Genebank ID# NP_564983
Positions 1-390.

```
   1 mrlrfpmksa vlafaiflvf iplfsvgirm ipgrltavsa tvgngfdlgs fveapeyrng
```

```
 61 kecvsqslnr enfvsscdas lvhvamtlds eylrgsiaav hsmlrhascp envffhliaa 121 efdpasprvl sqlvrstfps lnfkvyifre dtvinlisss irqalenpln yarnylgdil 181 dpcvdrviyl dsdiivvddi tklwntsltg sriigapeyc hanftkyfts gfwsdpalpg 241 ffsgrkpcyf ntgvmvmdlv rwregnyrek letwmqiqkk kriydlgslp pflllvfagnv 301 eaidhrwnqh glggdnvrgs crslhkgpvs llhwsgkgkp wvrldekrpc pidhiwepyd 361 lyehkierak dqslfgfssl seltedssff
```

Sequence #21 (SEQ ID NO:41)
Gene name: At3g06260
GeneBank accession # for reference: NM_111501, GI: 18397517
Nucleotide sequence of Sequence #21:
Positions 1-1056 of CDS of NM_111501.

```
   1 atggcctcaa ggagcctctc ctatacacaa ctcctaggcc tcctgtcctt tatactcctc 61 ttggtcacaa ccaccactat ggcggttcgt gttggagtca ttcttcataa gccttctgct 121 ccaactcttc ctgttttcag agaagccccg gcttttcgaa acggtgatca atgcgggact 181 cgtgaggctg atcagattca tatcgccatg actctcgaca caaactacct ccgtggcaca 241 atggctgccg ttttgtctct ccttcaacat tccacttgcc ctgaaaacct ctcttttcat 301 ttcctgtccc ttcctcattt cgaaaacgac cttttcacca gcatcaaatc aacctttcct 361 tacctaaaact tcaagattta tcagtttgat ccaaacctcg tccgcagcaa gatatcgaaa 421 tccatcaggc aagcccttga tcagcctctt aactacgcaa gaatctaccct cgcggatatc 481 atccctagca gcgttgacag gatcatctac ttagactcag acctcgttgt ggtagacgac 541 atagagaagc tgtggcatgt ggagatggaa ggtaaagtgg tggctgctcc cgagtactgc 601 cacgcaaact tcacccatta tttcacaaga actttctggt cagacccggt attggtcaaa 661 gttcttgaag gaaaacgtcc gtgttatttc aacacagggg tgatggttgt ggatgtaaac 721 aaatggagga aggaatgta tacacagaag gtagaagagt ggatgacaat tcagaagcag 781 aagaggatat accatttggg atcattacct ccgtttctgc tgatattcgc cggtgatata 841 aaagcggtta atcataggtg gaaccagcat ggtctaggag gtgataattt cgaaggaaga 901 tgtagaacgt tgcatccggg accgataagt cttcttcact ggagtggaaa agggaagcca 961 tggttaagac tagattcaag gaagccttgt atcgttgatc atctatgggc accgtatgat 1021 ctgtaccgtt catcaagaca ttcattagaa gagtag
```

Amino Acid Sequence of Sequence #21: (SEQ ID NO: 42)
Genebank ID# NP_187277
Positions 1-351.

```
   1 masrslsytq liglisfill lvttttmavr vgvilhkpsa ptlpvfreap afrngdqcgt 61 readqihiam tldtnylrgt maavlsllqh stcpenlsfh flslphfend lftsikstfp 121 ylnfkiyqfd pnlvrskisk sirqaldqpl nyariyladi ipssvdriiy ldsdlvvvdd 181 ieklwhveme gkvvaapeyc hanfthyftr tfwsdpvlvk vlegkrpcyf ntgvmvvdvn 241 kwrkgmytqk veewmtiqkq kriyhlgslp pflhifagdi kavnhrwnqh glggdnfegr 301 crtlhpgpis llhwsgkgkp wlrldsrkpc ivdhlwapyd lyrssrhsle e
```

Sequence #22 (SEQ ID NO:43)
Gene name: At3g28340
GeneBank accession # for reference: NM_113753, GI:30689155
Nucleotide sequence of Sequence #22:
Positions 1-1098 of CDS of NM_113753.

```
   1 atgatgtctg gttcaagatt agcctctaga ctaataataa tcttctcaat aatctccaca 61 tctttcttca ccgttgaatc gattcgacta ttccctgatt cattcgacga tgcatcttca 121 gatttaatgg aagctccagc atatcaaaac ggtcttgatt gctctgtttt agccaaaaac
```

-continued

```
 181 agactcttgt tagcttgtga tccatcagct gttcatatag ctatgactct agatccagct 241 tacttgcgtg gcacggtatc tgcagtacat tccatcctca aacacacttc ttgccctgaa 301 aacatcttct tccacttcat tgcttcgggt acaagtcagg gttccctcgc caagacccta 361 tcctctgttt ttccttcttt gagtttcaaa gtctatacct ttgaagaaac cacggtcaag 421 aatctaatct cttcttctat aagacaagct cttgatagtc ctttgaatta cgcaagaagc 481 tacttatccg agattctttc ttcgtgtgtt agtcgagtga tttatctcga ttcggatgtg 541 attgtggtcg atgatattca gaaactatgg aagatttctt tatccgggtc aagaacaatc 601 ggtgcaccag tattgccca cgcaaatttc accaaatact tcacagatag tttctggtcc 661 gatcaaaaac tctcgagtgt cttcgattcc aagactcctt gttatttcaa cacaggagtg 721 atggttatcg atttagagcg atggagagaa ggagattaca cgagaaagat cgaaaactgg 781 atgaagattc agaaagaaga taagagaatc tacgaattgg gttctttacc accgtttctt 841 ctagtgtttg gtggtgatat tgaagctatt gatcatcaat ggaaccaaca cggtctcggt 901 ggagacaaca ttgtgagtag ttgtagatct ttgcatcctg gtccggttag tttgatacat 961 tggagtggta aagggaagcc atgggttagg cttgatgatg gtaagccttg tccaattgat 1021 tatctttggg ctccttatga tcttcacaag tcacagaggc agtatcttca atacaatcaa 1081 gagttagaaa ttctttga
```

Amino Acid Sequence of Sequence #22: (SEQ ID NO: 44)
Genebank ID# NP_189474
Positions 1-365.

```
   1 mmsgsrlasr liiifsiist sfftvesirl fpdsfddass dlmeapayqn gldcsvlakn 61 rlllacdpsa vhiamtldpa ylrgtvsavh silkhtscpe niffhfiasg tsqgslaktl 121 ssvfpslsfk vytfeettvk nlisssirqa ldsplnyars ylseilsscv srviyldsdv 181 ivvddiqklw kislsgsrti gapeychanf tkyftdsfws dqklssvfds ktpcyfntgv 241 mvidlerwre gdytrkienw mkiqkedkri yelgslppfl lvfggdieai dhqwnqhglg 301 gdnivsscrs lhpgpvslih wsgkgkpwvr lddgkpcpid ylwapydlhk sqrqylqynq 361 eleil
```

Sequence #23 (SEQ ID NO:45)
Gene name: At3g50760
GeneBank accession # for reference: NM_114936, GI:18409176
Nucleotide sequence of Sequence #23:
Positions 1-1026 of CDS of NM_114936.

```
   1 atgcactcga agtttatatt atatctcagc atcctcgccg tattcaccgt ctctttcgcc 61 ggcggcgaga gattcaaaga agctccaaag ttcttcaact ccccggagtg tctaaccatc 121 gaaaacgatg aagatttcgt ttgttcagac aaagccatcc acgtggcaat gaccttagac 181 acagcttacc tccgtggctc aatggccgtg attctctccg cctccaaca ctcttcttgt 241 cctcaaaaca ttgttttcca cttcgtcact tcaaaacaaa gccaccgact ccaaaactac 301 gtcgttgctt cttttcccta cttgaaattc gaatttacc cttacgacgt agccgccatc 361 tccggcctca tctcaacctc catccgctcc gcgctagact ctccgctaaa ctacgcaaga 421 aactacctcg ccgacattct tcccacgtgc ctctcacgtg tcgtataccl agactcagat 481 ctcatactcg tcgatgacat ctccaagctc ttctccactc acatccctac cgacgtcgtt 541 ttagccgcgc tgagtactg caacgcaaac ttcacgactt actttactcc gacgttttgg 601 tcaaaccctt ctctctccat cacactatcc ctcaaccgcc gtgctacacc gtgttacttc 661 aacaccggag tgatggtcat cgagttaaag aaatggcgag aaggagatta cacgaggaag 721 atcatagagt ggatggagtt acaaaaacgg ataagaatct acgagttagg ctcttttacca
```

-continued

```
 781 ccgtttttac ttgtcttcgc cggaaacata gctccggtag atcaccggtg gaaccaacac 841 ggtttaggag gagataattt tagaggactg tgtcgagatt tgcatccagg tccagtgagt 901 ttgttgcatt ggagtgggaa agggaagcca tgggtaaggt tagatgatgg tcgaccttgc 961 ccgcttgatg cactttgggt tccatatgat ttgttagagt cacggttcga ccttatcgag 1021 agttaa
```

Amino Acid Sequence of Sequence #23: (SEQ ID NO: 46)
Genebank ID# NP_190645
Positions 1-341.

```
   1 mhskfilyls ilavftvsfa ggerfkeapk ffnspeclti endedfvcsd kaihvamtld 61 taylrgsmav ilsvlqhssc pqnivfhfvt skqshrlqny vvasfpylkf riypydvaai 121 sglistsirs aldsptnyar nyladilptc lsrvvyldsd lilvddiskl fsthiptdvv 181 laapeycnan fttyftptfw snpstsitls lnrratpcyf ntgvmvielk kwregdytrk 241 iiewmelqkr iriyelgslp pfllvfagni apvdhrwnqh glggdnfrgl crdlhpgpvs 301 llhwsgkgkp wvrlddgrpc pldalwvpyd llesrfdlie s
```

Sequence #24 (SEQ ID NO:47)
Gene name: At3g62660
GeneBank accession # for reference: NM_116131, GI:30695642
Nucleotide sequence of Sequence #24:
Positions 1-1086 of CDS of NM_116131.

```
   1 atgctttgga tcatgagatt ctccggttta ttctccgccg cttttggttat catcgtcctc 61 tctccttctc tccaatcgtt tcctccagct gaagctatca gatcctctca tctcgacgct 121 tacctccgtt tcccctcctc cgatccaccg ccgcatagat tctccttcag aaaagctcct 181 gttttccgca atgccgccga ttgcgccgcc gcagatatcg attccggcgt ctgtaaccct 241 tccttggtcc acgtcgcgat tactctcgat ttcgagtacc tgcgtggctc aatcgccgcc 301 gttcattcga ttctcaagca ctcgtcgtgt cccgagagcg tcttcttcca tttcctcgtc 361 tccgagactg acctagaatc cttgattcgt tcgactttc ccgaattgaa attaaaggtt 421 tactacttcg atccggagat tgtacggacg ctgatctcaa cctccgtgag acaagcgctc 481 gagcagccgt tgaattacgc tagaaattac ctagctgacc ttctcgagcc ttgcgtgcgt 541 cgcgtgatct acctagattc cgatctaatc gtcgtcgacg acatcgcaaa gctctggatg 601 acgaaactgg gatcgaaaac gatcggagct cccgagtact gtcacgcgaa cttcacaaag 661 tatttcacac cggcgttctg gtccgacgag aggttctccg gagctttctc cgggaggaaa 721 ccgtgctact tcaacacggg agtgatggtg atggatctag agagatggag gcgcgtaggg 781 tacacggagg tgatagagaa atggatggag attcagaaga gtgataggat ttacgagctg 841 ggatcattgc cgccgttctt gttggtgttc gccggagaag tagctccgat agagcatcgg 901 tggaaccagc atgggcttgg tggagataac gtgagaggaa gctgtagaga tttacatccc 961 ggtccggtta gcttgcttca ttggtccggt agtggtaaac cgtggtttcg gttagattcg 1021 agacggcctt gtccacttga tactctttgg gcaccttatg atttgtatgg acactactct 1081 cgctga
```

Amino Acid Sequence of Sequence #24: (SEQ ID NO: 48)
Genebank ID# NP_191825
Positions 1-361.

```
   1 mlwimrfsgl fsaalviivl spslqsfppa eairsshlda ylrfpssdpp phrfsfrkap 61 vfrnaadcaa adidsgvcnp slvhvaitld feylrgsiaa vhsilkhssc pesvffhflv 121 setdleslir stfpelklkv yyfdpeivrt listsvrqal eqplnyarny ladllepcvr 181 rviyldsdli vvddiaklwm tklgsktiga peychanftk yftpafwsde rfsgafsgrk 241 pcyfntgvmv mdlerwrrvg yteviekwme iqksdriyel gslppfllvf agevapiehr
```

-continued

```
 301 wnqhglggdn vrgscrdlhp gpvsllhwsg sgkpwfrlds rrpcpldtlw apydlyghys 361 r
```

Sequence #25 (SEQ ID NO:49)
Gene name: At4g02130
GeneBank accession # for reference: NM_116445, GI:18411845
Nucleotide sequence of Sequence #25:
Positions 1-1041 of CDS of NM_116445.

```
    1 atgctttgga taacgagatt tgctggatta ttctccgccg cgatggcagt gatcgtgtta 61 tctccgtcgc ttcagtcatt tcctccggcg gcggcaatcc gttcttctcc atcaccgatc 121 ttcagaaaag ctccagcggt gttcaacaac ggcgacgaat gtctctcctc cggcggcgtc 181 tgcaatccgt cgttggtcca cgtggcgatc acgttagacg tagagtacct gcgtggctca 241 atcgcagccg ttaactcgat ccttcagcac tcggtgtgtc cagagagcgt cttcttccac 301 ttcatcgccg tctccgagga aacaaacctg ttggagtcgc tggtgagatc ggttttcccg 361 agactgaaat tcaatattta cgattttgcc cctgagacag ttcgtggttt gatttcttct 421 tccgtgagac aagctctcga gcagcctctg aactacgcta gaagctactt agcggatctg 481 ctggagcctt gtgttaaccg tgtcatatac ttggattcgg atcttgtcgt cgtcgatgac 541 atcgctaagc tttggaaaac tagcctaggc tcgaggataa tcggagctcc ggagtattgt 601 cacgcgaatt tcacgaaata cttcaccgga ggattctggt cggaggagag attctccggt 661 acctttagag ggaggaagcc atgttacttc aacacaggtg tgatggtgat agatcttaag 721 aaatggagaa gaggtggtta cacgaaacgt atcgagaaat ggatggagat tcagagaaga 781 gagaggattt acgaactagg ctcgcttcca ccgtttcttc tagttttctc cggtcacgtg 841 gctcccatct ctcaccggtg gaaccagcat ggacttggtg gtgacaatgt tagaggtagc 901 tgtcgtgatt tgcatcctgg tcctgtgagt ttgctgcatt ggtctggtag tggcaagccc 961 tggataagac tcgattccaa acggccttgt cccttagacg cattatggac gccttacgac 1021 ttgtatcgac attcgcattg a
```

Amino Acid Sequence of Sequence #25: (SEQ ID NO: 50)
Genebank ID# NP_192122
Positions 1-346.

```
    1 mlwitrfagl fsaamavivl spslqsfppa aairsspspi frkapavfnn gdeclssggv 61 cnpslvhvai tldveylrgs iaavnsitqh svcpesvffh fiavseetnl leslvrsvfp 121 rlkfniydfa petvrgliss svrqaleqpl nyarsyladi lepcvnrviy ldsdlvvvdd 181 iaktwktslg sriigapeyc hanftkyftg gfwseeifsg tfrgrkpcyf ntgvmvidlk 241 kwrrggytkr iekwmeiqrr eriyelgslp pfllvfsghv apishrwnqh glggdnvrgs 301 crdlhpgpvs llhwsgsgkp wirldskrpc pldalwtpyd lyrhsh
```

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from the plant, or from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

As used herein expression directed by a particular sequence is the transcription of an associated downstream sequence. If appropriate and desired for the associated sequence, there the term expression also encompasses translation (protein synthesis) of the transcribed RNA. When expression of a sequence of interest is "up-regulated," the expression is increased. With reference to up-regulation of expression of a sequence of interest operably linked to a transcription regulatory sequence, expression is increased.

In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer molecule is present in the medium in or on which the organism is cultivated. In the present context, a transcription regulatory sequence includes a promoter sequence and can further include cis-active sequences for regulated expression of an associated sequence in response to environmental signals.

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a polynucleotide which is substantially separated from other polynucleotide sequences which naturally accompany a native transcription regulatory sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other sequences, for example, those from other species or other strains. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell. Usually the construct is suitable for replication in a unicellular host, such as *A. pullulans* or a bacterium, but a multicellular eukaryotic host may also be appropriate, with or without integration within the genome of the host cell. Commonly used prokaryotic hosts include strains of *Escherichia coli,* although other prokaryotes, such as *Bacillus subtilis* or a pseudomonad, may also be used. Eukaryotic host cells include yeast, filamentous fungi, plant, insect, amphibian, mammalian and avian species. Such factors as ease of manipulation, ability to appropriately glycosylate expressed proteins, degree and control of protein expression, ease of purification of expressed proteins away from cellular contaminants or other factors influence the choice of the host cell.

The polynucleotides may also be produced by chemical synthesis, e.g., by the phosphoramidite method described by Beaucage and Caruthers (1981) *Tetra. Letts.,* 22: 1859-1862 or the triester method according to Matteuci et al. (1981) *J. Am. Chem. Soc.,* 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1995) *Current Protocols in Molecular Biology,* Greene Publishing and Wiley Interscience, New York; and Metzger et al. (1988) *Nature,* 334: 31-36. Many useful vectors for expression in bacteria, yeast, fungal, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art which is appropriate for the particular type of cell, including without limitation, transformation, lipofection or electroporation.

It is recognized by those skilled in the art that the DNA sequences may vary due to the degeneracy of the genetic code and codon usage. All DNA sequences which code for the polypeptide or protein of interest are included in this invention.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that the sequence of the exemplified sequence can be used to identify and isolate additional, nonexemplified nucleotide sequences which are functionally equivalent to the sequences given.

Mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant polynucleotide to function in the same capacity as the polynucleotide from which the probe was derived. Preferably, this homology is greater than 80%, more preferably, this homology is greater than 85%, even more preferably this homology is greater than 90%, and most preferably, this homology is greater than 95%. The degree of homology or identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage.

Polymerase Chain Reaction (PCR) is a repetitive, enzymatic, primed synthesis of a nucleic acid sequence. This procedure is well known and commonly used by those skilled in this art [see Mullis, U.S. Pat. Nos. 4,683,195, 4,683,202, and 4,800,159; Saiki et al. (1985) *Science* 230:1350-1354]. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus,* the amplification process can be completely automated. Other enzymes which can be used are known to those skilled in the art.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Bal31 exonuclease can be conveniently used for time-controlled limited digestion of DNA. See, for example, Maniatis (1982) *Molecular Cloning: A Laboratory Manual,* Cold Spring Harbor Laboratory, New York, pages 135-139, incorporated herein by reference. See also Wei et al. (1983 *J. Biol. Chem.* 258:13006-13512. By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original molecule. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3): 349-59; Shortle, D, DiMaio, D., and Nathans, D. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain promoter activity and also provide transcription of downstream sequence.

Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) *Nucl. Acids. Res.* 25:3389-3402. When utilizing BLAST and Gapped BLAST programs, the default parameters of the respective programs (NBLAST and XBLAST) are used. See, for example, the National Center for Biotechnology Information website on the internet.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., Methods for Plant Molecular Biology, A. Weissbach and H. Weissbach, eds., Academic Press, Inc., San Diego, Calif. (1988).

Techniques for genetically engineering plant cells and/or tissue with an expression cassette comprising an inducible promoter or chimeric promoter fused to a heterologous coding sequence, including possibly an antisense DNA construct and/or a DNA construct designed to elicit double-stranded RNA-mediated gene silencing, followed by a transcription termination sequence are to be introduced into the plant cell or tissue by *Agrobactedium*-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art. Suitable plant transformation vectors include those derived from a Ti plasmid of *Agrobactedum tumefaciens*, such as those disclosed by Herrera-Estrella (1983), Bevan (1983), Klee (1985) and EPO publication 120,516 (Schilperoort et al.). In addition to plant transformation vectors derived from the Ti or root-inducing (Ri) plasmids of *Agrobactedum*, alternative methods can be used to insert the DNA constructs of this invention into plant cells.

The choice of vector in which the DNA of interest is operatively linked depends directly, as is well known in the art, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells.

Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in Molecular Cloning: A Laboratory Manual, Second Edition, Maniatis et al., eds., Cold Spring Harbor Press (1989) and the Lambda ZAP vectors available from Stratagene (La Jolla, Calif.). Other exemplary vectors include pCMU [Nilsson et al. (1989) *Cell* 58:707]. Other appropriate vectors may also be synthesized, according to known methods; for example, vectors pCMU/Kb and pCMUII used in various applications herein are modifications of pCMUIV [Nilsson, (1989) supra].

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) *Meth. in Enzymol.* 153:253-277, and several other expression vector systems known to function in plants. See for example, Verma et al., No. WO87/00551; Cocking and Davey (1987) *Science* 236:1259-1262.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment [See Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Science* 244:1293; Leemans (1993) *Bio/Technology* 11:522; Beck et al. (1993) *Bio/Technology* 11:1524; Koziel et al. (1993) *Bio/Technology* 11:194; Vasil et al. (1993) *Bio/Technology* 11:1533 and Gelvin, S. B. (1999) *Curr. Opin. Biotech.* 9:227-232]. Techniques are well-known to the art for the introduction of DNA into monocots as well as dicots, as are the techniques for culturing such plant tissues and regenerating those tissues.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth.*

*Enzymol.* 65; Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; Setlow and Hollaender (1979) *Genetic Engineering: Principles and Methods,* Vols. 1-4, Plenum Press, New York; and Ausubel et al. (1992) *Current Protocols in Molecular Biology,* Greene/Wiley, New York, N.Y. Abbreviations and nomenclature, where employed, are deemed standard in the field and commonly used in professional journals such as those cited herein.

All references cited in the present application are incorporated in their entirety herein by reference to the extent not inconsistent herewith.

REFERENCES

1. Liljebjelke, K. et al., Enzymatic synthesis and purification of uridine diphosphate [$^{14}$C]galacturonic acid: a substrate for pectin biosynthesis, *Anal. Biochem.* 225:296-304 (1995).
2. Doong, R. L. et al., Cell free synthesis of pectin: identification and partial characterization of polygalacturonate 4-alpha-galacturonosyltransferase and its products from membrane preparations of tobacco (*Nicotiana tabacum* L. cv samsun) cell suspension cultures, *Plant Physiol.* 109: 141-152 (1995).
3. Doong, R. L. et al. Solubilization and characterization of a galacturonosyltransferase that synthesizes the pectic polysaccharide homogalacturonan, *The Plant Journal* 13:363-374 (1998).
4. Scheller, H. V. et at, Pectin biosynthesis: a solubilized galacturonosyltransferase from tobacco catalyzes the transfer of galacturonic acid from UDP-galacturonic acid onto the non-reducing end of homogalacturonan, Planta 207:512-517 (1 999).
5. Mohnen, D. et al., A multi-enzyme approach to study pectin biosynthesis, *Annual Meeting of the American Society of Plant Physiology,* July 24-July 28 Abst. No. 203:65 (1999).(Abstract)
6. Mohnen, D., Biosynthesis of pectins and galactomannans, in: "Comprehensive Natural Products Chemistry, Vol. 3, Carbohydrates and Their Derivatives including Tannins, Cellulose, and Related Lignins", B. M. Pinto., ed., Elsevier, Oxford, pp. 497-527 (1999).
7. Sterling, J. et al., The catalytic site of the pectin biosynthetic enzyme alpha-1,4-galacturonosyltransferase (GalAT) is located in the lumen of the Golgi, *Plant Physiol.* 127:360-371 (2001).
8. Ridley, B. L. et al., Pectins: structure, biosynthesis, and oligogalacturonide-related signaling, *Phytochemistry* 57:929-967 (2001).
9. Mohnen, D., Biosynthesis of pectins, in: "Pectins and their Manipulation", G. B.

Seymour et al., Blackwell Publishing and CRC Press, Oxford, pp. 52-98 (2002).
10. Villemez, C. L. et al., Properties of a polygalacturonic acid-synthesizing enzyme system from *Phaseolus aureus* seedlings. *Arch. Biochem. Biophys.* 116:446-452 (1966).
11. Kauss, H. et al., Cooperation of enzymes responsible for polymerization and methylation in pectin biosynthesis. *Z. Naturforsch.* 24:28-33 (1969).
12. Lin, T.-Y. et al., Substrate specificity in pectin synthesis. *Biochem. Biophys.*
Res. Commun. 22:650-657 (1966).
13. Bolwell, G. P. et al., Decrease of polygalacturonic acid synthase during xylem differentiation in sycamore. *Phytochemistry* 24:699-702 (1985).
14. Takeuchi, Y. et al., In vitro biosynthesis of homogalacturonan by a membrane-bound galacturonosyltransferase from epicotyls of azuki bean, *Biosci. Biotech. Biochem.* 65:1519-1527 (2001).
15. Akita, K. et al., Successive glycosyltransfer activity and enzymatic characterization of pectic polygalacturonate 4-α-galacturonosyltransferase solubilized from pollen tubes of *Petunia axillaris* using pyridylaminated oligogalacturonates as substrates, *Plant Physiol.* 130:374-379 (2002).
16. Reithmeier, R. A. F. et al., Intrinsic membrane protein structure: principles and prediction, in: "The Structure of Biological Membranes", P. Yeagle., ed., CRC Press, Boca Raton, pp. 337-393 (1992).
17. Northcote, D. H., The Golgi apparatus. *Endeavor* 30:26-33 (1971).
18. Northcote, D. H. et al., A function of the Golgi Apparatus in polysaccharide synthesis and transport in the root-cap cells of wheat, *Biochem. J.* 98:159-167 (1966).
19. Harrism, P. J. et al., Polysaccharide formation in plant golgi bodies. Biochim. Biophys. Acta 237:56-64 (1971).
20. Stoddart, R. W. et al., Metabolic relationships of the isolated fractions of the pectic substances of actively growing sycamore cells. *Biochem. J.* 105:45-59 (1967).
21. Moore, P. J. et al., Spatial organization of the assembly pathways of glycoproteins and complex polysaccharides in the golgi apparatus of plants. *J. Cell Biol.* 112:589-602 (1991).
22. Staehelin, L. A. et al., The plant Golgi apparatus: structure, functional organization and trafficking mechanisms, *Annu. Rev. Plant Physiol. Plant Mol.*
Biol. 46:261-288 (1995).
23. Willats, W. G. T. et al., Making and using antibody probes to study plant cell walls, *Plant Physiol. Biochem.* 38:27-36 (2000).
24. Goubet, F. et al., Subcellular localization and topology of homogalacturonan methyltransferase in suspension-cultured *Nicotiano tabacum* cells, *Planta* 209:112-117 (1999).
25. Vannier, M. P. et al., Localization of methyltransferase activities throughout the endomembrane complex system of flax (*Linum usitatissimum* L) hypocotyls, *Biochem. J.* 286:863-868 (1992).
26. Bourlard, T. et al., Various pectin methyltransferase activities with affinity for low and highly methylated pectins, *Plant Cell Physiol.* 38:259-267 (1997).
27. O'Neill, M. et al., The pectic polysaccharides of primary cell walls, in: "Methods in Plant Biochemistry, Volume 2", P. M. Dey., ed., Academic Press, London, pp. 415-441 (1990).
28. Lau, J. M., et al., Structure of the backbone of rhamnogalacturonan I, a pectic polysaccharide in the primary cell walls of plants, Carbohydr. Res. 137:111-125 (1985).
29. Eda, S. et al., A pectic polysaccharide from cell walls of tobacco (*Nicotiana tabacum*) mesophyll, Carbohydr. Res. 158:205-216 (1986).
30. Carpita, N. C. et al., Structural models of primary cell walls in flowering plants: consistency of molecular structure with the physical properties of the walls during growth, *Plant J.* 3:1-30 (1993).

31. O'Neill, M. A. et al., Rhamnogalacturonan-II, a pectic polysaccharide in the walls of growing plant cell, forms a dimer that is covalently cross-linked by a borate ester—in vitro conditions for the formation and hydrolysis of the dimer, *J. Biol. Chem.* 272:3869(1997).
32. Schols, H. A. et al., A xylogalacturonan subunit present in the modified hairy regions of apple pectin, Carbohydr. Res. 279:265-279 (1995).
33. Kikuchi, A. et al., A xylogalacturonan whose level is dependent on the size of cell clusters is present in the pectin from cultured carrot cells, *Planta* 200:369-372 (1996).
34. Yu, L. et al., Partial characterization of xylogalacturonans from cell walls of ripe watermelon fruit: Inhibition of endopolygalacturonase activity by xylosylation, in: "Pectins and Pectinases", J. Visser et al., *Elsevier*, Amsterdam, pp. 79-88 (1996).
35. Aspinall, G. O., Chemistry of cell wall polysaccharides in: "The Biochemistry of Plants, Vol.3.", J. Preiss., ed., Academic Press, New York, pp. 473-500 (1980).
36. Watson, R. R. et al., Chemistry and biochemistry of apiose, *Adv. Carbohydr.* Chem. Biochem. 31:135-184 (1975).
37. Hart, D. A. et al., Isolation and partial characterization of apiogalacturonans from the cell wall of *Lemna minor*, *Biochem. J.* 116:569-579 (1970).
38. Schols, H. A. et al., Structural features of hairy regions of pectins isolated from apple juice produced by the liquefaction process, *Carbohydr. Res.* 206:117-129 (1990).
39. Mohnen, D. et al., Cell free synthesis of the pectic polysaccharide homogalacturonan, in: "Pectins and Pectinases", J. Visser et al., *Elsevier Science* B.V. Amsterdam, pp.109-126 (1996).
40. Willats, W. G. T. et al., Pectin: cell biology and propects for functional analysis, *Plant Mol. Biol.* 47:9-27 (2001).
41. An, J. et al., Isolation and structural characterization of alpha-D-glucosyluronic acid and 4-O-methyl alpha-D-glucosyluronic acid-containing oligosaccharides from the cell-wall pectic polysaccharide, rhamnogalacturonan I, *Carbohydr. Res.* 252:235-243 (1994).
42. An, J. et al., Isolaton and structural characterization of endo-rhamnogalacturonase-generated fragments of the backbone of rhamnogalacturonan I, *Carbohydr. Res.* 264: 83-96 (1994).
43. O'Neill, M. A. et al., Requirement of borate cross-linking of cell wall rhamnogalacturonan II for *Arabidopsis* growth, *Science* 294:846-849 (2001).
44. Atkinson, R. G. et al., Overexpression of polygalacturonase in transgenic apple trees leads to a range of novel phenotypes involving changes in cell adhesion, *Plant Physiol.* 129:122-133 (2002).
45. Mohnen, D. et al., Cell wall carbohydrates as signals in plants, *Sem. Cell Biol.* 4:93-102 (1993).
46. Côté, F. et al., Oligosaccharide elicitors in host-pathogen interactions generation, perception, and signal transduction, in: "Plant-Microbe Interactions", B. B. Biswas et al., Plenum Press, New York, pp. 385-432 (1998).
47. Mollet, J.-C. et al., A lily stylar pectin is necessary for pollen tube adhesion to an in vitro stylar matrix, *Plant Cell* 12:1737-1749 (2000).
48. Western, T. L. et al., Isolation and characterization of mutants defective in seed coat mucilage secretory cell development in *Arabidopsis*, *Plant Physiol.* 127:998-1011 (2001).
49. Willats, W. G. T. et al., In-situ analysis of pectic polysaccharides in seed mucilage and at the root surface of *Arabidopsis thaliana*, *Planta* 213:37-44 (2001).
50. González-Carranza, Z. H. et al., Temporal and spatial expression of a polygalacturonase during leaf and flower abscission in oilseed rape and *Arabidopsis*, *Plant Physiol.* 128:534-543 (2002).
51. Brown, K., Xylem may direct water where it's needed, *Science* 291:571-572 (2001).
52. Fry, S. et al., Oligosaccharides as Signals and Substrates in the Plant Cell Wall, *Plant Physiol.* 103:1-5 (1993).
53. Shibuya, N. et al., Oligosaccharide signalling for defence responses in plant, *Physiol. Mol. Plant Pathol.* 59:223-233 (2001).
54. Skjot, M. et al., Direct interference with rhamnogalacturonan I biosynthesis in Golgi vesicles, *Plant Physiol.* 129: 95-102 (2002).
55. Bouton, S. et al., QUASIMODO1 encodes a putative membrane-bound glycosyltransferase required for normal pectin synthesis and cell adhesion in *Arabidopsis*, *Plant Cell* 14:2577-2590 (2002).
56. Edwards, M. E. et al., Molecular characterisation of a membrane-bound galactosyltransferase of plant cell wall matrix polysaccharide biosynthesis, *Plant J.* 19:691-697 (1999).
57. Perrin, R. M. et al., Xyloglucan fucosyltransferase, an enzyme involved in plant cell wall biosynthesis, *Science* 284:1976-1979 (1999).
58. Faik, A. et al., An Arabidopsis gene encoding an alpha-xylosyltransferase involved in xyloglucan biosynthesis, *Proc. Natl. Acad. Sci. USA* 99:7797-7802 (2002).
59. Delmer, D. P., A hot mutant for cellulose synthesis, *Trends in Plant Science* 3:164 (1998).
60. Orellana, A. et al., Enzymatic synthesis and purification of [$^3$H] uridine diphosphate galacturonic acid for use in studying Golgi-localized transporters, *Analytical Biochemistry* 272:224-231 (1999).
61. Crombie, H. J. et al., A homogalacturonan synthase from mung bean hypocotyls, *Cell Wall '01—9th International Cell Wall Meeting*, Sep. 2-7, 2001 Toulouse, France 131 (2001).(Abstract)
62. Cumming, C. M. et al., A galacturonyltransferase involved in pectin biosynthesis. in: "Cell Walls '86. Proceedings of the Fourth Cell Wall Meeting. Paris—Sep. 10-12, 1986", B. Vian et al., Université Pierre et Marie Curie—Ecole Normale Supérieure. Paris, pp. 360-363 (1986).
63. Sterling, J. D. et al., Development of a filter assay for measuring homogalacturonan:alpha1,4-galacturonosyltransferase activity, (in preparation)
64. Williams, N., Rain forest fragments fare poorly, *Science* 278:1016(1997).
65. Pagès, S. et al., Changing a single amino acid residue switches processive and non-processive behavior of *Aspergillus niger* endopolygalacturonase I and II, *J. Biol. Chem.* 276:33652-33656 (2001).
66. Campbell, J. A. et al., A classification of nucleotide-diphospho-sugar glycosyltransferases based on amino acid sequence similarities, *Biochem. J.* 326:929-942 (1997).
67. Henrissat, B. et al., Glycoside hydrolases and glycosyltransferases. Families, modules, and implications for genomics. *Plant Physiol* 124:1515-1519 (2000).
68. Jones, D. T., GenTHREADER: An Efficient and Reliable Protein Fold Recognition Method for Genomic Sequences, *J. Mol Biol.* 287:797-815 (1999).
69. McGuffin, L. J. et al., The PSIPRED protein structure prediction server, *Bioinform. Applic. Note.* 16:404-405 (2000).
70. Persson, K. et al., Crystal structure of the retaining galactosyltransferase LgtC from *Neisseria meningitidis* in com- 70. plex with donor and acceptor sugar analogs, *Nature Structural Biology* 8:166-175 (2001).
71. Price, N. J. et al., Plant glycosyltransferases, *Curr. Opin. Plant Biol.* 2001:219-224 (2001).
72. Charnock, S. J. et al., Three-dimensional structures of UDP-sugar glycosyltransferases illuminate the biosynthesis of plant polysaccharides, *Plant Physiol* 125:527-531 (2001).
73. Ünligil, U. M. et al., Glycosyltransferase structure and mechanism, *Current Opinion in Structural Biology* 10:510-517 (2000).
74. Boix, E. et al., Structural basis of ordered binding of donor and acceptor substrates to the retaining glycosyltransferase, alpha-1,3-galactosyltransferase, *J. Biol Chem.* 277:28310-28318 (2002).
75. Cabral, C. M. et al., Organizational diversity among distinct glycoprotein endoplasmic reticulum-associated degradation programs, *Mol. Biol. Cell* 13:2639-2650 (2002).
76. Mallisard, M. et al., Expression of functional soluble forms of human alpha-1,4-galactosyltransferase I, alpha-2,6-sialyltransferase, and alpha-2,6-sialyltransferase, and alpha-1,3-fucosyltransferase VI in the methylotrophic yeast *Pichia pastoris,* Biochem. Biophys. Res. Commun. 267:169-173 (2000).
77. Romero, P. A. et al., KTR1P is an alpha-1,2-mannosyltransferase of *Saccharomyces cerevisiae* comparison of the enzymatic properties of soluble recombinant KTR1P and KRE2P/MNT1P produced in *Pichia pastoris, Biochemical Journal* 321:289-295 (1997).
78. Hochstrasser, U. et al., Expression of a functional barley sucrose-fructan 6-fructosyltransferase in the methylotrophic yeast Pichia pastoris, *Febs Letters* 440:356-360 (1998).
79. Gallet, P. F. et al., Heterologous expression of an engineered truncated form of human Lewis fucosyltransferase (Fuc-TIII) by the methylotrophic yeast *Pichia pastoris, Glycobiology* 8:919-925 (1998).
80. Moreman, K. W. et al., Topology of mannosidasw II in rat liver membrane and release of the cataytic domain by selective proteolysis, *Jr Biol. Chem* 23:10945-10951 (1986).
81. Merkle, R. K. et al., Cloning, expression, purification, and charactarization of the murine lysosomal acid alpha-mannosidase, *Biochim. Biophys. Acta* 1336:132-146 (1997).
82. Liao, Y. F. et al., Cloning, expression, purification, and characterization of the human broad-specificity lysosomal acid alpha-mannosidase, *J. Biol. Chem.* 271:28348-28358 (1996).
83. Bar-Peled, M. et al., UDP-rhamnose:flavanone-7-O-glucoside-2"-O-rhamnosyltransferase. Purification and characterization of an enzyme catalyzing the production of bitter compounds in citrus, *J. Biol. Chem.* 266:20953-20959 (1991).
84. Basu, S. S. et al., A facile enzymatic synthesis of uridine diphospho-[14C]galacturonic acid, *Anal. Biochem.* 280:173-177 (2000).
85. Quigley, H. F. et al., A non-radioactive gel electrophoresis assay for homogalacturonan alpha-1,4-galacturonosyltransferase, (in preparation).
86. Bao, M. et al., Bovine UDP-N-acetylglucosamine:lysosomal-enzyme N-acetylglucosamine-1-phosphotransferase. I. Purification and subunit structure, *J. Biol. Chem.* 271:31437-31445 (1996).
87. Briand, J. P. et al., Application and limitations of the multiple antigen peptide (MAP) system in the production and evaluation of anti-peptide and anti-protein antibodies, *J. Immunol. Methods* 156:255-265 (1992).
88. Ziehl, V. et al., Polyclonal antibodies directed against synthetic N-terminus of fungal endopolygalacturonase recognizes the native protein and cross-reacts with endopolygalacturonase of a different funal species, Abstract, Pectins and Pectinases meeting, Wageningen, Netherlands, (1995)
89. Harlow, E. et al., Antibodies: A laboratory manual, Cold Spring Harbor Press, Cold Spring Harbor, N.Y., (1988).
90. Mohnen, D. et al., Hormonal regulation of alpha1,3-glucanase messenger RNA levels in cultured tobacco tissues. *EMBO J.* 4:1631-1635 (1985).
91. Zhang G. F. et al., Functional compartmentation of the golgi apparatus of plant cells; Immunocytochemical analysis of high-pressure frozen- and freeze-substituted sycamore maple suspension culture cells, *Plant Physiol.* 99:1070-1083 (1992).
92. Colley, K. J., Golgi localization of glycosyltransferases: more questions than answers, *Glycobiology* 7:1-13 (1997).
93. Opat, A. S. et al., Trafficking and localization of resident Golgi glycosylation enzymes, *Biochemie* 83:763-773 (2001).
94. Dirnberger, D. et al., The Golgi localization of *Arabidopsis thaliana* B1,2-xylosyltransferase in plant cells is dependent on its cytoplasmic and transmembrane sequences, *Plant Mol. Biol.* 50:273-281 (2002).
95. Munro, S., An investigation of the role of transmembrane domains in golgi protein retention, *The EMBO Journal* 14:4695-4704 (1995).
96. Nilsson, T. et al., Kin recognition. A model for the retention of Golgi enzymes. *FEBS Left.* 330:1-4 (1993).
97. Freshour, G. et al., Developmental and tissue-specific structural alterations of the cell-wall polysaccharides of *Arabidopsis thaliana* Roots, *Plant Physiol.* 110:1413-1429 (1996).
98. Samuels, A. L. et al., Cytokinesis in tobacco BY-2 and root tip cells: a new model of cell plate formation in higher plants, *J. Cell Biol.* 130:(1995).
99. Lam, B. C.-H. et al., Role of SH3 Domain-Containing Proteins in Clathrin-Mediated Vesicle Trafficking in *Arabidopsis, Plant Cell* 13:2499-2512 (2001).
100. Chuang, C.-F. et al., Specific and heritable genetic interference by double-stranded RNA in *arabidopsis thaliana, Proc. Natl. Acad. Sci. USA* 97:4985-4990 (2000).
101. Bent, A. F. et al., RPS2 of *Arabidopsis thaliana:* A Leucine-Rich Repeat Class of Plant Disease Resistance Genes, *Science* 265:1856-1860 (1994).
102. Bieberich, E. et al., Regulation of Ganglioside Biosynthesis by Enzyme Complex Formation of Glycosyltransferases, *Biochem.* 41:11479-11487 (2002).
103. Ridley, B. L. et al., A method for biotin labeling of biologically active oligogalacturonides using a chemically stable hydrazide linkage, *Anal. Biochem.* 249:10-19 (1997).
104. Guillaumie, F. et al., Solid-phase biosynthesis and MALDI-TOF mass spectrometry analysis of pectic oligogalacturonides: a new tool to monitor the extension of a homogalacturonan chain, *Carbohydr. Res.* (2002).
105. Yamada, H. et al., Structural Characterization and Antitumor Activity of a Pectic Polysaccharide from the Roots of *Angelica acutiloba. planta medica* 56:182-186, (1990).
106. Olano-Martin, E. et al., Pectin and pectic-oligosaccharides induce apoptosis in in vitro human colonic adenocarcinoma cells. *Anticancer research* 23:341-346, (2003.).
107. Avivi-Green, C. et al., Pectin-enriched diet affects distribution and expression of apoptosis-cascade proteins in colonic crypts of dimethylhydrazine-treated rats. *Int J Mol Med* 6:689-698 (2000a).

108. Avivi-Green, C. et al., Apoptosis cascade proteins are regulated in vivo by high intracolonic butyrate concentration: correlation with colon cancer inhibition. *Oncol Res* 12:83-95 (2000b).
109. Ohno, K. et al., Inhibitory effect of apple pectin and culture condensate of Bifidobacterium longum on colorectal tumors induced by 1,2-dimethylhydrazine in trangenic mice harboring human prototype c-Ha-ras genes. *Exp Anim* 49:305-307 (2000).
110. Davidson, L. A., et al., Morphodensitometric anaylsis of protein kinase C Bu expression in rat colon: modulation by diet and relation to in situ cell proliferation and apoptosis. *Carcinogenesis* 21:1513-1519 (2000).
111. Fernandez, M. L., Citrus pectin and cholesterol interact to regulate hepatic cholesterol homeostasis and lipoprotein metabolism: a dose-response study in guinea pigs. *Am J Clin Nutr* 59: 869-878 (1994).
112. Behall, K. et al., In: M L Fishman and J J Jen, eds, Chemistry and Function of Pectins, American Chemical Society, Washington, D.C. pp 248-265 (1986).
113. Levitt, N. S. et al., The effect of dietary fiber on glucose and hormone responses to a mixed meal in normal subjects and in diabetic subjects with and without autonomic neuropathy. *Diabetes Care* 3: 505-519 (1980).
114. Hayashi, A. et al., Effects of daily oral administration of quercetin chalcone and modified citrus pectin on implanted colon-25 tumor growth in bulb-c mice. *Altern Med Rev* 5: S-546-552 (2000).
115. Inohara, H. et al., Effects of natural complex carbohydrates (citrus pectin) on murine melanoma cell properties related to galectin-3 functions. *Glycoconjugates Journal* 11: 527-532 (1994).
116. Dongowski, G, et al., In: J Visser and AGJ Voragen, eds, Pectins and Pectinases, *Elsevier Science* B.V. Amsterdam, pp 659-666 (1996).
117. Honjo, Y. et al., Expression of Cytoplasmic Galectin-3 as a Prognostic Marker in Tongue Carcinoma. *Clinical Cancer Research.* 6(12):4635-40, (2000).
118. Honjo, Y. et al., Down-Regulation of Galectin-3 Suppresses Tumorigenicity of Human Breast Carcinoma Cells. *Clinical Cancer Research.* 7(3):661-8, (2001).
119. Yoshii, T. et al., Galectin-3 maintains the transformed phenotype of thyroid papillary carcinoma cells. *Int. J. Oncol.* 18(4):787-92, (2001).
120. Naik, H. et al., Inhibition of in vitro tumor cellendothelial adhesion by modi citrus pectin: a pH modified natural complex carbohydrate (Meeting abstract) *Proc Annul Meet Am Assoc Cancer Res.;*36: 377 (1995).
121. Platt, D. et al., Modulation of the lung colonization of B16-F1 melanoma cells by citrus pectin. *J Natl Cancer Inst.;* 84(6):438-442 (1992).
122. Strum, S. et al., International Conference on Diet and Prevention of Cancer (Finland). May (1999).
123. Liu, C. et al., Citrus pectin: characterization and inhibitory effect on fibroblast growth factor-receptor interaction. *J Agric Food Chem* 49: 3051-3057 (2001).
124. Rolin, C. Pectin. In: R L Whistler and J N BeMiller, eds, Industrial Gums—Polysaccharides and Their Derivatives, Third Ed. Academic Press, San Diego, pp 257-293 (1993).
125. Nangia-Makker, P. et al. Inhibition of human cancer cell growth and metastasis in nude mice by oral intake of modified citrus pectin. *J. Natl. Cancer Inst.* 94: 1854-1862 (2002).
126. Dongowski, G et al., Degradation of pectins with different degrees of esterification by *Bacteroides thetaiotaomicron* isolated from human gut flora. *Appl Environ Microbiol* 66: 1321-1327 (2000).
127. Pienta, K. J. et al., Inhibition of spontaneous metastasis in a rat prostate cancer model by oral administration of modified citrus pectin, *J. Natl. Cancer Inst.* 87:348-353 (1995).
128. Zwieniecki, M. A. et al., Hydrogel control of xylem hydraulic resistance in plants, *Science* 291:1059-1062 (2001).
129. Skjot, M. et al., Direct interference with rhamnogalacturonan I biosynthesis in Golgi vesicles, *Plant Physiol.* 129:95-102 (2002).
130. Iwai, H., A pectin glucuronyltransferase gene is essential for intercellular attachment in the plant meristem, *Proc. Natl. Acad. Sci. USA* 99:16319-16324 (2002).
131. York, W. S. et al., Isolation and characterization of plant cell walls and cell wall components. *Methods Enzymol.* 118:3-40 (1985).
132. Vidal, S. et al., Structural characterization of the pectic polysaccharide rhamnogalacturonan II: evidence for the backbone location of the aceric acid-containing oligoglycosyl side chain, *Carbohydr. Res.* 326:277-294 (2000).
133. Whitcombe, A. J. et al., Structural characterization of the pectic polysacchride, Rhamnogalacturonan-II, *Carbohydr. Res.* 271:15-29 (1995).
134. Boyes, D. C. et al., Growth stage-based phenotypic analysis of *arabidopsis:* a model for high throughput functional genomics in plants, *Plant Cell* 13:1499-1510 (2001).
135. Zablackis, E. et al., Characterization of the cell-wall polysaccharides of *Arabidopsis thaliana* leaves, *Plant Physiol.* 107:1129-1138 (1995).
136. Madson, M. et al., The MUR3 gene of Arabidopsis encodes a xyloglucan galactosyltransferase that is evolutionarily related to animal exostosins, *Plant Cell* 15:1662-1670 (2003).

We claim:

1. An isolated nucleic acid comprising a sequence encoding a polypeptide having galacturonosyltransferase (GALAT1) activity, wherein the polypeptide comprises an amino acid sequence identical to or comprises a sequence with at least 95% amino acid sequence similarity with the sequence set forth in SEQ ID NO:2 and wherein the galacturonosyltransferase catalyzes transfer of galacturonosyl residues to an oligomer of galacturonic acid residues, and a transcription regulatory sequence, wherein said sequence encoding the polypeptide and the transcription regulatory sequence are operably linked, and wherein said sequences are not associated together in nature.

2. The nucleic acid of claim 1 wherein the polypeptide comprises the amino acid sequence as set forth in SEQ ID NO: 2.

3. The nucleic acid of claim 2 wherein the nucleic acid comprises SEQ ID NO: 1.

4. An expression vector comprising the nucleic acid of claim 1, wherein the transcription regulatory sequence is a promoter that functions in plants.

5. A transgenic plant which has been transformed with the expression vector of claim 4.

6. Progeny of the transgenic plant of claim 5, wherein said progeny comprises the nucleic acid of claim 1.

* * * * *